United States Patent
Bottegoni et al.

(10) Patent No.: US 9,828,352 B2
(45) Date of Patent: Nov. 28, 2017

(54) PHENYL CARBAMATES AND THEIR USE AS INHIBITORS OF THE FATTY ACID AMIDE HYDROLASE (FAAH) ENZYME AND MODULATORS OF THE D3 DOPAMINE RECEPTOR (D3DR)

(71) Applicants: FONDAZIONE ISTITUTO ITALIANO DI TECNOLOGIA, Genoa (IT); THE REGENTS OF THE UNIVERSITY OF CALIFORNIA, Oakland, CA (US)

(72) Inventors: Giovanni Bottegoni, Genoa (IT); Alessio De Simone, Genoa (IT); Gian Filippo Ruda, Genoa (IT); Andrea Cavalli, Genoa (IT); Tiziano Bandiera, Genoa (IT); Daniele Piomelli, Oakland, CA (US)

(73) Assignees: FONDAZIONE ISTITUTO ITALIANO DI TECNOLOGIA, Genoa (IT); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/905,727

(22) PCT Filed: Jul. 10, 2014

(86) PCT No.: PCT/EP2014/064853
§ 371 (c)(1),
(2) Date: Jan. 15, 2016

(87) PCT Pub. No.: WO2015/007615
PCT Pub. Date: Jan. 22, 2015

(65) Prior Publication Data
US 2016/0194296 A1  Jul. 7, 2016

Related U.S. Application Data

(60) Provisional application No. 61/847,807, filed on Jul. 18, 2013.

(51) Int. Cl.
| | | |
|---|---|---|
| *C07D 209/20* | (2006.01) |
| *C07D 209/88* | (2006.01) |
| *C07D 211/38* | (2006.01) |
| *C07D 211/14* | (2006.01) |
| *C07D 213/30* | (2006.01) |
| *C07D 295/13* | (2006.01) |
| *C07D 295/125* | (2006.01) |
| *A61K 31/495* | (2006.01) |
| *A61K 31/496* | (2006.01) |
| *A61K 31/5377* | (2006.01) |

(52) U.S. Cl.
CPC ......... *C07D 295/13* (2013.01); *C07D 209/88* (2013.01); *C07D 211/14* (2013.01); *C07D 211/38* (2013.01); *C07D 213/30* (2013.01); *C07D 295/125* (2013.01)

(58) Field of Classification Search
None
See application file for complete search history.

(56) References Cited

FOREIGN PATENT DOCUMENTS

| | | |
|---|---|---|
| CN | 103073524 A | 5/2013 |
| WO | WO 03/028728 A1 | 4/2003 |
| WO | WO 2004/033422 A2 | 4/2004 |
| WO | WO 2004/099176 A1 | 11/2004 |

OTHER PUBLICATIONS

Database WPI, Week 201381, Thomson Scientific, London, GB, XP002729757. (Abstract of CN 103073524 A), (2013).
De Simone et al., "Applying a multitarget rational drug design strategy: the first set of modulators with potent and balanced activity toward dopamine D3 receptor and fatty acid amide hydrolase," Chemical Communications, May 18, 2014, pp. 4904-4907, vol. 50, No. 38.
International Search Report of PCT/EP2014/064853 dated Sep. 29, 2014.

*Primary Examiner* — Emily Bernhardt
(74) *Attorney, Agent, or Firm* — Arent Fox LLP

(57) ABSTRACT

The invention provides compounds of Formula (I) or pharmaceutically acceptable salts thereof

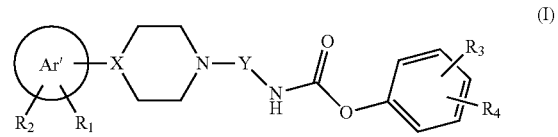

wherein Ar', $R_1$, $R_2$, $R_3$, $R_4$, X, Y are as defined in the description of invention, as multi-target directed ligands (MTDLs) that are at the same time inhibitors of the fatty acid amide hydrolase (FAAH) enzyme and modulators of the D3 dopamine receptor (D3DR), their methods of preparation, formulations and therapeutic applications thereof.

5 Claims, No Drawings

PHENYL CARBAMATES AND THEIR USE AS INHIBITORS OF THE FATTY ACID AMIDE HYDROLASE (FAAH) ENZYME AND MODULATORS OF THE D3 DOPAMINE RECEPTOR (D3DR)

CROSS-REFERENCES TO RELATED APPLICATIONS

This application is a National Stage entry of International Patent Application No.: PCT/EP2014/064853, filed Jul. 10, 2014, which claims priority claiming the benefit of U.S. Provisional application Ser. No. 61/847,807 filed Jul. 18, 2013, the disclosure of which is incorporated herein by reference.

STATEMENT AS TO RIGHTS TO INVENTIONS MADE UNDER FEDERALLY SPONSORED RESEARCH OR DEVELOPMENT

This research was made, in part, with government support under NIH Grant R01 DA12413 awarded by the National Institutes of Health; the United States Government has certain rights in the invention.

FIELD OF THE INVENTION

The present invention discloses multi-target directed ligands (MTDLs) that are at the same time inhibitors of the fatty acid amide hydrolase (FAAH) enzyme and modulators of the D3 dopamine receptor (D3DR), their methods of preparation, their formulations as medicaments, and their therapeutic application for the treatment of pathologies, conditions and disorders which would clinically benefit from the combined inhibition of the fatty acid amide hydrolase enzyme and modulation of the D3 dopamine receptor.

BACKGROUND OF THE INVENTION

Being responsible for over five million deaths every year, tobacco smoking is a chronic and deteriorating syndrome that represents one of the most severe health threats in Western countries. A recent analysis (Syed and Chaudhari, Nature Rev. Drug Discovery, 2013; 12: 97-98) estimates that there are over 1.3 billion smokers worldwide, placing the prevalence of tobacco addiction in adult population around 33%. While it is the enduring exposure to the many harmful substances contained in cigarette smoke that eventually leads to cardiovascular conditions, lung diseases, cancer, and other disorders, tobacco addiction is caused by nicotine. Nicotine is a psychoactive alkaloid that exerts its action increasing the level of dopamine in the mesolimbocortical system, a specific brain circuit strictly connected to reward, motivated behavior, and cue- and stress-induced drug craving (Caponnetto et al., Curr. Opin. Pharmacol., 2012; 12: 229-237). More in details, nicotine is an agonist of central nicotinic acetylcholine receptors (nAChRs). Upon binding, it increases the firing rate of the dopamine neurons that from the ventral tegmental area project toward the nucleus accumbens. Nicotine dependence is a very strong form of addiction, with the majority of smokers that attempt to quit relapsing within one month.

There are several medications approved by regulatory authorities for the treatment of nicotine addiction: i) nicotine replacement products, ii) Varenicline, an antagonist of the $\alpha_4\beta_2$ nicotinic receptor, and iii) Buproprion, a non-tricyclic antidepressant. Nicotine vaccines based on active and passive immunization strategies are currently being in clinical development. Currently available treatments have shown promising effects in attenuating the symptoms of nicotine withdrawal but their success in preventing relapse and maintain long-term abstinence from nicotine has been only marginal (Benowitz, Annu. Rev. Pharmacol. Toxicol., 2009; 49: 57-71). It is important to note that a statistically significant co-morbidity between nicotine addiction, post-traumatic stress disorder (PTSD), and depression proneness has been consistently reported. For example, among combat veterans affected by PTSD, nicotine addiction was positively related to PTSD symptoms (Thorndike, Addict Behav., 2006; 31: 223-231). Smokers with PTSD are significantly more likely to be heavy smokers, i.e., those who smoke more than 25 cigarettes daily. Sustained release of bupropion has been shown to be effective for a short term smoking cessation in studies involving veterans with diagnosed PTSD and other concomitant psychiatric conditions (Hertzberg, J. Clin. Psychopharmacol., 2001; 21: 91-98).

D3 dopamine receptor (D3DR) is a molecular target that has been intensively investigated for the development of novel and efficient medications for the treatment of nicotine addiction (Le Foll et al., Expert Op. Invest. Drugs, 2007; 16: 45-57). In fact, this receptor subtype is mainly expressed in the mesolimbocortical system. In preclinical animal models, D3DR modulators were able to decrease the compulsion for nicotine self-administration under reinforcement schedules and prevented the establishment of Pavlovian drug-seeking behaviors. This suggests a translational strategy in which D3DR modulators could be used to attenuate the effects of drug-associated stimuli that eventually lead to the reinstatement of drug-seeking patterns. However, D3DR modulators did not display significant effects on nicotine intrinsic action and only had moderate effects on withdrawal.

Recently, behavioral and neurochemical evidences have established that the inhibition of the fatty acid amide hydrolase (FAAH) enzyme is effective in counteracting the abuse-related effects of nicotine. FAAH enzyme is a membrane bound serine hydrolase, member of the amidase signature family, characterized by an unusual Ser-Ser-Lys catalytic triad. FAAH catalyzes the degradation of several fatty acid N-acyl ethanolamides (FAEs), endogenous ligands for both cannabinoid (CB) receptors and nuclear peroxisome-proliferator activated receptors (PPAR) (Panlilio et al., Pharmacol. Ther., 2013; 138: 84-102). Selective FAAH enzyme inhibitors were able to reduce the nicotine-induced elevation of dopamine in the mesolimbocortical system, preventing the acquisition of nicotine self-administration and nicotine-induced preferential behaviors. These inhibitors acted elevating the levels of oleoylethanolamide (IDEA) and palmitoylethanolamide (PEA), endogenous agonists of nuclear receptor PPAR-alpha. Activation of PPAR-alpha increases the activity of several tyrosine kinases, which, in turn, blocks the downstream signaling initiated by nicotine binding to nAChRs (Mascia et al., Biol. Psychiatry, 2011; 69: 633-641). Moreover, blocking the cleavage of anandamide, FAAH enzyme inhibition has also been associated with an anxiolytic effect, which counteracts withdrawal symptoms and substance- and cue-induced relapse (Justinova et al., Biol. Psychiatry, 2008; 64: 930-937).

In this scenario, it is possible to envision treatment strategies that address both nicotine-craving symptoms and relapse by combining an inhibitor of the FAAH enzyme with a D3 receptor modulator. Moreover, this combination turns out to be beneficial for the treatment of other comorbid conditions often associated with nicotine addiction such as the already mentioned PTSD, as well as anxiety, pathological behaviours, and schizophrenia (Wu et al., J. Clin. Psychopharmacol., 2013; 33: 319-28). In case of schizophrenia, the combination of an inhibitor of the FAAH enzyme with a D3 receptor modulator could cause in specific brain areas a rise in the anandamide levels, which have been shown to negatively correlate with psychotic symptoms, pointing toward a protective role for anandamide (Leweke et al., Translational Psychiatry, 2012; 2: e94) and, at the same time, engage dopamine D3 improving cognitive function, emotional processing, executive function, flexibility, and social behavior, as demonstrated by in vivo experiments in animal models (Gross and Dresker, Handb. Exp. Pharmacol., 2012; 213: 167-210).

However, this combination therapy, presents some drawbacks. In addition to face the cumbersome administration of two separate drugs, which is something that generally hampers compliance, especially in patients diagnosed with psychotic symptoms, different pharmacokinetics of the respective drugs can impact on different pharmacodynamics. In practice, the clinician should face and manage a combination therapy with two different ADME curves (Absorption Distribution Metabolism Excretion). An innovative alternative to drug combinations are drugs that can hit multiple targets the so-called multi-target directed ligands (MTDLs; Cavalli et al. J. Med. Chem., 2008; 51:347-72). The strategy of targeting two or more proteins at the same time with a single compound can provide therapeutic effects superior to those of a selective drug (Zimmermann et al., Drug Discovery Today, 2007; 12: 34-42; Morphy R. and Rankovic Z. Drug Discovery Today, 2007, 12, 156-60; Hopkins A. L., Nat. Chem. Biol., 2008; 4: 682-90). This can be explained by the number of potential benefits offered by the use of MTDLs over cocktails or multicomponent drugs. The advantages of MTDLs can be summarized as follows: 1) reduced uncertainty in clinical development since predicting the pharmacokinetics of a single compound is much easier than with a drug cocktail, overcoming the problem of different bioavailability, pharmacokinetics and metabolism; 2) certainty on the pharmacodynamics; 3) improved effect of simultaneously inhibiting multiple targets; 4) improved safety by decreasing the side effects related to the load of a drug cocktail (reduced risk of drug-drug interactions); this is particularly relevant for drug metabolism, where the competition of different drugs for the same metabolic enzyme affect their toxicity. Another important advantage is a simplified therapeutic regimen and improved compliance, which is particularly important for patients that might experience relapse.

The MTDLs strategy is an innovative approach to the development of a centrally acting novel drug for the treatment of complex disorders, especially in view of the fact that the major basic processes that eventually lead to dependence are multi-factorial in nature (Gardner et al., Adv. Psychosom. Med., 2011; 30: 22-60). Such a strategy is based on the concept that a single multifunctional compound can be administered to hit multiple targets that cooperate in establishing and sustaining nicotine addiction, and therefore would prevent unwanted compensation among interacting pathways. Indeed, MTDLs could represent a practical alternative to the use of drug combinations. Since many substances of abuse share the basic mechanisms that induce addiction, such MTDLs may also be used as medications for other conditions that would clinically benefit from the combined inhibition of the fatty acid amide hydrolase enzyme and modulation of the D3 dopamine receptor.

One problem associated to MTDLs is that many of them have low efficiency in terms of their binding energy per unit of molecular weight. This is because they contain groups that are only important for one of the targets, being merely tolerated by the others. This results in an unbalanced profile (Morphy R. et al., Drug Discov. Today, 2007; 12: 156-160; Morphy R., J. Med. Chem., 2006; 4: 2969-2978). The way to fuse in a single molecule two pharmacophore elements, one distinctive of the FAAH molecular target and the other able to recognize the second molecular target (D3DR) is not obvious, as well as not obvious is the required optimization of both activities.

The inventors have solved this problem and unexpectedly found a class of compounds that is able to simultaneously inhibit the FAAH enzyme and modulate the D3D receptor, thus offering a superior medication to treat syndromes associated to the dependence and addiction to nicotine and other drugs of abuse.

KNOWN ART

Aryl piperazines and aryl piperidines constitute a class of dopamine receptor antagonists well known in the art. Several patents, patent applications and scientific publications describe the structures and therapeutic applications of such compounds as dopamine receptor modulators.

U.S. Pat. No. 7,056,922 claims some N-acylamino cyclopropanyl aryl piperazine derivatives as modulators of dopamine D3 receptors. U.S. Pat. No. 8,334,289 claims certain pyridinoyl aryl piperazine derivatives as modulator of dopamine D3 receptors. WO2006/072608 and WO2008/043839 describe aryl piperazine and aryl piperidine derivatives as modulators of dopamine D2-like and serotonine 5-$HT_2$ receptor subtypes. WO2010/034648 describes certain pyridin-2-yl-piperazines having affinity and selectivity for dopamine D3 receptors. WO2009/112568, WO2009/095438 and WO2010/040808 disclose several aryl piperazine derivatives as modulators of dopamine D3 and serotonine 5-$HT_{2A}$ receptors, with potential medical utility. WO2006/072608 describes aryl piperazine derivatives useful as modulators of dopamine and serotonin receptors. WO2003/028728 reports certain substituted piperazinyl butyl carboxamides useful as dopamine D3 selective ligands.

Leopoldo et al. (J. Med. Chem., 2002; 45: 5727-5735) describe a structure-affinity relationship study on certain N-[4-(4-arylpiperazin-1-yl)butyl]arylcarboxamides, useful as potent and selective dopamine D3 receptor ligands. Campiani et al. (J. Med. Chem., 2003; 46: 3822-3839) describe the synthesis and pharmacological evaluation of certain potent and highly selective D3 receptor ligands. Hackling et al. (J. Med. Chem., 2003; 46: 3883-3899) describe a series of N-(omega-(4-(2-methoxyphenyl)piperazin-1-yl)alkyl) carboxamides as dopamine D2 and D3 receptor ligands.

WO2004/112729 and WO2004/033426 and EP409048 claim certain aryl piperazine and aryl piperidine derivatives having activity at the dopamine D2 receptor subtypes.

WO96/02246, WO2006/058993 and WO2004/004729 describe certain aryl piperazine and aryl piperidine derivatives having activity at dopamine D3 receptor subtypes. WO2004/024878 describes dopamine D3 receptor selective ligands.

U.S. Pat. No. 4,803,203 claims certain heterocyclic piperazinyl alkoxy-benzoheterocyclic derivatives useful as antipsychotic agents.

U.S. Pat. No. 6,100,255 claims aryl piperazine derivatives having activity at dopamine D4 receptor subtypes. WO94/22839 describes benzimidazole derivatives having affinity for the dopamine D4 receptor subtype. WO2001/49677 describes certain indolylpiperazine derivatives having activity at the dopamine D4 receptor subtypes.

Leopoldo et al. (J. Med. Chem., 2006; 49: 358-365) describes the design, synthesis, and binding affinities of potential PET ligands for visualization of brain dopamine D3 receptors.

CN103073524A describes certain substituted phenylpiperazin-1-yl-butyl carbamate derivatives and claims their affinity for the D3 receptor. The compounds described therein displayed moderate to low D3 receptor binding affinities (Ki,nM) as shown by the table at page 23 of CN103073524A.

A substantial amount of knowledge has accumulated over the years since the discovery of fatty acid amide hydrolase, and several classes of compounds have been claimed in a number of patents and patent applications. The class of O-arylcarbamate FAAH inhibitors is well known in the art; U.S. Pat. No. 7,176,201 claims a series of biphenyl esters of alkylcarbamic acid. U.S. Pat. No. 8,003,693 claims naphthyl esters of alkylcarbamic acid. WO2008/020866 discloses esters of alkylcarbamic acid of formula (1) and (2)

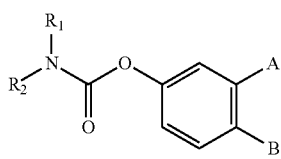

(1)

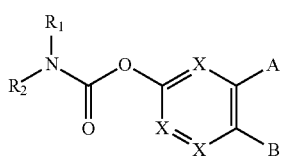

(2)

wherein $R_1$ and $R_2$ are optionally substituted alkyl or cycloalkyl groups, while A and B represent several different substituents.

WO2008/063714 claims FAAH inhibitors of structures of formula (3), (4) and (5)

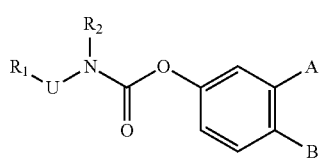

(3)

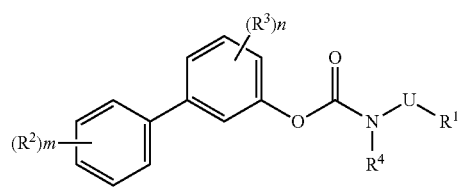

(4)

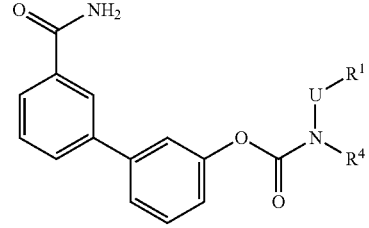

(5)

wherein $R_1$ is selected from a group consisting of optionally substituted saturated cycloalkyl groups, U is a bond or methylene group and $R_2$ is independently H or a saturated alkyl group. A and B, when considered independently from each other, represent an array of several different substituents or, when taken together with the aromatic ring they are bound to, they represent an aromatic or non-aromatic carbocycle or heterocycle.

Other carbamate-based FAAH inhibitors were disclosed in WO2010/105930 with the general structure of formula (6)

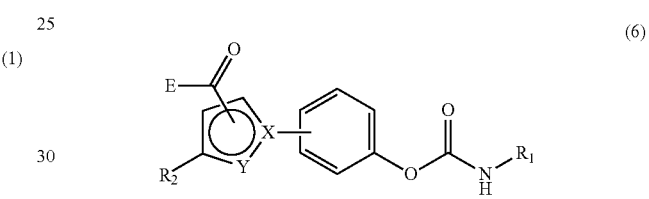

(6)

wherein $R_1$ is H or a $(C_1-C_4)$-alkyl, or a $(C_3-C_6)$-cycloalkyl, or $(C_1-C_6)$-alkyl-aryl, or $(C_1-C_6)$-alkyl-$(C_2-C_5)$-alkynyl; and the aromatic ring is mono-substituted with several heteroaryl moieties encompassing differently substituted 5-membered heterocyclic groups;

WO2008/129129 discloses some esters of alkyl carbamic acids of general structure of formula (7)

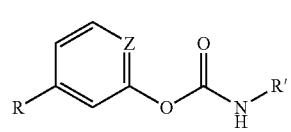

(7)

wherein R' is selected from the group consisting of H, substituted or unsubstituted alkyl of 1 to 24 carbon atoms, substituted or unsubstituted cycloalkyl, substituted or unsubstituted heteroalkyl, substituted or unsubstituted aryl, and substituted or unsubstituted heteroaryl; Z is either N or CH, and R represents several heterocyclyl or heterocyclic carbonyl moiety differently substituted.

At the best of our knowledge, there is no prior art describing any compound as a multi target modulator, capable to inhibit the FAAH enzyme and to modulate the D3 dopamine receptor at the same time.

SUMMARY OF THE INVENTION

The inventors have found that specific compounds bearing an O-phenyl carbamate properly connected through a suitable spacer to an aryl piperazine or aryl piperidine ring are able to simultaneously inhibit the FAAH enzyme and modulate the D3 dopamine receptor, and are therefore useful in the treatment of syndromes which would clinically benefit from the inhibition of the FAAH enzyme and the modulation of the D3 dopamine receptor activities.

In a first aspect, the present invention provides a compound of Formula (I) or a pharmaceutically acceptable salt thereof

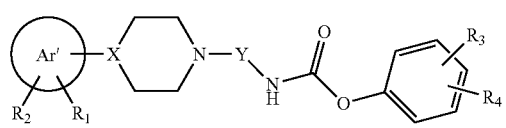
(I)

Wherein Ar', $R_1$, $R_2$, $R_3$, $R_4$, X, Y are as defined below.

In a second aspect, the present invention provides a pharmaceutical composition comprising one or more compounds of Formula I, as defined above or a pharmaceutically acceptable salt thereof, and pharmaceutically acceptable excipients, carriers or diluents.

In a third aspect, the present invention provides a method for modulating the levels of D3 dopamine receptors activity and fatty acid N-acyl ethanolamides (FAEs) in a subject by administering a composition according to the invention. In some embodiments, the present invention provides methods for treating conditions associated to an unbalanced activity of D3 dopamine receptors and which benefit from increased levels of AEA, OEA and PEA, including nicotine and other drugs of abuse dependence and addiction, by administering a therapeutically effective amount of a compound of Formula I, as defined above or a pharmaceutically acceptable salt thereof, according to the invention.

In a fourth aspect, the present invention provides methods for preparing the compounds of Formula I, as defined above, through a process consisting of suitable synthetic transformations.

DETAILED DESCRIPTION OF THE INVENTION

In a first aspect, the present invention provides a compound of Formula (I) or a pharmaceutically acceptable salt thereof

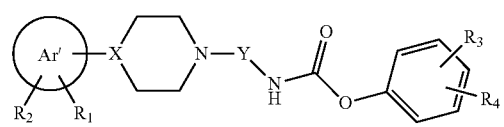
(I)

Wherein:

Ar' is a 5- to 10-membered aromatic or heteroaromatic single or fused ring comprising up to 3 heteroatoms selected from N, O, S;

$R_1$ and $R_2$ are independently selected from the group consisting of hydrogen, halogen (preferably F or Cl), linear or branched $C_{1-6}$alkyl (preferably Me), $C_{1-6}$alkoxy (preferably OMe), OH, $CF_3$; $R_1$ and $R_2$ can be attached in any position of the Ar' group;

X is N or CH;

Y is an alkylene or alkenylene group selected from the group consisting of

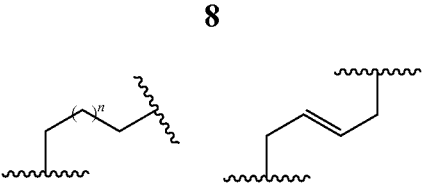

where n is 0 or an integer from 1 to 3 and wherein Y is optionally substituted by up to two same or different substituents B attached to any position of the Y group and selected in the group consisting of F, OH, $CH_2OH$, $CH_2F$; preferably n is an integer from 1 to 2;

$R_3$ is a 5- to 6-membered aromatic or heteroaromatic ring, a benzyl or benzoyl group, optionally substituted by up to two same or different substituents $R_5$ attached to any position of the $R_3$ ring, wherein $R_5$ is selected from OH, $NH_2$, CN, halogen (preferably F or Cl), linear or branched $C_{1-6}$alkyl (preferably Me), $C_{1-6}$alkoxy (preferably OMe), hydroxy $C_{1-6}$alkyl (preferably $CH_2OH$), $SO_2NH_2$, $CONH_2$, $CONR_7R_8$, where $R_7$ and $R_8$ are, independently, hydrogen or $C_{1-6}$alkyl (preferably Me);

or $R_3$ is a 5- to 7-membered aliphatic or heterocyclic ring comprising up to 3 heteroatoms selected from N, O, S optionally substituted by up to two same or different substituents $R_6$ attached to any position of the $R_3$ ring, wherein $R_6$ is selected from F, gem-difluoro, Me, gem-dimethyl, =O, COMe, OH, $CONH_2$;

and wherein the group $R_3$ can be attached to any position of the phenyl ring;

$R_4$ is hydrogen, halogen (preferably F or Cl), linear or branched $C_{1-6}$alkyl (preferably Me), $C_{1-6}$ alkoxy (preferably OMe), hydroxy$C_{1-6}$alkyl (preferably $CH_2OH$), $CF_3$; the group $R_4$ can be attached to any position of the phenyl ring;

or $R_3$ and $R_4$ together with the phenyl ring to which they are connected may form a 9H-carbazole ring.

All technical and scientific terms used herein have the same meaning as commonly understood by a person of ordinary skill in the art, unless otherwise defined. The following terms, used in the specification and claims of this application, have the meaning specified hereunder, unless otherwise defined.

The term "alkyl", as used herein, indicates a saturated aliphatic hydrocarbon radical, including straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, and the like.

The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, and the like.

The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, 1- or 2-butynyl, and the like.

The term "cycloalkyl", as used herein, indicates a 3- to 7-membered all-carbon monocyclic ring, which may contain one or more double bonds but does not have a completely conjugated pi-electron system. Examples of cycloalkyl groups include, without limitation, cyclopropane, cyclobutane, cyclopentane, cyclopentene, cyclohexane, cyclohexene, cyclohexadiene, and cycloheptane.

The term "aryl", as used herein, indicates a hydrocarbon consisting of a mono-, bi- or tricyclic ring system, wherein the rings are fused together or linked to each other covalently and at least one of the carbocyclic ring is aromatic. The term "aryl" means a cyclic aromatic such as a 6-membered hydrocarbon, a two six-membered fused hydrocarbon, and a two six-membered hydrocarbon covalently bonded. Examples of aryl groups include phenyl, alpha- or beta-naphthyl, 9,10-dihydroanthracenyl, indanyl, fluorenyl, biphenyl and the like.

The term "heteroaryl", as used herein, indicates a mono-, bi- or tricyclic ring system containing from one to four heteroatoms selected from nitrogen, oxygen and sulphur, wherein the rings are fused together or linked to each other covalently and at least one of the rings is aromatic. Examples of heteroaryl groups include pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl.

The terms "heterocyclyl" or "heterocyclic ring", as used herein mean a 3- to 7-membered, saturated or partially unsaturated carbocyclic ring wherein one or more carbon atoms are independently replaced by nitrogen, oxygen or sulfur. The heteroatom nitrogen and sulfur are optionally oxidized, and the nitrogen atom(s) are optionally quaternized. Examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, hexamethyleneimine, homopiperazine, and the like.

The term "aromatic" refers to a moiety wherein the constituent atoms make up an unsaturated ring system, all atoms in the ring system are $sp^2$ hybridized and the total number of pi electrons is equal to 4n+2, wherein n is an integer.

Any of the above mentioned alkyl, alkenyl, alkynyl, cycloalkyl, aryl, heteroaryl, heterocyclyl or heterocyclic ring group may be unsubstituted or substituted by one or more substituents.

Unless otherwise indicated, the term "substituted" as used herein means that one or more hydrogen atoms of the above mentioned groups are replaced with another atom or functional group including, by way of example, alkyl, substituted alkyl, aryl, substituted aryl, arylalkyl, alkoxy, cycloalkyloxy, aryloxy, arylalkyloxy, hydroxy, heteroaryl, heteroaryloxy, heterocyclyloxy, trifluoromethyl, trifluoromethoxy, carboxy, acyl, aroyl, heteroaroyl, halogen, nitro, cyano, alkoxycarbonyl, aryloxycarbonyl, aralkyloxycarbonyl, cycloalkyloxycarbonyl, heteroaryloxycarbonyl, acyloxy, alkylthio, arylthio, alkylsulfinyl, arylsulfinyl, alkylsulfonyl, arylsulfonyl, —O-aroyl, —O-heteroaroyl, oxo (=O), —C(=O)NR$^h$R$^k$, and NR$^p$R$^q$, wherein each of R$^h$, R$^k$, R$^p$, and R$^q$ independently represents hydrogen, unsubstituted or substituted alkyl, unsubstituted or substituted cycloalkyl, unsubstituted or substituted aryl, unsubstituted or substituted arylalkyl, unsubstituted or substituted heteroaryl, unsubstituted or substituted heterocyclyl, acyl, aroyl, heteroaroyl, and when R$^h$ and R$^k$, or R$^p$ and R$^q$ are taken together with the nitrogen atom to which they are bound, the group NR$^h$R$^k$ or the group NR$^p$R$^q$ represent a heterocyclyl residue and wherein the terms alkyl, cycloalkyl, aryl, heteroaryl, heterocyclyl are as above defined.

In embodiment, the invention relates to compounds of formula (I) wherein:

Ar' is a benzene, indole, naphthyl or pyridine ring;

$R_1$ and $R_2$ are, independently, hydrogen, halogen (preferably Cl or F) or $C_{1-6}$ alkoxy (preferably OMe), $C_{1-6}$alkyl (preferably Me), $CF_3$;

X is N or CH;

Y is $CH_2$—$(CH_2)_n$—$CH_2$, where n is 0 or an integer from 1 to 2 or a group $CH_2$—CH=CH—$CH_2$, and wherein Y is optionally substituted by up to two same or different substituents B attached to any position of the Y group and selected in the group consisting of F, OH, $CH_2OH$, $CH_2F$;

$R_3$ is a phenyl, benzyl, benzoyl or a pyridine ring attached to the phenyl ring in the meta or para position and optionally substituted by up to two same or different substituents $R_5$, wherein $R_5$ is halogen (preferably F), $C_{1-6}$alkyl (preferably Me) or a group $CONH_2$ or $CONHCH_3$ attached to $R_3$ in the meta or para position;

or $R_3$ is a 5- to 7-membered heterocyclic ring comprising up to 2 heteroatoms, preferably 1-pyrrolidinyl or 1-piperidinyl or 1-piperazinyl or 4-morpholinyl, attached to the phenyl ring in the meta or para position and optionally substituted by up to two same or different substituents $R_6$, wherein $R_6$ is gem-difluoro, gem-dimethyl, COMe, attached to $R_3$ in any position of the ring;

$R_4$ is hydrogen, halogen (preferably F), $C_{1-6}$alkyl (preferably Me), $C_{1-6}$alkoxy (preferably OMe), $CF_3$; the group $R_4$ can be attached to the phenyl ring in any position of the ring;

or $R_3$ and $R_4$ together with the phenyl ring to which they are connected may form a 9H-carbazole ring.

Preferred compounds according to this embodiment are those in which:

Ar' is a benzene ring;

$R_1$ and $R_2$ are, independently, H, Cl, OMe, Me, or $CF_3$;

X is N or CH;

Y is $CH_2$—$(CH_2)_n$—$CH_2$, where n is 0 or an integer from 1 to 2, a group $CH_2$—CH=CH—$CH_2$, a group $CH(CH_2F)CH_2$, or a group $CH_2CH(F)CH_2CH_2$;

$R_3$ is a phenyl, benzyl, benzoyl or pyridine ring attached to the phenyl ring in the meta or para position and optionally substituted with a group $CONH_2$ or $CONHCH_3$ attached to $R_3$ in the meta or para position;

or $R_3$ is a 1-piperidinyl or 1-piperazinyl or 4-morpholinyl ring attached to the phenyl ring in the meta or para position and optionally substituted with gem-difluoro;

$R_4$ is hydrogen, F, Me or OMe; the group $R_4$ can be attached to the phenyl ring in any position of the ring;

or $R_3$ and $R_4$ together with the phenyl ring to which they are connected may form a 9H-carbazole ring.

Examples of the compounds of the invention are:

[3-(3-carbamoylphenyl)phenyl] N-[4-[4-(2-methoxyphenyl)piperazin-1-yl]butyl] carbamate;

[3-(3-carbamoylphenyl)phenyl] N-[4-[4-(2,3-dichlorophenyl)piperazin-1-yl]butyl] carbamate;

[3-(3-carbamoylphenyl)phenyl] N-[3-[4-(2,3-dichlorophenyl)piperazin-1-yl]propyl] carbamate;

[3-(3-carbamoylphenyl)phenyl] N-[3-(4-phenylpiperazin-1-yl)propyl] carbamate;

(3-phenylphenyl) N-[3-(4-phenylpiperazin-1-yl)propyl] carbamate;

[4-(3-carbamoylphenyl)phenyl] N-[3-[4-(2,3-dichlorophenyl)piperazin-1-yl]propyl] carbamate;

[4-(3-carbamoylphenyl)phenyl] N-[4-[4-(2,3-dichlorophenyl)piperazin-1-yl]butyl] carbamate;
(3-morpholinophenyl) N-[4-[4-(2,3-dichlorophenyl)piperazin-1-yl]butyl] carbamate hydrochloride;
[3-(4,4-difluoro-1-piperidinyl)phenyl] N-[4-[4-(2,3-dichlorophenyl)piperazin-1-yl]butyl] carbamate hydrochloride;
[4-(3-carbamoylphenyl)phenyl] N-[4-[4-(2-methoxyphenyl)piperazin-1-yl]butyl] carbamate;
[4-(3-carbamoylphenyl)phenyl] N-[3-[4-(2-methoxyphenyl)piperazin-1-yl]propyl] carbamate;
[4-(4,4-difluoro-1-piperidinyl)phenyl] N-[4-[4-(2,3-dichlorophenyl)piperazin-1-yl]butyl] carbamate hydrochloride;
(3-morpholinophenyl) N-[3-[4-(o-tolyl)piperazin-1-yl]propyl] carbamate hydrochloride;
[3-(3-carbamoylphenyl)phenyl] N-[4-(4-phenyl-1-piperidinyl)butyl] carbamate hydrochloride;
(4-phenylphenyl) N-[3-[4-(o-tolyl)piperazin-1-yl]propyl] carbamate;
(4-phenylphenyl) N-[3-[4-[2-(trifluoromethyl)phenyl]piperazin-1-yl]propyl] carbamate;
9H-carbazol-2-yl N-[3-[4-(2,3-dichlorophenyl)piperazin-1-yl]propyl]carbamate;
[4-(4,4-difluoro-1-piperidinyl)phenyl] N-[3-[4-[2-(trifluoromethyl)phenyl] piperazin-1-yl]propyl] carbamate hydrochloride;
[4-(3-carbamoylphenyl)phenyl] N-[(E)-4-[4-(2,3-dichlorophenyl)piperazin-1-yl]but-2-enyl] carbamate;
[4-(3-carbamoylphenyl)-3-fluoro-phenyl] N-[(E)-4-[4-(2,3-dichlorophenyl) piperazin-1-yl]but-2-enyl] carbamate;
[4-(3-carbamoylphenyl)-3-fluoro-phenyl] N-[4-[4-(2,3-dichlorophenyl)piperazin-1-yl]butyl] carbamate;
[4-(3-carbamoylphenyl)phenyl] N-[4-[4-[2-(trifluoromethyl)phenyl]piperazin-1-yl]butyl] carbamate;
[3-(3-carbamoylphenyl)phenyl] N-[3-[4-(2-methoxyphenyl)piperazin-1-yl]propyl] carbamate;
[4-(2-pyridyl)phenyl] N-[4-[4-(2,3-dichlorophenyl)piperazin-1-yl]butyl] carbamate;
[4-(3-carbamoylphenyl)phenyl] N-[4-(4-phenylpiperazin-1-yl)butyl] carbamate;
(3-phenylphenyl) N-[4-[4-(2,3-dichlorophenyl)piperazin-1-yl]butyl] carbamate hydrochloride;
(4-phenylphenyl) N-[4-[4-(2, 3-dichlorophenyl)piperazin-1-yl]butyl] carbamate;
9H-carbazol-2-yl N-[4-[4-(2,3-dichlorophenyl)piperazin-1-yl]butyl] carbamate;
(4-phenylphenyl) N-[4-[4-(o-tolyl)piperazin-1-yl]butyl] carbamate;
(4-phenylphenyl) N-[4-[4-[2-(trifluoromethyl)phenyl]piperazin-1-yl]butyl] carbamate;
(4-phenylphenyl) N-[3-[4-(2-methoxy phenyl)piperazin-1-yl]propyl] carbamate hydrochloride;
(4-phenylphenyl) N-[4-[4-(2-methoxyphenyl)piperazin-1-yl]butyl] carbamate hydrochloride;
9H-carbazol-2-yl N-[4-[4-(2-methoxyphenyl)piperazin-1-yl]butyl] carbamate;
[4-(3-carbamoylphenyl)-3-methoxy-phenyl] N-[4-[4-(2-methoxyphenyl)piperazin-1-yl]butyl] carbamate;
(4-phenylphenyl) N-[3-fluoro-4-[4-(2-methoxyphenyl)piperazin-1-yl]butyl] carbamate hydrochloride;
(4-phenylphenyl) N-[4-[4-(2, 3-dichlorophenyl)piperazin-1-yl]-3-fluoro-butyl] carbamate;
(3-methoxy-4-phenyl-phenyl) N-[3-[4-(2-methoxyphenyl)piperazin-1-yl]propyl] carbamate hydrochloride;
(3-methoxy-4-phenyl-phenyl) N-[4-[4-(2-methoxyphenyl)piperazin-1-yl]butyl] carbamate;
[4-(3-carbamoylphenyl)phenyl] N-[4-[4-(o-tolyl)piperazin-1-yl]butyl] carbamate;
[4-(3-carbamoylphenyl)-3-methoxy-phenyl] N-[4-[4-(2,3-dichlorophenyl)piperazin-1-yl]butyl] carbamate;
(4-phenylphenyl) N-[2-[4-(2,3-dichlorophenyl)piperazin-1-yl]-3-fluoro-propyl] carbamate hydrochloride;
(4-benzylphenyl) N-[4-[4-(2-methoxy phenyl)piperazin-1-yl]butyl] carbamate hydrochloride;
(4-benzyl phenyl) N-[3-[4-(2-methoxyphenyl)piperazin-1-yl]propyl] carbamate hydrochloride;
(4-benzoylphenyl) N-[3-[4-(2-methoxyphenyl)piperazin-1-yl]propyl] carbamate hydrochloride;
(4-benzoylphenyl) N-[4-[4-(2-methoxyphenyl)piperazin-1-yl]butyl] carbamate hydrochloride.

The present invention also provides methods for preparing the compounds of Formula (I), as defined above, through a process consisting of suitable synthetic transformations reported, for instance, in Michael Smith, Jerry March—*March's Advanced Organic Chemistry: reactions mechanisms and structure*—6th Edition, John Wiley & Sons Inc., 2007, which is herein incorporated as reference. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—*Protective Groups in Organic Synthesis*, Fourth Edition, John Wiley & Sons Inc., 2006, which is herein incorporated as reference.

In one embodiment, a compound of Formula (I) can be obtained by application of the chemical transformations reported in the schemes herein described.

Synthesis of Compounds of Formula I

Final compounds of Formula I can be prepared according to Scheme Ia.

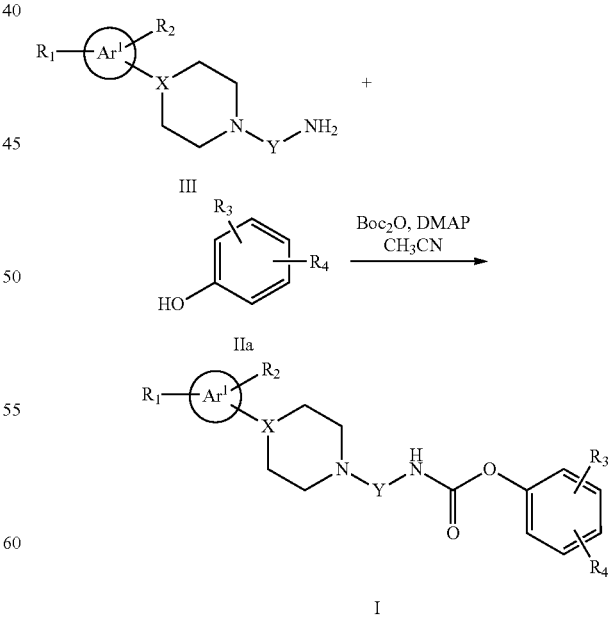

The final compounds of Formula (I) can be synthesized upon activation of the amines of Formula III as isocyanates, by reaction with Boc anhydride and 4-dimethylamino pyridine in acetonitrile, followed by reaction with the appropriate alcohol IIa (*Tet. Lett.*, 1996; 4039(33): 5861-5864).

Alternatively, amines of Formula III can be activated as carbamates by reaction with para-nitrophenyl chloroformate and diisopropylamine in dichloromethane.

Another synthetic procedure can go through the conversion of alcohol of Formula IIa into chloroformates by means of treatment with triphosgene and diisopropylamine in dichloromethane, followed by reaction with amines III.

Synthesis of Compounds of Formula II

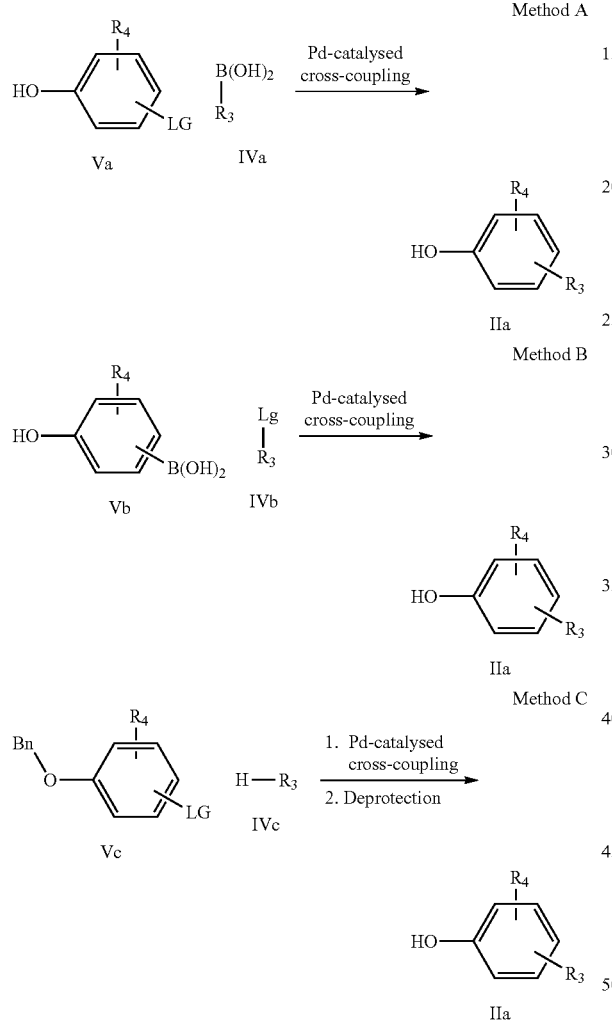

According to Scheme II (Method A and B), the intermediates IIa can be prepared via palladium catalyzed cross-coupling of commercially available aryl/heteroaryl boronic acids with aryl/heteroaryl derivatives containing appropriate leaving groups (LG). For example halo phenols Va can react with aryl boronic acids IVa in the presence of catalytic Palladium acetate in a medium of water and ethylene glycol monomethyl ether, following the methodology developed by Del Zotto et al. (*Eur. J. Org. Chem.*, 2009; (1): 110-116). Compounds IIa can be isolated upon filtration of the catalyst from the reaction mixture and chromatographic purification of the reaction crude.

When $R_3$ is a 5-7 membered nitrogen-containing heterocyclic ring comprising up to 3 heteroatoms, intermediates IIa can be prepared according to Scheme II (Method C), by reaction of benzyloxy substituted aryl derivatives containing appropriate leaving groups (LG) with commercially available heterocyclic compounds IVc in the presence of a Palladium complex as described by Buchwald and co-workers (*Nature protocols*, 2007; 2(11): 2881-7), followed by removal of the benzyl group.

Synthesis of Compounds of Formula III

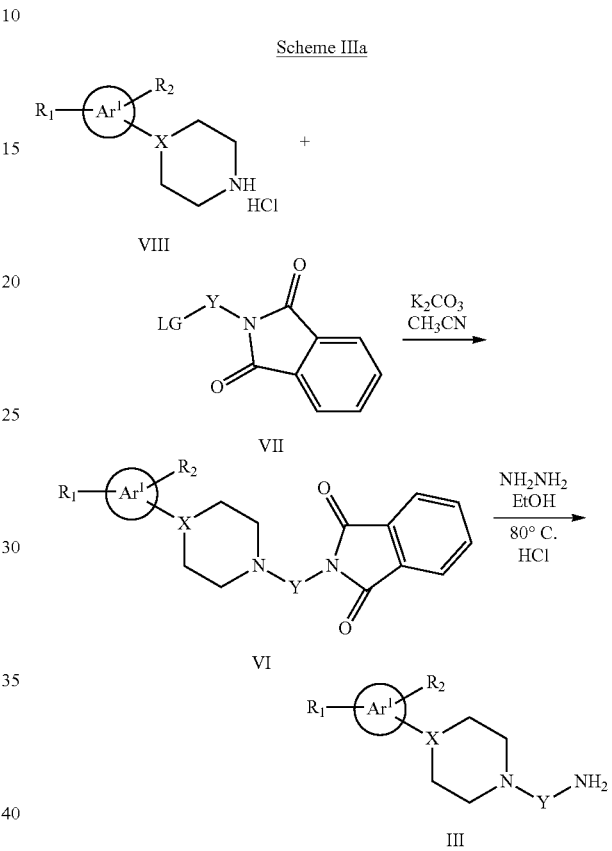

According to Scheme IIIa, amines of general Formula III can be synthesized starting from commercially available aryl substituted nitrogen-containing heterocycles of general Formula VIII by treatment with the appropriate commercially available phthalimides VII in the presence of potassium carbonate and acetonitrile under reflux. The so obtained phthalimides VI are then converted into primary amines by reflux in alcoholic hydrazine. Upon acidification and separation of the insoluble 2,3-dihydrophthalazine-1,4-dione, the desired amines can be isolated by neutralization with sodium hydroxide and extraction with organic solvents (e.g. ethyl acetate or dichloromethane).

When Y is substituted by B, amines of general Formula III can be synthesised following the Scheme IIIB. Intermediates XI were synthesized starting from commercially available epoxides derivatives XII upon reflux with phthalimide under basic condition in DMF; intermediates XI were isolated by extraction with organic solvents (DCM or Ethyl acetate). The so obtained intermediate XI were reacted with commercially available aryl substituted nitrogen-containing heterocycles of general Formula VIII under heating in i-PrOH, affording intermediate X. Microwave-assisted procedures were also developed for the synthesis of these compounds; the pure intermediates were obtained by filtration of the reaction mixture. The fluorination of the hydroxyl group can be achieved with commercially available fluorinating agents (e.g. DAST, DeOxo-Fluor®, Xtal Fluor-E®) neat or in apolar solvents (DCM or Chloroform). While not being bound to any theory, formation of the fluorinated compounds of formula IX may occur as proposed by Ji-Wang Chem et al, Tetrahedron Letters, 1998, 39: 8483-8486, i.e. through an initial nucleophilic attack of the hydroxy group of compounds of formula X on the sulphur atom of the fluorinating agent to form an —$OSF_2NEt_2$ species in the case of DAST or XTal Fluor-E®, or an —$OSF_2N(CH_2CH_2OCH_3)_2$ species in the case of DeOxo-Fluor®, which is followed by intermolecular displacement of said species through anchimeric participation of the piperazine moiety to form a spiro aziridinium intermediate. Ring opening of the latter by a fluoride anion either through the less hindered or the more hindered carbon would result in the formation of IX wherein B is $CH_2F$ or F, respectively. The deprotection of the phthalimide protecting group was accomplished as already described in Scheme IIIa.

It will be understood that, as used herein, references to the compounds of Formula (I) are meant to include also the pharmaceutically acceptable salts or derivatives thereof.

Furthermore, the compounds of Formula (I) may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula (I)" refer to each of the compounds of Formula (I) and are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation.

Suitably physiologically or pharmaceutically acceptable salts of the compounds of the present invention include the

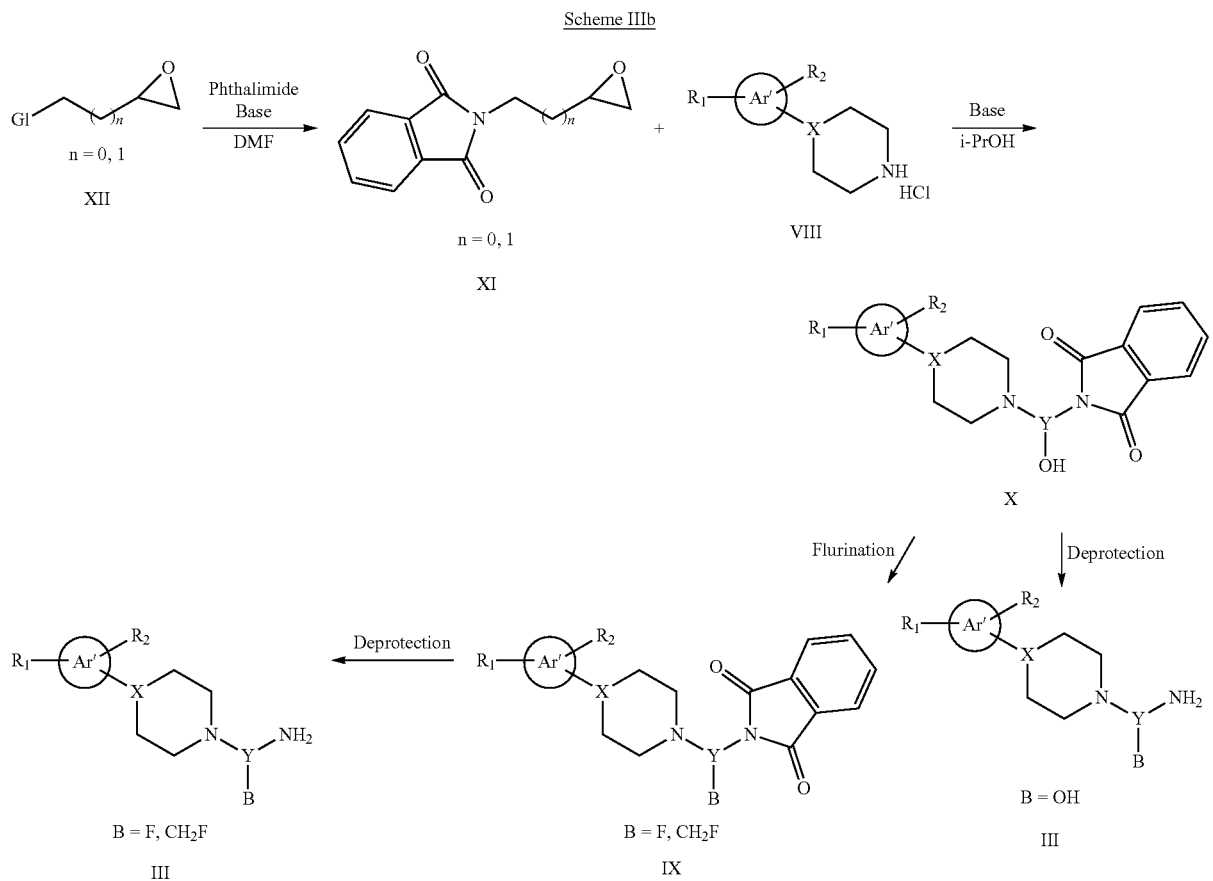

Scheme IIIb

Commercially available starting materials IIb-c, IVa-c, Va-b, VII, VIII and XII can be purchased from specialized vendors such as Sigma-Aldrich, Alfa Aesar and others, or prepared according to standard synthetic procedures as described, for instance, in Michael Smith, Jerry March—*March's Advanced Organic Chemistry: reactions mechanisms and structure*—6th Edition, John Wiley & Sons Inc., 2007, which is herein incorporated as reference.

hydrochloride, acetate, citrate, gluconate, lactate, tartrate, phosphate, borate, maleate, sulphate and nitrate, the hydrochloride being preferred.

The salts of compounds of Formula (I) may be prepared by reacting a basic compound with the desired acid in solution.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds (I) may be in crystalline form. In certain embodiments, the crystalline forms of the compounds (I) are polymorphs.

The subject invention also includes isotopically-labelled compounds, which are identical to those recited in Formula (I) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, phosphorous, sulfur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e. $^3H$, and carbon-14, i.e. $^{14}C$, u isotopes are particularly preferred for their ease of preparation and detectability. $^{11}C$ and $^{18}F$ isotopes are particularly useful in PET (Positron Emission Tomography), and $^{125}I$ isotopes are particularly useful in SPECT (Single Photon Emission Computerized Tomography), all useful in brain imaging. Further, substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. Isotopically-labelled compounds of Formula (I) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I) may have asymmetric carbon atoms or axial asymmetries in some cases and, correspondingly, it may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist. Prodrugs or compounds which are stable ex vivo and which are convertible in the mammalian (e.g. human) body to the inventive compounds are, however, included.

The present invention also encompasses active metabolites of compounds of Formula (I).

Another aspect of the present invention relates to pharmaceutical compositions containing a compound of Formula (I).

The pharmaceutical compositions of the present invention encompass any compositions made by admixing a compound of the present invention and a pharmaceutically acceptable carrier. Such compositions are suitable for pharmaceutical use in an animal or human.

The pharmaceutical compositions of the present invention comprise a therapeutically effective amount of one or more compounds of Formula (I) or a pharmaceutically acceptable salt thereof, and a pharmaceutically acceptable carrier.

A pharmaceutical composition may optionally contain other active ingredients. The term "carrier" refers to a vehicle, excipient, diluents, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g. oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents, and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for parenteral, including subcutaneous, intramuscular, and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous, or pulmonary, in the form of nasal or buccal inhalation, administration. The compositions may be prepared by any of the methods well-known in the art of pharmacy.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

With respect to formulations with respect to any variety of routes of administration, methods and formulations for the administration of drugs are disclosed in *Remington's Pharmaceutical Sciences*, 17$^{th}$ Edition, Gennaro et al. Eds., Mack Publishing Co., 1985, and *Remington's Pharmaceutical Sciences*, Gennaro A R ed. 20$^{th}$ Edition, 2000, Williams & Wilkins PA, USA, and *Remington: The Science and Practice of Pharmacy*, 21$^{st}$ Edition, Lippincott Williams & Wilkins Eds., 2005; and in Ansel's *Pharmaceutical Dosage Forms and Drug Delivery Systems*, 8$^{th}$ Edition, Lippincott Williams & Wilkins Eds., 2005, which are herein incorporated as reference.

A further aspect of the present invention relates to compounds of Formula (I) for use in a method for modulating the levels of D3 dopamine receptors activity and fatty acid N-acyl ethanolamides (FAEs) in a subject by administering a composition according to the invention. In some embodiments, the present invention provides compounds (I) for use in a method for treating conditions associated to an unbalanced activity of D3 dopamine receptors and which benefit from an increased levels of arachidonoylethanolamide (AEA) and/or oleoylethanolamide (OEA) and/or palmitoylethanolamide (PEA), by administering a therapeutically effective amount of a compound of Formula (I) as defined above or a pharmaceutically acceptable salt thereof, according to the invention.

In one embodiment, the present invention provides compounds of Formula (I) for use in a method for effecting smoking cessation in a mammal, said method comprising administering a therapeutically effective amount of a compound of Formula (I) to the mammal.

In another embodiment, the present invention provides compounds of Formula (I) for use in a method for reducing tobacco use in a mammal, said method comprising administering a therapeutically effective amount of a compound of Formula (I) to the mammal.

In another embodiment, the present invention provides compounds of Formula (I) for use in a method for treating or preventing syndromes associated to cannabis use disorders, including cannabis craving and addiction, cannabis dependence, cannabis withdrawal, cocaine use disorders, including cocaine craving and addiction, cocaine dependence, cocaine withdrawal, opioid use disorders, including opioid craving and addiction, opioid dependence, opioid withdrawal, opiate use disorders, including opiate craving and addiction, opiate dependence, opiate withdrawal, amphetamine use disorders, including amphetamine craving and addiction, amphetamine dependence, amphetamine withdrawal, methamphetamine use disorders, including methamphetamine craving and addiction, methamphetamine dependence, methamphetamine withdrawal, alcohol use disorders, including alcohol craving and addiction, alcohol dependence, alcohol withdrawal, and alcohol induced delirium in a mammal, said method comprising administering a therapeutically effective amount of a compound of Formula (I) to the mammal.

In another embodiment, the present invention provides compounds of Formula (I) for use in a method of modulating appetite or body weight or both in a mammal, said method comprising administering a therapeutically effective amount of a compound of Formula (I) to the mammal.

In another embodiment, the present invention provides compounds of Formula (I) for use in a method of preventing or treating eating disorders, including bulimia nervosa, anorexia nervosa, binge eating disorder, eating disorder not otherwise specified (EDNOS) in a mammal, said method comprising administering a therapeutically effective amount of a compound of Formula (I) to the mammal.

In another embodiment, the present invention provides compounds of Formula (I) for use in a method of preventing or treating anxiety in a mammal, said method comprising administering a therapeutically effective amount of a compound of Formula (I) to the mammal.

In another embodiment, the present invention provides compounds of Formula (I) for use in a method of preventing or treating post-traumatic stress disorder in a mammal, said method comprising administering a therapeutically effective amount of a compound of Formula (I) to the mammal.

In another embodiment, the present invention provides compounds of Formula (I) for use in a method of preventing or treating schizophrenia in a mammal, said method comprising administering a therapeutically effective amount of a compound of Formula (I) to the mammal.

In another embodiment, the present invention provides compounds of Formula (I) for use in a method of preventing or treating mood disorders, including bipolar disorder type I, bipolar disorder type II, cyclothymia, substance-induced mood disorder, depression, atypical depression, psychotic major depression, post-partum depression, dysthymia, catatonic depression, melancholic depression, depressive disorder not otherwise specified (DDNOS) in a mammal, said method comprising administering a therapeutically effective amount of a compound of Formula (I) to the mammal.

In another embodiment, the present invention provides compounds of Formula (I) for use in a method of preventing or treating pathological behaviours, including compulsive gambling, compulsive shopping, compulsive hoarding, and kleptomania in a mammal, said method comprising administering a therapeutically effective amount of a compound of Formula (I) to the mammal.

PREPARATIVE EXAMPLES

Abbreviations used in the description of the Examples that follow are:

Acetonitrile (MeCN); ammonium chloride ($NH_4Cl$); BnBr (benzyl bromide); carbonyldiimidazole (CDI); cesium carbonate ($Cs_2CO_3$); cyclohexane (Cy); chloroform ($CHCl_3$); deuterated chloroform ($CDCl_3$ or Chloroform-d); deuterated dimethylsulfoxide (DMSO-$d_6$); dichloromethane (DCM); dimethylsulfoxide (DMSO); N,N-diisopropylethylamine (DIPEA); 4-(dimethylamino)-pyridine (DMAP); ethylene glycol monomethyl ether (EGME); ethanol (EtOH); electrospray (ES); ethyl acetate (EtOAc); hydrochloric acid (HCl); mass spectrometry (MS); microwave (MW); sulfuric acid ($H_2SO_4$); iodomethane (MeI); N,N-dimethylformamide (DMF); lithium hydroxide (LiOH); magnesium sulphate ($MgSO_4$); methanol (MeOH); nuclear magnetic resonance (NMR); room temperature (RT); sodium bicarbonate ($NaHCO_3$); tetrabutylammonium iodide (TBAI); triethylsilane (TES); tetrahydrofuran (THF); thin layer chromatography (TLC); triethylamine ($Et_3N$); trifluoroacetic acid (TFA).

Automated column chromatography purifications were done using a Teledyne ISCO apparatus (CombiFlash™ Rf) with pre-packed silica gel columns of different sizes (from 4 g until 120 g). Mixtures of increasing polarity of cyclohexane and ethyl acetate or dichloromethane and methanol were used as eluents. Preparative TLC were performed using Macherey-Nagel pre-coated 0.05 mm TLC plates (SIL G-50 $UV_{254}$). Hydrogenation reactions were performed using H-Cube™ continuous hydrogenation equipment (SS-reaction line version), employing disposable catalyst cartridges (CatCart™) preloaded with the required heterogeneous catalyst. Microwave heating was performed using Explorer™-48 positions instrument (CEM). NMR experiments were run on a Bruker Avance III 400 system (400.13 MHz for $^1$H, and 100.62 MHz for $^{13}$C), equipped with a BBI probe and Z-gradients. Spectra were acquired at 300 K, using deuterated dimethylsulfoxide (DMSO-$d_6$) or deuterated chloroform ($CDCl_3$) as solvents. Chemical shifts for $^1$H and $^{13}$C spectra were recorded in parts per million using the residual non-deuterated solvent as the internal standard (for $CDCl_3$: 7.26 ppm, $^1$H and 77.16 ppm, $^{13}$C; for DMSO-d6: 2.50 ppm, $^1$H; 39.52 ppm, $^{13}$C).

UPLC/MS analyses were run on a Waters ACQUITY UPLC/MS system consisting of a SQD (Single Quadrupole Detector) Mass Spectrometer equipped with an Electrospray Ionization interface and a Photodiode Array Detector. PDA range was 210-400 nm. Electrospray ionization in positive and negative mode was applied. UPLC mobile phases were: (A) 10 mM $NH_4OAc$ in $H_2O$, pH 5; (B) 10 mM $NH_4OAc$ in MeCN/$H_2O$ (95:5) pH 5. Analyses were performed either with method A, B or C below reported.

Method a (Generic)
Gradient: 5 to 95% B over 3 min. Flow rate 0.5 mL/min. Temp. 40° C.
Pre column: Vanguard BEH $C_{18}$ (1.7 µm 2.1×5 mm).
Column: BEH C18 (1.7 µm 2.1×50 mm)

Method B (Polar)
Gradient: 0 to 50% B over 3 min. Flow rate 0.5 mL/min. Temp. 40° C.
Pre column: VanGuard HSS T3 $C_{18}$ (1.7 µm 2.1×5 mm).
Column HSS T3 (1.8 µm 2.1×50 mm)

Method C (Apolar)
Gradient: 50 to 100% B over 3 min. Flow rate 0.5 mL/min. Temp. 40° C.
Pre column: Vanguard BEH $C_{18}$ (1.7 µm 2.1×5 mm).
Column: BEH C18 (1.7 µm 2.1×50 mm)

Purifications by preparative HPLC/MS were run on a Waters Autopurification system consisting of a 3100 Single Quadrupole Mass Spectrometer equipped with an Electrospray Ionization interface and a 2998 Photodiode Array Detector. HPLC system included a 2747 Sample Manager, 2545 Binary Gradient Module, System Fluidic Organizer and 515 HPLC Pump. PDA range was 210-400 nm. Purifications were performed on a XBridge™ Prep $C_{18}$ OBD column (100×19 mmID, particle size 5 µm) with a XBridge™ Prep $C_{18}$ (10×19 mmID, particle size 5 µm) Guard Cartridge. Mobile phases were 10 mM $NH_4OAc$ in $H_2O$ at pH 5 adjusted with AcOH (A) and 10 mM $NH_4OAc$ in MeCN—$H_2O$ (95:5) at pH 5 (B). Electrospray ionization in positive and negative mode was used. Analyses by chiral HPLC were run on a Waters Alliance HPLC instrument consisting of an e2695 Separation Module and a 2998 Photodiode Array Detector. PDA range was 210-400 nm. Analyses were performed isocratic on a Daicel ChiralPak AD column (250×4.6 mmID, particle size 10 µm). Mobile phase was 0.1% TFA Heptane-2-Propanol (75:25). Separations by preparative chiral HPLC were run on a Waters Alliance HPLC instrument consisting of a 1525 Binary HPLC Pump, Waters Fraction Collector III and a 2998 Photodiode Array Detector. UV detection was at 240 nm. Purifications were performed isocratic on a Daicel ChiralPak AD column (250×10 mmID, particle size 10 µm). Mobile phase was 0.1% TFA Heptane-2-Propanol (75:25).

General Procedure III for the Synthesis of the Amine Derivatives III (Scheme IIIa).

Step A.

A mixture of aryl piperazine.HCl (1 eq.), N-(bromoalkyl) phthalimide (1.1 eq.) and $K_2CO_3$ (3 eq.) in acetonitrile was heated to reflux for 6 hours. The hot suspension was filtrated and the residue washed with acetone several times. The filtrates were concentrated under reduced pressure to give the phthalimide intermediates.

Step B.

The phthalimide derivative (1 eq.) and hydrazine hydrate (1.2 eq.) in methanol were heated to reflux for 2 hours. To the hot solution was added 2N HCl, and reflux was continued for one more hour. After cooling to ambient temperature, the mixture was filtrated, the residue washed with methanol, and the filtrate evaporated to dryness. This residue was suspended in water and neutralized with 2N NaOH. Extraction with EtOAc afforded an oily product, which was pure enough for the next step.

General Procedure II for the Synthesis of Phenolic Derivatives IIa (Scheme II, A-B).

Method A:

Boronic acid derivative IVa (1.2 eq.) was added to a solution of Aryl halide Va (1 eq.) in EGME/water 3:1, followed by the addition of Pd(OAc)$_2$ (0.01 eq.) and K$_2$CO$_3$ (2.5 eq.). After few minutes the yellowish suspension turned dark-black and the reaction reached full conversion.

The mixture was stirred for further 5 min., then diluted with water, acidified with 2N HCl and extracted with DCM. The organic phase was dried over Na$_2$SO$_4$ and concentrated to dryness. The crude residue was adsorbed on silica and purified by flash chromatography (Eluent: 5% MeOH in DCM).

Method B:

Boronic acid derivative Vb (1.2 eq.) was added to a solution of Aryl/Heteroaryl halide IVb (1 eq.) in EGME/water 3:1, followed by the addition of Pd(OAc)$_2$ (0.01 eq.) and K$_2$CO$_3$ (2.5 eq.); then the same procedure described in method A was applied.

General Procedure II for the Synthesis of Phenolic Derivatives IIa (Scheme II, C).

Method C:

Step A.

Aryl benzyloxy halide Vc (1 eq.) and amine IVc (1 eq.) were suspended in dry toluene. Then, compounds Pd$_2$(dba)$_3$ (0.02 eq.), DavePhos (0.06 eq.) and t-BuO$^-$K$^+$ (2 eq.) were added. The resulting mixture was stirred 2 hours at 100° C. The reaction mixture was washed with a saturated solution of NH$_4$Cl and the organic phase was collected and dried over sodium sulfate, then filtered. The evaporation under reduced pressure of the organic phase gave crude which was adsorbed on silica gel and purified by column chromatography (Eluent: cyclohexane/ethyl acetate 9:1). The fractions were collected and evaporated under reduced pressure.

Step B.

To a stirred solution of benzyloxy derivative from step A (1 eq.) and 10% Pd—C (10% by weight) (0.1 eq.) in EtOH (4 mL) was added neat TES (10 eq.) dropwise. The reaction was stirred at room temperature for 24-48 hours, then the mixture was filtered through celite and the solvent was removed in vacuo. The obtained crude was chromatographically purified on a silica gel column (Eluent: DCM/MeOH 95:5). The desired compound was recovered through evaporation under reduced pressure of the organic fractions.

General Procedure Ia for the Synthesis of Carbamate Derivatives I (Scheme Ia).

Method A.

To a solution of di-tert-butyldicarbonate (1.4 eq.) in acetonitrile were added in sequence: a solution of DMAP (1 eq.) in acetonitrile and a solution of the appropriate amine III (1 eq.) in acetonitrile. After stirring for 10 minutes at room temperature, the alcohol derivative IIa (1.2-1.4 eq.) was added. The reaction mixture was stirred for 22 h at room temperature, after which the solvent was evaporated under reduced pressure. The crude residue was solubilized in ethyl acetate and washed with a saturated solution of NaHCO$_3$.

The organic layer was dried (Na$_2$SO$_4$), concentrated and purified by flash chromatography (Eluent: 5% MeOH in DCM).

Method B.

The amine derivative III (1.0 eq.) was treated with p-nitrophenylchloroformate (1.1 eq.) and DIPEA (1.1 eq.) in a 1:1 mixture of DMA:DCM. The reaction mixture was stirred at ambient temperature for 30 minutes. To the resulting p-nitrophenyl carbamate solution were added the alcohol derivative IIa (1.25 eq.) and DIPEA (1.1 eq., 2.2 total) and the resultant mixture was stirred at room for 48-72 hours. The desired carbamate was isolated by removal of the undesired p-nitrophenol byproduct and DMA by washing several times with brine and water, collection and concentration of the organic phase and purification by flash chromatography (Eluent: 5% MeOH in DCM).

Intermediate 1. 2-[4-[4-(2-methoxyphenyl)piperazin-1-yl]butyl]isoindoline-1,3-dione

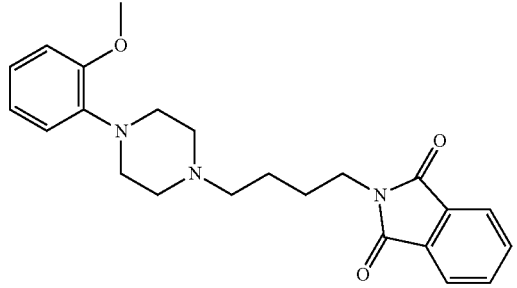 [SMILES: COc1ccccc1N1CCN(CCCCN2C(=O)c3ccccc3C2=O)CC1]

The title compound was synthesized applying the general procedure III step A using 1-(2-methoxyphenyl)piperazine hydrochloride (2.62 mmol, 600 mg), N-(4-bromobutyl) phthalimide (2.89 mmol, 814 mg), and K$_2$CO$_3$ (7.87 mmol, 1088 mg) in 7 mL of acetonitrile. White solid 953 mg (92%). UPLC-MS (method A): Rt 1.27 min; m/z 242 [M–H]$^+$. $^1$H NMR (400 MHz, Chloroform-d) δ 7.85 (dd, J=3.02, 5.46 Hz, 2H), 7.75-7.69 (m, 2H), 7.04-6.77 (m, 4H), 3.87 (s, 3H), 3.74 (t, J=7.06 Hz, 2H), 3.10 (s, 4H), 2.67 (s, 4H), 2.52-2.39 (m, 2H), 1.80-1.69 (m, 2H), 1.67-1.55 (m, 2H).

Intermediate 2. 2-[4-[4-(2,3-dichlorophenyl)piperazin-1-yl]butyl]isoindoline-1,3-dione

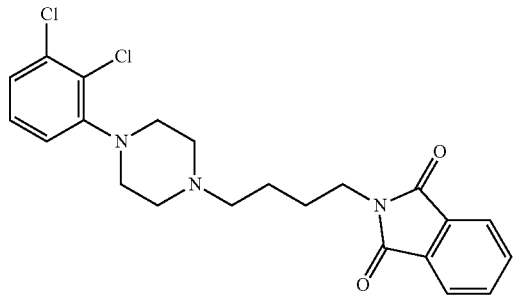 [SMILES: O=C1c2ccccc2C(=O)N1CCCCN1CCN(c2cccc(Cl)c2Cl)CC1]

The title compound was synthesized applying the general procedure III step A using 1-(2,3-dichlorophenyl)piperazine hydrochloride (1.87 mmol, 500 mg), N-(4-bromobutyl) phthalimide (2.06 mmol, 579.9 mg) and K$_2$CO$_3$ (5.61 mmol, 774.7 mg) in 7 mL of acetonitrile. White solid 771 mg (95%). UPLC-MS (method A): Rt 2.66 min; m/z 432 [M–H]+. 1H NMR (400 MHz, Chloroform-d) δ 7.86 (dd, J=3.05, 5.42 Hz, 2H), 7.73 (dd, J=3.04, 5.45 Hz, 2H), 7.20-7.12 (m, 2H), 6.97 (dd, J=2.79, 6.76 Hz, 1H), 3.75 (t, J=7.07 Hz, 2H), 3.16-3.03 (m, 4H), 2.75-2.59 (m, 4H), 2.50 (t, J=7.60 Hz, 2H), 1.77 (tt, J=6.35, 7.59 Hz, 2H), 1.70-1.56 (m, 2H).

Intermediate 3. 2-[3-[4-(2,3-dichlorophenyl)piperazin-1-yl]propyl]isoindoline-1,3-dione

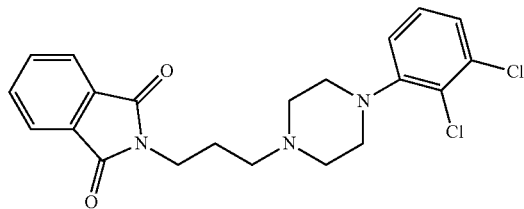 [SMILES: O=C1c2ccccc2C(=O)N1CCCN1CCN(c2cccc(Cl)c2Cl)CC1]

The title compound was synthesized applying the general procedure III step A using 1-(2,3-dichlorophenyl)piperazine hydrochloride (400.0 mg, 1.49 mmol), N-(3-Bromopropyl) phthalimide (440.8 mg, 1.64 mmol) and K2CO3 (516.4 mg, 3.74 mmol) in 7 mL of acetonitrile. White solid 534 mg (83%). UPLC-MS (method A): Rt 2.92 min; m/z 418 [M–H]+. 1H NMR (400 MHz, Chloroform-d) δ 7.87 (dd, J=3.06, 5.44 Hz, 2H), 7.73 (dd, J=3.06, 5.44 Hz, 2H), 7.20-7.09 (m, 2H), 6.85 (dd, J=2.13, 7.37 Hz, 1H), 3.83 (t, J=6.86 Hz, 2H), 2.95 (m, 4H), 2.68-2.61 (m, 4H), 2.56 (t, J=7.05 Hz, 2H), 1.96 (p, J=6.79 Hz, 2H).

Intermediate 4. 2-[3-(4-phenylpiperazin-1-yl)propyl]isoindoline-1,3-dione

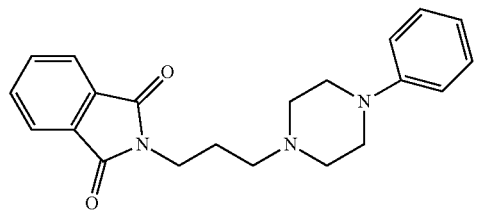 [SMILES: O=C1c2ccccc2C(=O)N1CCCN1CCN(c2ccccc2)CC1]

The title compound was synthesized applying the general procedure III step A using 1-phenyl piperazine hydrochloride (300.0 mg, 1.85 mmol), N-(3-Bromopropyl)phthalimide (545.4 mg, 2.03 mmol) and K2CO3 (766.8 mg, 5.55 mmol) in 7 mL of acetonitrile. White solid 600 mg (93%). UPLC-MS (method A): Rt 2.14 min; m/z 350 [M–H]+. 1H NMR (400 MHz, Chloroform-d) δ 7.85 (dd, J=5.4, 3.0 Hz, 2H), 7.70 (dd, J=5.5, 3.0 Hz, 2H), 7.29-7.21 (m, 2H), 6.90-6.81 (m, 3H), 3.81 (t, J=6.9 Hz, 2H), 3.11-3.01 (m, 4H), 2.59-2.53 (m, 4H), 2.50 (t, J=6.9 Hz, 2H), 1.93 (p, J=6.9 Hz, 2H).

Intermediate 5. 4-[4-(2-methoxyphenyl)piperazin-1-yl]butan-1-amine

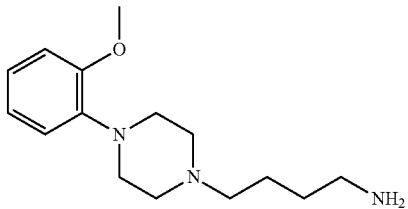 [SMILES: COc1ccccc1N1CCN(CCCCN)CC1]

The title compound was synthesized applying the general procedure III step B using INTERMEDIATE 1 (953.0 mg, 2.42 mmol) and hydrazine hydrate (0.14 mL, 2.91 mmol) in 3 mL of methanol. Yellow oil 338 mg (53%). UPLC-MS (method A): Rt 1.07 min; m/z 263 [M–H]+. 1H NMR (400 MHz, Chloroform-d) δ 7.04-6.90 (m, 3H), 6.87 (dt, J=8.0, 1.4 Hz, 1H), 3.88 (d, J=1.6 Hz, 3H), 3.12 (s, 4H), 2.74 (td, J=6.8, 1.5 Hz, 2H), 2.68 (d, J=5.8 Hz, 4H), 2.49-2.39 (m, 2H), 1.64-1.54 (m, 2H), 1.50 (dtd, J=8.8, 6.9, 5.3 Hz, 2H), 1.36 (s, 2H).

Intermediate 6. 4-[4-(2,3-dichlorophenyl)piperazin-1-yl]butan-1-amine

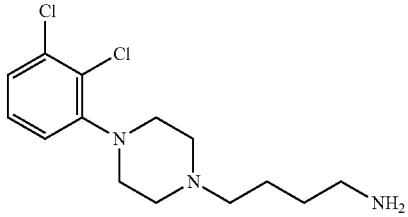

The title compound was synthesized applying the general procedure III step B using INTERMEDIATE 2 (771 mg, 1.78 mmol) and hydrazine hydrate (0.10 mL, 2.14 mmol) in 3 mL of methanol, then 2 mL of HCl. Yellow oil 351 mg (65%). UPLC-MS (method A): Rt 1.64 min; m/z 302 [M–H]+. 1H NMR (400 MHz, Chloroform-d) δ 7.18-7.09 (m, 2H), 6.95 (dd, J=6.5, 3.1 Hz, 1H), 3.16-2.98 (m, 4H), 2.72 (t, J=6.8 Hz, 2H), 2.63 (d, J=7.0 Hz, 4H), 2.48-2.36 (m, 2H), 1.62-1.42 (m, 4H), 1.37 (s, 2H).

Intermediate 7. 3-[4-(2,3-dichlorophenyl)piperazin-1-yl]propan-1-amine

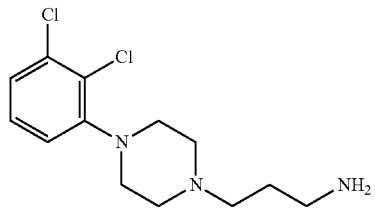 [SMILES: NCCCN1CCN(c2cccc(Cl)c2Cl)CC1]

The title compound was synthesized applying the general procedure III step B using INTERMEDIATE 3 (534 mg, 1.28 mmol) and hydrazine hydrate (0.07 mL, 1.53 mmol) in 4 mL of methanol, then 2 mL of HCl. Yellow oil 233 mg (63%). UPLC-MS (method A): Rt 1.81 min; m/z 288 [M−H]+. 1H NMR (400 MHz, Chloroform-d) δ 7.18-7.09 (m, 2H), 6.95 (dd, J=6.5, 3.1 Hz, 1H), 3.87 (s, 3H), 3.11 (s, 4H), 2.99 (t, J=6.2 Hz, 2H), 2.72 (s, 4H), 2.59 (t, J=6.5 Hz, 2H), 1.98 (s, 2H), 1.82 (p, J=6.4 Hz, 2H).

Intermediate 8.
3-(4-phenylpiperazin-1-yl)propan-1-amine

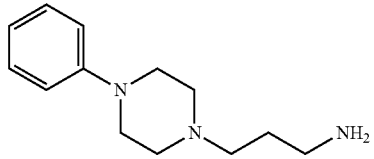 [SMILES: NCCCN1CCN(c2ccccc2)CC1]

The title compound was synthesized applying the general procedure III step B using INTERMEDIATE 4 (600 mg, 1.72 mmol) and hydrazine hydrate (0.10 mL, 2.06 mmol) in 4 mL of methanol, then 2 mL of HCl. Yellow oil 278 mg (74%). UPLC-MS (method A): Rt 1.09 min; m/z 220 [M−H]+. 1H NMR (400 MHz, Chloroform-d) δ 7.31-7.23 (m, 2H), 6.97-6.92 (m, 2H), 6.86 (tt, J=7.3, 1.1 Hz, 1H), 3.27-3.17 (m, 4H), 2.79 (t, J=6.8 Hz, 2H), 2.68-2.56 (m, 4H), 2.52-2.44 (m, 2H), 1.75-1.64 (m, 2H).

Intermediate 9. 3-(3-hydroxyphenyl)benzamide

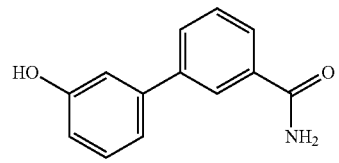 [SMILES: NC(=O)c1cccc(-c2cccc(O)c2)c1]

The title compound was synthesized according to the general procedure II method A using 3-benzamideboronic acid (143.0 mg, 0.87 mmol), 3-bromophenol (100.0 mg, 0.58 mmol) Pd(OAc)2 (1.3 mg, 0.01 mmol) and K2CO3 (199.7 mg, 1.45 mmol) in EGME/water 3:1 (4 mL). Brown solid 119 mg (97%). UPLC-MS (method A): Rt 1.59 min; m/z 214 [M−H]+. 1H NMR (400 MHz, DMSO-d6) δ 9.57 (s, 1H), 8.11 (t, J=1.86 Hz, 1H), 7.85 (dt, J=1.37, 7.80 Hz, 1H), 7.75 (dt, J=1.37, 7.75 Hz, 1H), 7.53 (t, J=7.72 Hz, 1H), 7.40 (s, 2H), 7.29 (t, J=7.84 Hz, 1H), 7.14 (dt, J=1.20, 7.74 Hz, 1H), 7.10 (t, J=2.10 Hz, 1H), 6.80 (dd, J=2.38, 7.96 Hz, 1H).

Intermediate 10. 3-phenylphenol

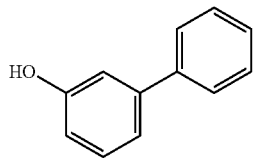 [SMILES: Oc1cccc(-c2ccccc2)c1]

The title compound was synthesized according to the general procedure II method A using benzeneboronic acid (317.1 mg, 2.60 mmol), 3-bromophenol (300.0 mg, 1.73 mmol) Pd(OAc)2 (3.9 mg, 0.02 mmol) and K2CO3 (599.2 mg, 4.34 mmol) in EGME/water 3:1 (8 mL). Brown solid 285 mg (97%). UPLC-MS (method A): Rt 2.33 min; m/z 169 [M]−. 1H NMR (400 MHz, DMSO-d6) δ 9.52 (s, 1H), 7.62-7.57 (m, 2H), 7.45 (ddd, J=7.8, 6.9, 1.2 Hz, 2H), 7.39-7.32 (m, 1H), 7.26 (t, J=7.8 Hz, 1H), 7.07 (ddd, J=7.7, 1.8, 1.0 Hz, 1H), 7.03 (t, J=2.0 Hz, 1H), 6.78 (ddt, J=8.3, 2.1, 1.0 Hz, 1H).

Intermediate 11. 3-(4-hydroxyphenyl)benzamide

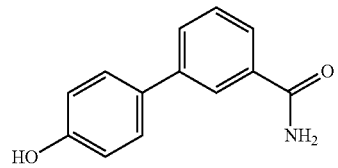

The title compound was synthesized according to the general procedure II method B using 4-hydroxybenzeneboronic acid (450.0 mg, 3.26 mmol), 3-bromobenzamide (783.2 mg, 3.92 mmol) Pd(OAc)2 (7.3 mg, 0.03 mmol) and K2CO3 (1127.5 mg, 8.16 mmol) in EGME/water 3:1 (12 mL). Brown solid 625 mg (90%). UPLC-MS (method A): Rt 1.53 min; m/z 214 [M−H]+. 1H NMR (400 MHz, DMSO-d6) δ 9.58 (s, 1H), 8.12-8.02 (m, 2H), 7.75 (dddd, J=20.2, 7.7, 1.8, 1.1 Hz, 2H), 7.61-7.52 (m, 2H), 7.48 (t, J=7.7 Hz, 1H), 7.37 (q, J=3.6, 3.0 Hz, 1H), 6.92-6.83 (m, 2H).

Intermediate 12. 3-(4,4-difluoro-1-piperidyl)phenol

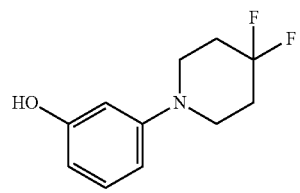 [SMILES: Oc1cccc(N2CCC(F)(F)CC2)c1]

The title compound was synthesized according to the general procedure II method C sing commercially available 1-benzyloxy-3-bromo-benzene (200.0 mg, 0.76 mmol), 4,4-difluoropiperidine hydrochloride (119.8 mg, 0.76 mmol), Pd2(dba)3 (13.9 mg, 0.02 mmol), DavePhos (17.9 mg, 0.06 mmol) and t-BuO−K+ (170.6 mg, 1.52 mmol) in dry Toluene (5 mL). The second step was pursued using Pd—C (7.0 mg, 0.07 mol), triethylsilane (1.05 mL, 6.59 mmol) in EtOH (4 mL). Brown oil 63 mg (45%). UPLC-MS (method A): Rt 2.10 min; m/z 214 [M−H]+. 1H NMR (400 MHz, Chloroform-d) δ 7.13 (t, J=8.1 Hz, 1H), 6.54 (ddd, J=8.2, 2.4, 0.8 Hz, 1H), 6.43 (t, J=2.3 Hz, 1H), 6.36 (ddd, J=8.0, 2.3, 0.8 Hz, 1H), 3.39-3.31 (m, 4H), 2.15-2.03 (m, 4H).

Intermediate 13. 2-[3-[4-(2-methoxyphenyl)piperazin-1-yl]propyl]isoindoline-1,3-dione

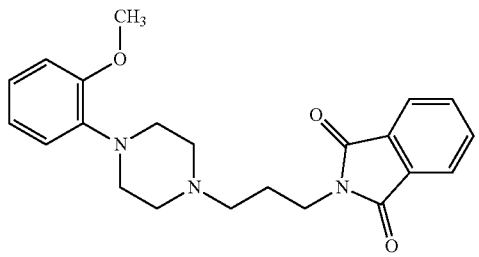 [SMILES: COc1ccccc1N1CCN(CCCN2C(=O)c3ccccc3C2=O)CC1]

The title compound was synthesized applying the general procedure III step A using 1-(2-methoxyphenyl)piperazine hydrochloride (1000.0 mg, 4.37 mmol), N-(3-Bromopropyl)phthalimide (1289.4 mg, 4.81 mmol) and $K_2CO_3$ (1510.7 mg, 10.93 mmol) in 7 mL of acetonitrile. White solid 1549 mg (93%). UPLC-MS (method A): Rt. 1.96 min; m/z 380 [M−H]$^+$. $^1$H NMR (400 MHz, DMSO-d$_6$) δ 7.91-7.85 (m, 2H), 7.85-7.78 (m, 2H), 6.94-6.86 (m, 2H), 6.83 (ddd, J=7.8, 6.7, 2.1 Hz, 1H), 6.70 (dd, J=7.8, 1.5 Hz, 1H), 3.74 (s, 3H), 3.68 (t, J=6.7 Hz, 2H), 2.79-2.61 (m, 4H), 2.38 (t, J=6.5 Hz, 6H), 1.78 (p, J=6.6 Hz, 2H).

Intermediate 14. 3-[4-(2-methoxyphenyl)piperazin-1-yl]propan-1-amine

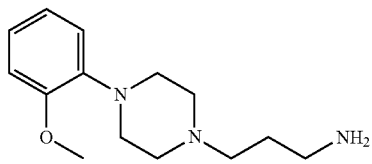 [SMILES: COc1ccccc1N1CCN(CCCN)CC1]

The title compound was synthesized applying the general procedure III step B using Intermediate 13 (1549 mg, 4.08 mmol) and hydrazine hydrate (0.24 mL, 4.90 mmol) in 8 mL of methanol. Yellow oil 631 mg (62%). UPLC-MS (method A): Rt 1.13 min; m/z 250 [M−H]$^+$. $^1$H NMR (400 MHz, Chloroform-d) δ 7.01 (ddd, J=7.9, 6.4, 2.6 Hz, 1H), 6.98-6.90 (m, 2H), 6.87 (dd, J=8.0, 1.3 Hz, 1H), 3.87 (s, 3H), 3.11 (s, 4H), 2.99 (t, J=6.2 Hz, 2H), 2.72 (s, 4H), 2.59 (t, J=6.5 Hz, 2H), 1.98 (s, 2H), 1.82 (p, J=6.4 Hz, 2H).

Intermediate 15. 4-(4,4-difluoro-1-piperidyl)phenol

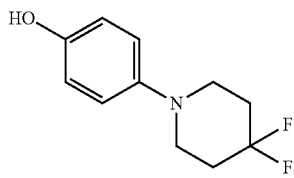 [SMILES: Oc1ccc(N2CCC(F)(F)CC2)cc1]

The title compound was synthesized according to the general procedure II method C using commercially available 1-benzyloxy-4-bromo-benzene (200.0 mg, 0.76 mmol), 4,4-difluoropiperidine hydrochloride (119.8 mg, 0.76 mmol), Pd$_2$(dba)$_3$ (13.9 mg, 0.02 mmol), DavePhos (17.9 mg, 0.05 mmol) and t-BuO$^-$K$^+$ (255.9 mg, 2.28 mmol) in dry Toluene (3 mL). The second step was pursued using Pd—C (7.0 mg, 0.07 mol), triethylsilane (1.05 mL, 6.59 mmol) in EtOH (4 mL). Brown oil 112 mg (69% over two steps). UPLC-MS (method A): Rt 2.00 min; m/z 214 [M−H]$^+$. $^1$H NMR (400 MHz, Chloroform-d) δ 6.93-6.86 (m, 2H), 6.81-6.76 (m, 2H), 3.26-3.18 (m, 4H), 2.14 (tt, J=13.8, 5.7 Hz, 4H).

Intermediate 16. 2-[4-(4-phenyl-1-piperidyl)butyl]isoindoline-1,3-dione

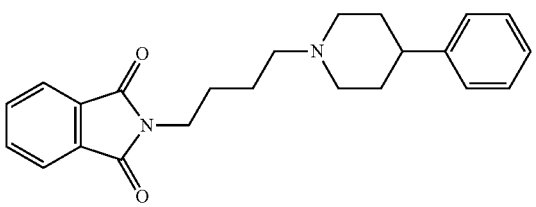 [SMILES: O=C1c2ccccc2C(=O)N1CCCCN1CCC(c2ccccc2)CC1]

The title compound was synthesized applying the general procedure III step A, using 4-phenylpiperidine (161 mg, 1.00 mmol), N-(4-bromobutyl)phthalimide (296 mg, 1.05 mmol), $K_2CO_3$ (152 mg, 1.50 mmol) and MeCN (2 mL). White solid, 340 mg (94%). UPLC-MS (method A): Rt 2.04 min, m/z 363 [M+H]$^+$. $^1$H NMR (400 MHz, Chloroform-d) δ 7.91-7.80 (m, 2H), 7.76 (td, J=5.2, 2.1 Hz, 2H), 7.38-7.20 (m, 5H), 3.76 (t, J=6.8 Hz, 2H), 3.46 (s, 2H), 2.92 (s, 2H), 2.78-2.53 (m, 3H), 2.41 (s, 2H), 1.91 (s, 4H), 1.81 (p, J=6.9 Hz, 2H).

Intermediate 17. 2-[3-[4-[2-(trifluoromethyl)phenyl]piperazin-1-yl]propyl]isoindoline-1,3-dione

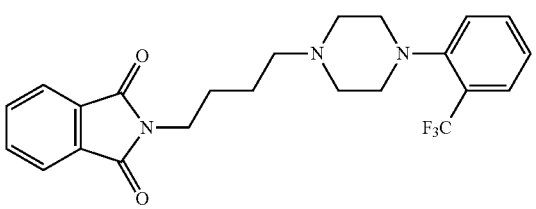 [SMILES: O=C1c2ccccc2C(=O)N1CCCCN1CCN(c2ccccc2C(F)(F)F)CC1]

The title compound was synthesized applying the general procedure III step A, using 1-[2-(trifluoromethyl)phenyl]piperazine (0.187 mL, 1.00 mmol), N-(3-bromopropyl)phthalimide (281 mg, 1.00 mmol), triethylamine (0.348 mL, 2.50 mmol) and MeCN (2 mL). White solid, 349 mg (84%). UPLC-MS (method A): Rt 2.58 min, m/z 418 [M+H]$^+$. $^1$H NMR (400 MHz, DMSO-d$_6$) δ 7.95-7.84 (m, 4H), 7.61 (t, J=7.8 Hz, 2H), 7.30 (t, J=7.6 Hz, 1H), 7.21 (d, J=8.0 Hz, 1H), 3.69 (t, J=6.7 Hz, 2H), 2.59 (t, J=4.4 Hz, 4H), 2.39 (t, J=6.4 Hz, 6H), 1.78 (p, J=6.5 Hz, 2H).

Intermediate 18. 2-[3-[4-(o-tolyl)piperazin-1-yl]propyl]isoindoline-1,3-dione

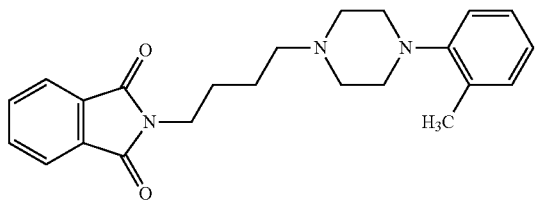 [SMILES: Cc1ccccc1N1CCN(CCCCN2C(=O)c3ccccc3C2=O)CC1]

The title compound was synthesized applying the general procedure III step A, using 1-(o-tolyl)piperazine (176 mg, 1.00 mmol), N-(3-bromopropyl)phthalimide (281 mg, 1.00 mmol), triethylamine (0.348 mL, 2.50 mmol) and MeCN (2 mL). White solid, 266 mg (73%). UPLC-MS (method A): Rt 2.31 min, m/z 364 [M+H]$^+$. $^1$H NMR (400 MHz, DMSO-d$_6$) δ 8.09-7.57 (m, 4H), 7.18-7.01 (m, 2H), 6.91 (td, J=7.4, 1.1 Hz, 1H), 6.77 (d, J=7.9 Hz, 1H), 3.69 (t, J=6.7 Hz, 2H), 2.56 (s, 3H), 2.40 (t, J=6.4 Hz, 5H), 2.18 (s, 3H), 1.79 (p, J=6.5 Hz, 2H).

Intermediate 19. 4-(4-phenyl-1-piperidyl)butan-1-amine

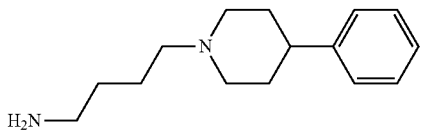

The title compound was synthesized applying the general procedure III step B, using INTERMEDIATE 16 (340 mg, 0.94 mmol), hydrazine hydrate (0.070 mL, 1.5 mmol) in MeOH (5 mL), then HCl (2 mL). Slightly yellow solid, 152 mg (70%). UPLC-MS (method A): Rt 1.18 min, m/z 233 [M+H]$^+$. $^1$H NMR (400 MHz, Chloroform-d) δ 7.35-7.14 (m, 5H), 3.08 (d, J=11.7 Hz, 2H), 2.75 (t, J=6.9 Hz, 2H), 2.51 (tq, J=12.5, 7.3, 6.1 Hz, 1H), 2.45-2.35 (m, 2H), 2.05 (tt, J=11.9, 5.8 Hz, 2H), 1.90-1.77 (m, 4H), 1.65-1.41 (m, 6H).

Intermediate 20. 3-[4-[2-(trifluoromethyl)phenyl]piperazin-1-yl]propan-1-amine

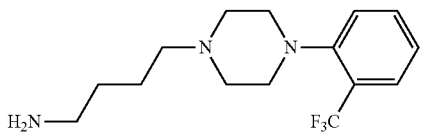 [SMILES: NCCCCN1CCN(c2ccccc2C(F)(F)F)CC1]

The title compound was synthesized applying the general procedure III step B, using INTERMEDIATE 17 (349 mg, 0.84 mmol), hydrazine hydrate (0.059 mL, 1.5 mmol) in MeOH (5 mL), then HCl (2 mL). Colourless wax, 225 mg (94%). UPLC-MS (method A): Rt 1.54 min, m/z 288 [M+H]$^+$. $^1$H NMR (400 MHz, Chloroform-d) δ 7.63 (dd, J=7.9, 1.5 Hz, 1H), 7.55-7.46 (m, 1H), 7.39 (d, J=8.0 Hz, 1H), 7.22 (t, J=7.6 Hz, 1H), 2.98 (t, J=4.8 Hz, 4H), 2.80 (t, J=6.8 Hz, 2H), 2.62 (s, 4H), 2.54-2.43 (m, 2H), 1.70 (dt, J=14.1, 6.9 Hz, 2H), 1.58 (s, 2H).

Intermediate 21. 3-[4-(o-tolyl)piperazin-1-yl]propan-1-amine

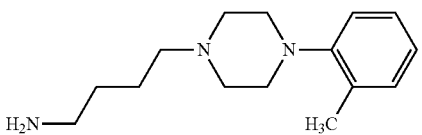

The title compound was synthesized applying the general procedure III step B, using INTERMEDIATE 18 (266 mg, 0.73 mmol), hydrazine hydrate (0.059 mL, 1.5 mmol) in MeOH (5 mL), then HCl (2 mL). Colourless wax, 170 mg (99%). UPLC-MS (method A): Rt 1.21 min, m/z 234 [M+H]$^+$. $^1$H NMR (400 MHz, Chloroform-d) δ 7.18 (t, J=7.4 Hz, 2H), 7.05 (d, J=7.7 Hz, 1H), 6.99 (td, J=7.4, 1.2 Hz, 1H), 2.96 (t, J=4.8 Hz, 4H), 2.80 (t, J=6.8 Hz, 2H), 2.63 (bs, 4H), 2.55-2.42 (m, 2H), 2.32 (s, 3H), 1.71 (dt, J=14.1, 6.9 Hz, 2H), 1.53 (bs, 2H).

Intermediate 22. 3-(2-fluoro-4-hydroxy-phenyl)benzamide

The title compound was prepared according to the general procedure II method A. Starting with 4-bromo-3-fluorophenol (250 mg, 1.32 mmol), (3-carbamoylphenyl)boronic acid (260 mg, 1.58 mmol), Pd(OAc)$_2$ (3 mg, 0.01 mmol) and 3:1 EGME/H$_2$O (4 mL). White solid, 176 mg (58%). UPLC-MS (method A): Rt 1.63 min, m/z 232 [M+H]$^+$. $^1$H NMR (400 MHz, DMSO-d$_6$) δ 10.07 (s, 1H), 8.03 (s, 1H), 8.00-7.93 (m, 1H), 7.83 (dt, J=7.7, 1.3 Hz, 1H), 7.66-7.58 (m, 1H), 7.51 (t, J=7.7 Hz, 1H), 7.44-7.35 (m, 2H), 6.78-6.65 (m, 2H).

Intermediate 23. 2-[(E)-4-[4-(2,3-dichlorophenyl)piperazin-1-yl]but-2-enyl]isoindoline-1,3 dione

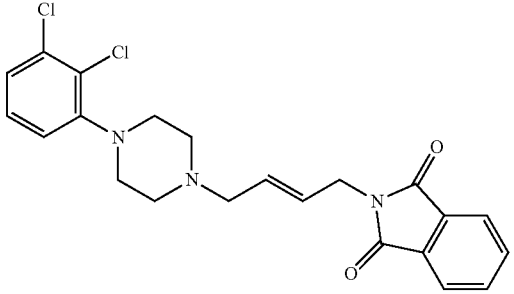 [SMILES: O=C1c2ccccc2C(=O)N1C/C=C/CN1CCN(c2cccc(Cl)c2Cl)CC1]

The title compound was obtained through a two-step process starting from potassium isoindolin-2-ide-1,3-dione and (E)-1,4-dichlorobut-2-ene in presence of DMF. The so obtained derivative was used in general procedure III step A, using 1-(2,3-dichlorophenyl)piperazine hydrochloride (250 mg, 0.93 mmol), potassium carbonate (323 mg, 2.34 mmol) and MeCN (3 mL). White solid, 332 mg (83% over two steps). UPLC-MS (method A): Rt 2.73 min, m/z 430 [M+H]$^+$. $^1$H NMR (400 MHz, Chloroform-d) δ 7.89-7.80 (m, 2H), 7.75-7.68 (m, 2H), 7.16-7.09 (m, 2H), 6.94 (td, J=7.3, 6.7, 2.8 Hz, 1H), 5.74 (tt, J=4.4, 2.2 Hz, 2H), 4.33-4.28 (m, 2H), 3.12-2.99 (m, 6H), 2.71 (s, 1H), 2.60 (s, 3H).

INTERMEDIATE 24

(E)-4-[4-(2,3-dichlorophenyl)piperazin-1-yl]but-2-en-1-amine

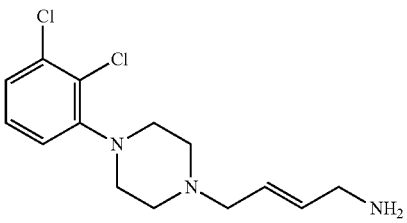 [SMILES: NC/C=C/CN1CCN(c2cccc(Cl)c2Cl)CC1]

The title compound was synthesized applying the general procedure III step B, using INTERMEDIATE 23 (332 mg, 0.77 mmol), hydrazine hydrate (0.040 mL, 0.93 mmol) in MeOH (5 mL), then HCl (2 mL). Slightly yellow solid, 203 mg (88%). UPLC-MS (method A): Rt 1.57 min, m/z 300 [M+H]$^+$. $^1$H NMR (400 MHz, Chloroform-d) δ 7.10 (dd, J=5.5, 2.6 Hz, 2H), 6.95-6.89 (m, 1H), 5.74 (dt, J=15.3, 5.4 Hz, 1H), 5.63 (dddd, J=13.2, 8.2, 6.3, 3.0 Hz, 1H), 3.28 (d, J=5.1 Hz, 2H), 3.08-2.95 (m, 6H), 2.60 (s, 4H).

Intermediate 25. 2-[4-[4-[2-(trifluoromethyl)phenyl]piperazin-1-yl]butyl]isoindoline-1,3-dione

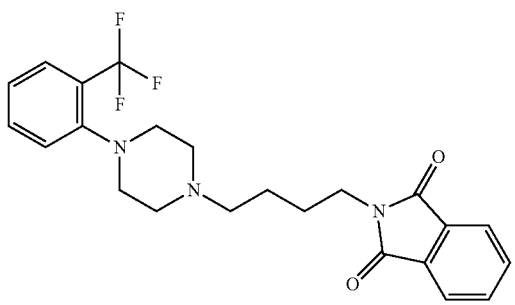 [SMILES: O=C1c2ccccc2C(=O)N1CCCCN1CCN(c2ccccc2C(F)(F)F)CC1]

The title compound was synthesized applying the general procedure III step A using 1-(2-trifluoromethylphenyl)piperazine hydrochloride (1.52 mmol, 350 mg), N-(4-bromobutyl)phthalimide (1.52 mmol, 429 mg), and K$_2$CO$_3$ (3.8 mmol, 525 mg) in 6 mL of acetonitrile. White solid 600 mg (91%). $^1$H NMR (400 MHz, Chloroform-d) δ 7.86 (dd, J=5.4, 3.1 Hz, 2H), 7.77-7.69 (m, 2H), 7.62 (dd, J=7.9, 1.6 Hz, 1H), 7.54-7.48 (m, 1H), 7.38 (d, J=8.1 Hz, 1H), 7.25-7.17 (m, 1H), 3.75 (t, J=7.1 Hz, 2H), 2.95 (q, J=4.7 Hz, 4H), 2.60 (s, 3H), 2.53-2.39 (m, 2H), 2.13 (s, 1H), 1.76 (tt, J=7.7, 6.5 Hz, 2H), 1.68-1.54 (m, 2H).

Intermediate 26. 4-[4-[2-(trifluoromethyl)phenyl]piperazin-1-yl]butan-1-amine

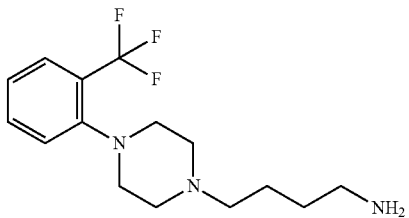 [SMILES: NCCCCN1CCN(c2ccccc2C(F)(F)F)CC1]

The title compound was synthesized applying the general procedure III step B using INTERMEDIATE 25 (600 mg, 1.39 mmol) and hydrazine hydrate (0.08 mL, 1.67 mmol) in 4 mL of methanol, then 2 mL of HCl. Yellow oil 312 mg (75%). $^1$H NMR (400 MHz, Chloroform-d) δ 7.62 (dd, J=7.8, 1.6 Hz, 1H), 7.51 (td, J=7.7, 1.6 Hz, 1H), 7.38 (d, J=7.8 Hz, 1H), 7.25-7.17 (m, 1H), 3.05-2.93 (m, 4H), 2.73 (t, J=6.8 Hz, 2H), 2.60 (m, 4H), 2.50-2.36 (m, 2H), 1.61-1.42 (m, 4H).

Intermediate 27. 4-(2-pyridyl)phenol

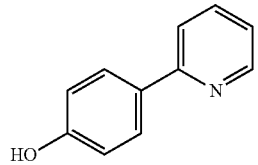 [SMILES: Oc1ccc(-c2ccccn2)cc1]

The title compound was synthesized according to the general procedure II method A using 4-hydroxyphenylboronic acid (200.0 mg, 1.45 mmol), 2-bromopyridine (0.14 mL, 1.45 mmol) Pd(OAc)$_2$ (3.3 mg, 0.01 mmol) and K$_2$CO$_3$ (601 mg, 4.35 mmol) in EGME/water 3:1 (4 mL). Brown solid 137 mg (55%). $^1$H NMR (400 MHz, DMSO-d$_6$) δ 9.71 (s, 1H), 8.59 (ddd, J=4.8, 1.7, 1.1 Hz, 1H), 8.00-7.86 (m, 2H), 7.89-7.73 (m, 2H), 7.24 (ddd, J=6.7, 4.8, 1.8 Hz, 1H), 6.91-6.83 (m, 2H).

Intermediate 28. 2-[4-[4-(o-tolyl)piperazin-1-yl]butyl]isoindoline-1,3-dione

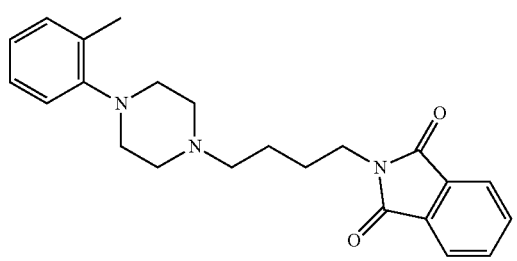 [SMILES: Cc1ccccc1N1CCN(CCCCN2C(=O)c3ccccc3C2=O)CC1]

The title compound was synthesized applying the general procedure III step A using 1-(2-methylphenyl)piperazine (1.99 mmol, 350 mg), N-(4-bromobutyl)phthalimide (1.99 mmol, 560 mg), and K$_2$CO$_3$ (4.97 mmol, 686 mg) in 6 mL of acetonitrile. White solid 750 mg (99%). $^1$H NMR (400 MHz, Chloroform-d) δ 7.92-7.79 (m, 2H), 7.72 (dt, J=5.5, 3.1 Hz, 2H), 7.16 (t, J=7.6 Hz, 2H), 7.08-6.88 (m, 2H), 3.74 (t, J=7.1 Hz, 2H), 2.93 (t, J=4.8 Hz, 4H), 2.60 (s, 4H), 2.52-2.39 (m, 2H), 2.30 (s, 3H), 1.75 (p, J=7.3 Hz, 2H), 1.59 (tt, J=9.7, 5.9 Hz, 2H).

Intermediate 29.
4-[4-(o-tolyl)piperazin-1-yl]butan-1-amine

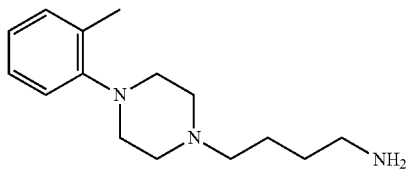 [SMILES: Cc1ccccc1N1CCN(CCCCN)CC1]

The title compound was synthesized applying the general procedure III step B using INTERMEDIATE 28 (750 mg, 1.99 mmol) and hydrazine hydrate (0.12 mL, 2.38 mmol) in 4 mL of methanol, then 2 mL of HCl. Yellow oil 384 mg (78%). $^1$H NMR (400 MHz, Chloroform-d) δ 7.18 (t, J=7.4 Hz, 2H), 7.05 (dd, J=7.5, 1.5 Hz, 1H), 6.99 (td, J=7.4, 1.3 Hz, 1H), 2.97 (t, J=4.8 Hz, 4H), 2.75 (t, J=6.8 Hz, 2H), 2.63 (s, 4H), 2.53-2.39 (m, 2H), 1.63-1.46 (m, 4H).

Intermediate 30. 3-methoxy-4-phenyl-phenol

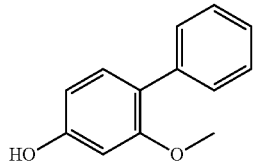

A 50 ml flask containing a magnetic stir bar was charged with PdCl$_2$(dppf) (21 mg, 0.03 mmol), benzeneboronic acid (270 mg, 2.22 mmol), K$_2$CO$_3$ (612 mg, 4.43 mmol) and 4-bromo-3-methoxy-phenol (300 mg, 1.48 mmol). The entire solid were dissolved in a 3:1 mixture of dioxane and water (4 mL) and the reaction mixture was vigorously stirred at 90° C. for 3 hrs. The reaction mixture was diluted with water and acidified with HCl 2N and extracted with DCM. The organic phase was collected and evaporated in vacuo. The crude was purified by column chromatography on silica gel (Eluent: Cyclohexane/ethyl acetate). The organic fractions were collected and evaporated in vacuo. Yellowish oil 250 mg (84%). $^1$H NMR (400 MHz, DMSO-d$_6$) δ 9.59 (s, 1H), 7.43-7.39 (m, 2H), 7.35 (dd, J=8.4, 6.8 Hz, 2H), 7.27-7.21 (m, 1H), 7.08 (d, J=8.2 Hz, 1H), 6.51 (d, J=2.2 Hz, 1H), 6.44 (dd, J=8.2, 2.3 Hz, 1H), 3.71 (s, 3H).

Intermediate 31. 2-(2-bromoethyl)oxirane

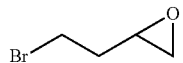

4-bromobut-1-ene (1000 mg, 7.41 mmol) was dissolved in DCM (30 mL), and then m-CPBA (1917 mg, 11.11 mmol) was added portion-wise into the solution. The mixture was stirred overnight at room temperature, then neutralized with 0.1 N sodium hydroxide solution, extracted with DCM, and dried over anhydrous Na$_2$SO$_4$. The solvents were removed to afford colorless oil, which can be used directly in next step. Colorless oil 1050 mg (94%). $^1$H NMR (400 MHz, Chloroform-d) δ 3.54 (dd, J=7.4, 5.9 Hz, 2H), 3.12 (dtd, J=6.7, 4.2, 2.7 Hz, 1H), 2.87 (dd, J=4.9, 4.0 Hz, 1H), 2.61 (dd, J=4.9, 2.6 Hz, 1H), 2.19 (dtd, J=14.8, 7.4, 4.5 Hz, 1H), 2.08 (dq, J=14.7, 6.1 Hz, 1H).

Intermediate 32.
2-[2-(oxiran-2-yl)ethyl]isoindoline-1,3-dione

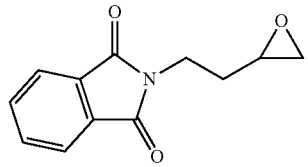 [SMILES: O=C1c2ccccc2C(=O)N1CCC1CO1]

A suspension of phthalimide potassium salt (800 mg, 4.32 mmol) in DMF (15 mL) was treated with INTERMEDIATE 31 (978 mg, 6.48 mmol), heated at 100° C. overnight. The cooled reaction mixture was filtered, diluted with EtOAc and washed with H$_2$O. The organic phase was dried over sodium sulfate and the volatiles were removed in vacuo to give desired compound as foam, which was used without further purification. White foam 890 mg (95%). $^1$H NMR (400 MHz, Chloroform-d) δ 7.86 (dd, J=5.5, 3.0 Hz, 2H), 7.76-7.68 (m, 2H), 3.54 (dd, J=7.4, 5.9 Hz, 2H), 3.12 (dtd, J=6.8, 4.2, 2.7 Hz, 1H), 2.87 (dd, J=4.9, 4.0 Hz, 1H), 2.61 (dd, J=4.9, 2.6 Hz, 1H), 2.19 (dtd, J=14.8, 7.4, 4.5 Hz, 1H), 2.08 (dq, J=14.7, 6.1 Hz, 1H).

Intermediate 33. 2-[4-[4-(2,3-dichlorophenyl)piperazin-1-yl]-3-hydroxy-butyl]isoindoline-1,3-dione

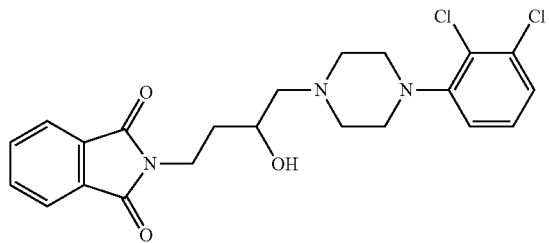 [SMILES: O=C1c2ccccc2C(=O)N1CCC(O)CN1CCN(c2cccc(Cl)c2Cl)CC1]

1-(2,3-dichlorophenyl)piperazine hydrochloride (1.38 mmol, 369 mg) in 2-PrOH (15 mL) was stirred with INTERMEDIATE 32 (300 mg, 1.38 mmol) in presence of Et$_3$N (0.4 mL, 2.76 mmol) at 60° C. for 6 h, then at room temperature overnight. The crude was evaporated and the residue was adsorbed on silica gel and purified by column chromatography (Eluent: cyclohexane/ethyl acetate). The organic fractions were collected and evaporated in vacuo. Yellow oil 350 mg (57%). $^1$H NMR (400 MHz, Chloroform-d) δ 7.86 (dd, J=3.05, 5.42 Hz, 2H), 7.73 (dd, J=3.04, 5.45 Hz, 2H), 7.20-7.12 (m, 2H), 6.97 (dd, J=2.79, 6.76 Hz, 1H), 3.10 (d, J=24.5 Hz, 8H), 2.61 (d, J=6.4 Hz, 1H), 2.50-2.34 (m, 3H), 1.86-1.74 (m, 3H).

Intermediate 34. 2-[3-hydroxy-4-[4-(2-methoxyphenyl)piperazin-1-yl]butyl]isoindoline-1,3-dione

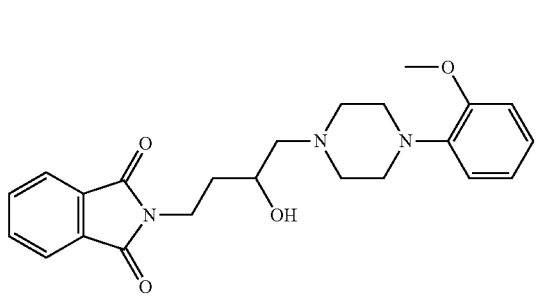 [SMILES: COc1ccccc1N1CCN(CC(O)CCN2C(=O)c3ccccc3C2=O)CC1]

1-(2-methoxyphenyl)piperazine hydrochloride (1.84 mmol, 421 mg) in 2-PrOH (15 mL) was reacted in the microwave (100° C., 90 min) with INTERMEDIATE 32 (400 mg, 1.84 mmol) in presence of Et$_3$N (0.5 mL, 3.68 mmol). The crude was evaporated and the residue was adsorbed on silica gel and purified by column chromatography (Eluent: cyclohexane/ethyl acetate). The organic fractions were collected and evaporated in vacuo. Yellow oil 409 mg (54%). $^1$H NMR (400 MHz, Chloroform-d) δ 7.86 (dd, J=5.5, 3.0 Hz, 2H), 7.76-7.68 (m, 2H), 7.00 (ddd, J=7.9, 5.7, 3.4 Hz, 1H), 6.95-6.89 (m, 2H), 6.89-6.82 (m, 1H), 3.86 (s, 3H), 3.10 (d, J=24.5 Hz, 4H), 2.89 (d, J=0.6 Hz, 6H), 2.61 (d, J=6.4 Hz, 1H), 2.50-2.34 (m, 2H), 1.86-1.74 (m, 2H).

Intermediate 35. 2-[4-[4-(2,3-dichlorophenyl)piperazin-1-yl]-3-fluoro-butyl]isoindoline-1,3-dione

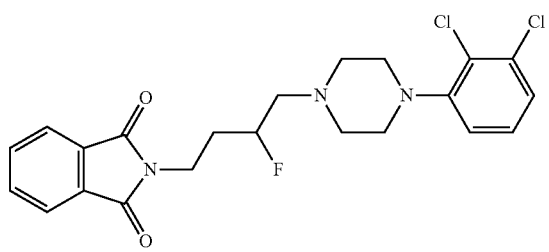 [SMILES: O=C1c2ccccc2C(=O)N1CCC(F)CN1CCN(c2cccc(Cl)c2Cl)CC1]

To a solution of DeOxo-Fluor® (0.58 mL, 2.68 mmol) in dry DCM (10 mL) at −8° C., INTERMEDIATE 33 (300 mg, 0.67 mmol) was added. This reaction mixture was continuously stirred for 72 hours at room temperature. The reaction mixture was diluted with DCM and washed with water and NaHCO$_3$ ss, and the organic layer was dried over Na$_2$SO$_4$. The solvent was removed under vacuum to afford the crude, which was further purified by column chromatography on silica gel (Eluent: Cyclohexane/ethyl acetate 1:1). The organic fractions were collected and the solvent was removed under reduced pressure. Yellow oil 150 mg (50%). $^1$H NMR (400 MHz, Chloroform-d) δ 7.88 (ddd, J=5.4, 4.7, 3.0 Hz, 2H), 7.76 (ddd, J=9.7, 5.5, 3.0 Hz, 2H), 7.19-7.12 (m, 1H), 6.96 (dd, J=6.6, 3.0 Hz, 1H), 4.96-4.70 (m, 1H), 3.97-3.83 (m, 2H), 3.07 (m, 4H), 2.82-2.69 (m, 4H), 2.67-2.48 (m, 1H), 2.35-2.19 (m, 1H), 2.19-1.94 (m, 2H).

Intermediate 36. 2-[3-fluoro-4-[4-(2-methoxyphenyl)piperazin-1-yl]butyl]isoindoline-1,3-dione

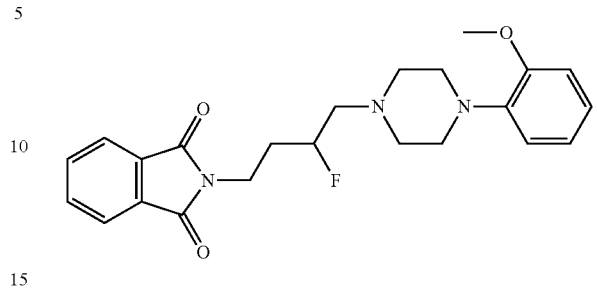

To a solution of DeOxo-Fluor® (0.64 mL, 2.93 mmol) in dry DCM (10 mL) at −8° C., INTERMEDIATE 34 (300 mg, 0.73 mmol) was added. This reaction mixture was continuously stirred for 72 hours at room temperature. The reaction mixture was diluted with DCM and washed with water and NaHCO$_3$ ss, and the organic layer was dried over Na$_2$SO$_4$. The solvent was removed under vacuum to afford the crude, which was further purified by column chromatography on silica gel (Eluent: Cyclohexane/ethyl acetate 1:1). The organic fractions were collected and the solvent was removed under reduced pressure. Yellow oil 200 mg (66%). $^1$H NMR (400 MHz, Chloroform-d) δ 7.91-7.83 (m, 2H), 7.74 (dd, J=5.4, 3.0 Hz, 2H), 7.02 (ddd, J=7.8, 6.1, 2.9 Hz, 1H), 6.97-6.91 (m, 2H), 6.91-6.84 (m, 1H), 4.82 (dddd, J=49.9, 11.1, 7.1, 3.3 Hz, 1H), 3.91 (dd, J=7.1, 2.4 Hz, 2H), 3.88 (s, 3H), 3.10 (s, 4H), 2.82-2.69 (m, 5H), 2.67-2.49 (m, 1H), 2.21-2.07 (m, 1H), 1.65 (m, 1H).

Intermediate 37. 4-[4-(2,3-dichlorophenyl)piperazin-1-yl]-3-fluoro-butan-1-amine

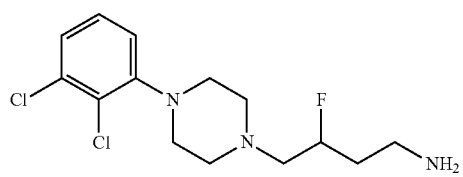 [SMILES: NCCC(F)CN1CCN(c2cccc(Cl)c2Cl)CC1]

The title compound was synthesized applying the general procedure III step B using INTERMEDIATE 35 (150 mg, 0.33 mmol) and hydrazine hydrate (0.02 mL, 0.40 mmol) in 4 mL of methanol, then 2 mL of HCl. Yellow oil 80 mg (75%). $^1$H NMR (400 MHz, Chloroform-d) δ 7.19-7.12 (m, 1H), 6.96 (dd, J=6.6, 3.0 Hz, 1H), 4.96-4.70 (m, 1H), 3.97-3.83 (m, 2H), 3.07 (m, 4H), 2.82-2.69 (m, 4H), 2.67-2.48 (m, 1H), 2.35-2.19 (m, 1H), 2.19-1.94 (m, 2H).

Intermediate 38. 3-fluoro-4-[4-(2-methoxyphenyl)piperazin-1-yl]butan-1-amine

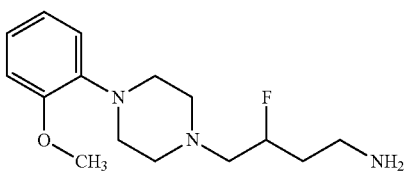 [SMILES: COc1ccccc1N1CCN(CC(F)CCN)CC1]

The title compound was synthesized applying the general procedure III step B using INTERMEDIATE 36 (200 mg, 0.49 mmol) and hydrazine hydrate (0.03 mL, 0.58 mmol) in 4 mL of methanol, then 2 mL of HCl. Yellow oil 130 mg (95%). ¹H NMR (400 MHz, Chloroform-d) δ 7.02 (ddd, J=7.7, 6.7, 2.3 Hz, 1H), 6.99-6.92 (m, 2H), 6.88 (dd, J=8.0, 1.3 Hz, 1H), 4.88 (dddd, J=50.4, 11.6, 7.2, 3.3 Hz, 1H), 3.88 (s, 3H), 3.13 (s, 4H), 2.98-2.84 (m, 2H), 2.84-2.69 (m, 5H), 2.56 (ddd, J=30.8, 13.9, 2.9 Hz, 1H), 1.96-1.64 (m, 2H).

Intermediate 39.
3-(4-hydroxy-2-methoxy-phenyl)benzamide

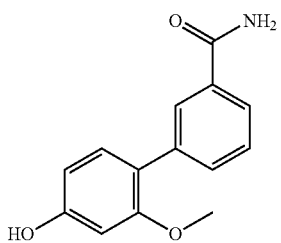 [SMILES: COc1cc(O)ccc1-c1cccc(C(N)=O)c1]

A 50 ml flask containing a magnetic stir bar was charged with PdCl₂(dppf) (21 mg, 0.03 mmol), 3-benzamideboronic acid (365 mg, 2.22 mmol), K₂CO₃ (612 mg, 4.43 mmol) and 4-bromo-3-methoxy-phenol (300 mg, 1.48 mmol). The entire solid were dissolved in a 3:1 mixture of dioxane and water (4 mL) and the reaction mixture was vigorously stirred at 90° C. for 3 hrs. The reaction mixture was diluted with water and acidified with HCl 2N and extracted with DCM. The organic phase was collected and evaporated in vacuo. The crude was purified by column chromatography on silica gel (Eluent: Cyclohexane/ethyl acetate). The organic fractions were collected and evaporated in vacuo. Yellowish oil 100 mg (28%). ¹H NMR (400 MHz, Chloroform-d) δ 8.19 (t, J=2.0 Hz, 1H), 7.73 (dt, J=7.5, 2.0 Hz, 1H), 7.66 (dt, J=7.5, 2.0 Hz, 1H), 7.50 (t, J=7.4 Hz, 1H), 7.41 (d, J=7.5 Hz, 1H), 7.00 (s, 1H), 6.68 (d, J=2.1 Hz, 1H), 6.64 (dd, J=7.5, 2.0 Hz, 1H), 6.21 (s, 2H), 3.90 (s, 3H).

Intermediate 40. 2-[3-[4-(2,3-dichlorophenyl)piperazin-1-yl]-2-hydroxy-propyl]isoindoline-1,3-dione

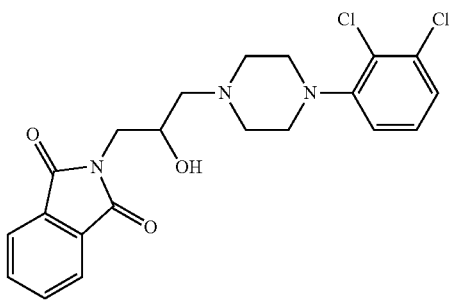 [SMILES: O=C1c2ccccc2C(=O)N1CC(O)CN1CCN(c2cccc(Cl)c2Cl)CC1]

1-(2,3-dichlorophenyl)piperazine monohydrochloride (1185 mg, 4.43 mmol) in 2-PrOH (10 mL) was reacted in the microwave (pressure vessel, Pmax, 200 W, cooling, 100° C., 90 min) with N-(2,3-Epoxypropyl)phthalimide (900 mg, 4.43 mmol) in presence of Et₃N (1.2 mL, 8.86 mmol). The crude was filtered and the residue was washed with water. White solid 1900 mg (99%). ¹H NMR (400 MHz, Chloroform-d) δ 7.92-7.84 (m, 2H), 7.75 (dd, J=5.5, 3.0 Hz, 2H), 7.21-7.11 (m, 2H), 6.99-6.92 (m, 1H), 4.11 (ddt, J=9.1, 7.0, 4.5 Hz, 1H), 3.90-3.75 (m, 2H), 3.14-2.99 (m, 4H), 2.84 (dt, J=10.1, 4.7 Hz, 2H), 2.66 (d, J=8.4 Hz, 2H), 2.61-2.46 (m, 2H).

Intermediate 41. 2-[2-[4-(2,3-dichlorophenyl)piperazin-1-yl]-3-fluoro-propyl]isoindoline-1,3-dione

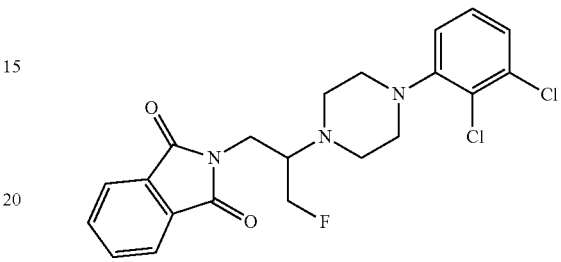

This intermediate was obtained through fluorination of INTERMEDIATE 40 with DeOxo-Fluor®. Its preparation involves the 1,2-migration of 1,3-bifunctionalized amino-2-propanol into 1,2-bifunctionalised amino-1-fluoromethylene, analogously to similar rearrangements observed with DAST which had been described by Ji-Wang Chem et al, Tetrahedron Letters, 1998, 39: 8483-8486.

To a solution of DeOxo-Fluor® (1.40 mL, 6.45 mmol) in dry DCM (10 mL) at −8° C., INTERMEDIATE 40 (700 mg, 1.61 mmol) was added. This reaction mixture was continuously stirred for 24 hours at room temperature. The reaction mixture was diluted with DCM and washed with water and NaHCO3 ss, and the organic layer was dried over Na2SO4. The solvent was removed under vacuum to afford the crude, which was further purified by column chromatography on silica gel (Eluent: Cyclohexane/ethyl acetate 1:1). The organic fractions were collected and the solvent was removed under reduced pressure. Yellow oil 303 mg (43%). ¹H NMR (400 MHz, Chloroform-d) δ 7.94-7.85 (m, 2H), 7.79-7.73 (m, 2H), 7.18-7.08 (m, 2H), 6.88 (dd, J=7.5, 2.1 Hz, 1H), 4.83-4.56 (m, 2H), 4.18-4.04 (m, 1H), 3.72 (dd, J=14.1, 5.8 Hz, 1H), 3.41-3.26 (m, 1H), 3.09 (dt, J=10.1, 4.7 Hz, 2H), 2.93 (s, 4H), 2.74 (dt, J=9.9, 4.6 Hz, 2H).

Intermediate 42. 2-[4-(2,3-dichlorophenyl)piperazin-1-yl]-3-fluoro-propan-1-amine

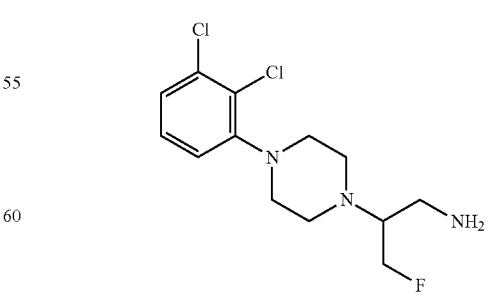

The title compound was synthesized applying the general procedure III step B using INTERMEDIATE 41 (300 mg, 0.69 mmol) and hydrazine hydrate (0.04 mL, 0.83 mmol) in 4 mL of methanol, then 2 mL of HCl. Yellow oil 157 mg (75%). $^1$H NMR (400 MHz, Chloroform-d) δ 7.20-7.14 (m, 2H), 6.97 (dd, J=6.7, 2.9 Hz, 1H), 4.75-4.54 (m, 2H), 3.15-2.72 (m, 7H), 1.55 (s, 4H).

Example 1. [3-(3-carbamoylphenyl)phenyl] N-[4-[4-(2-methoxyphenyl)piperazin-1-yl]butyl] carbamate The title compound was synthesized according to the general procedure Ia Method A, starting from di-tert-butyl-dicarbonate (153.1 mg, 0.70 mmol), 4-dimethylaminopyridine (61.2 mg, 0.50 mmol) amine INTERMEDIATE 5 (132.0 mg, 0.50 mmol) and phenol INTERMEDIATE 9 (149.6 mg, 0.70 mmol) in acetonitrile (4 mL). White solid 51 mg (20%). UPLC-MS (method A): Rt 1.90 min; m/z 503 [M–H]$^+$. $^1$H NMR (400 MHz, DMSO-d$_6$) δ 8.19-8.10 (m, 2H), 7.92-7.79 (m, 3H), 7.62-7.36 (m, 5H), 7.17-7.10 (m, 1H), 6.99-6.81 (m, 4H), 3.77 (s, 3H), 3.12 (q, J=6.16, 6.56 Hz, 2H), 2.98 (m, 4H), 2.56 (m, 4H), 2.40 (m, 2H), 1.54 (m, 4H).

Example 2. [3-(3-carbamoylphenyl)phenyl] N-[4-[4-(2,3-dichlorophenyl)piperazin-1-yl]butyl] carbamate The title compound was synthesized according to the general procedure Ia Method A, starting from di-tert-butyl-dicarbonate (50.5 mg, 0.23 mmol), 4-dimethylaminopyridine (20.2 mg, 0.17 mmol), amine INTERMEDIATE 6 (50.0 mg, 0.17 mmol) and phenol INTERMEDIATE 9 (49.4 mg, 0.23 mmol) in acetonitrile (4 mL). White solid 51 mg (57%). UPLC-MS (method A): Rt 2.36 min; m/z 541 [M–H]$^+$. $^1$H NMR (400 MHz, DMSO-d$_6$) δ 8.19-8.11 (m, 2H), 7.91-7.80 (m, 3H), 7.62-7.42 (m, 5H), 7.35-7.26 (m, 2H), 7.19-7.07 (m, 2H), 3.12 (d, J=6.19 Hz, 2H), 2.99 (s, 4H), 2.55 (s, 4H), 2.38 (d, J=6.39 Hz, 2H), 1.56-1.49 (m, 4H).

Example 3. [3-(3-carbamoylphenyl)phenyl] N-[3-[4-(2,3-dichlorophenyl)piperazin-1-yl]propyl]carbamate The title compound was synthesized according to the general procedure Ia Method A, starting from di-tert-butyl-dicarbonate (95.4 mg, 0.44 mmol), 4-dimethylaminopyridine (38.1 mg, 0.31 mmol), amine INTERMEDIATE 7 (90 mg, 0.31 mmol) and the phenol INTERMEDIATE 9 (79.9 mg, 0.37 mmol) in acetonitrile (4 mL). White solid 45 mg (27%). UPLC-MS (method A): Rt 2.44 min; m/z 527 [M–H]$^+$. $^1$H NMR (400 MHz, DMSO-d$_6$) δ 8.17 (m, 1H), 8.12 (m, 1H), 7.92-7.84 (m, 1H), 7.84 (m, 2H), 7.62-7.45 (m, 4H), 7.41 (m, 1H), 7.30 (q, J=3.71, 4.39 Hz, 2H), 7.20-7.08 (m, 2H) 3.16 (q, J=6.51 Hz, 2H), 3.00 (t, J=4.84 Hz, 4H), 2.56 (m, 4H), 2.42 (t, J=7.04 Hz, 2H), 1.69 (p, J=6.95 Hz, 2H).

Example 4. [3-(3-carbamoylphenyl)phenyl] N-[3-(4-phenylpiperazin-1-yl)propyl]carbamate The title compound was synthesized according to the general procedure Ia Method A, starting from di-tert-butyl-dicarbonate (167.2 mg, 0.77 mmol), 4-dimethylaminopyridine (66.8 mg, 0.55 mmol), amine INTERMEDIATE 8 (120.0 mg, 0.55 mmol) and the phenol INTERMEDIATE 9 (140.0 mg, 0.66 mmol) in acetonitrile (4 mL). White solid 40 mg (16%). UPLC-MS (method A): Rt 1.94 min; m/z 459 [M–H]$^+$. $^1$H NMR (400 MHz, DMSO-d$_6$) δ 8.16 (t, J=1.7 Hz, 1H), 8.15-8.10 (m, 1H), 7.88 (dt, J=7.8, 1.4 Hz, 1H), 7.86 (m, 2H), 7.62-7.45 (m, 4H), 7.46-7.39 (m, 1H), 7.26-7.15 (m, 2H), 7.14 (ddd, J=8.0, 2.3, 1.0 Hz, 1H), 6.97-6.89 (m, 2H), 6.77 (tt, J=7.2, 1.0 Hz, 1H), 3.11-3.19 (m, 6H), 2.57-2.52 (m, 4H), 2.40 (t, J=7.1 Hz, 2H), 1.75-1.64 (m, 2H).

Example 5. (3-phenylphenyl) N-[3-(4-phenylpiperazin-1-yl)propyl]carbamate

The title compound was synthesized according to the general procedure Ia Method A, starting from di-tert-butyl-dicarbonate (206.2 mg, 0.94 mmol), 4-dimethylaminopyridine (82.4 mg, 0.67 mmol), amine INTERMEDIATE 8 (148.0 mg, 0.67 mmol) and the phenol INTERMEDIATE 10 (137.8 mg, 0.81 mmol) in acetonitrile (4 mL). White solid 66 mg (24%). UPLC-MS (method A): Rt 2.66 min; m/z 416 [M–H]$^+$. $^1$H NMR (400 MHz, DMSO-d$_6$) δ 7.81 (t, J=5.7 Hz, 1H), 7.71-7.64 (m, 2H), 7.56-7.44 (m, 4H), 7.42-7.31 (m, 2H), 7.25-7.17 (m, 2H), 7.13 (dddd, J=11.4, 7.7, 2.4, 1.2 Hz, 1H), 6.97-6.89 (m, 2H), 6.77 (tt, J=7.2, 1.0 Hz, 1H), 3.20-3.09 (m, 6H), 2.53-2.50 (m, 4H), 2.39 (q, J=6.7 Hz, 2H), 1.70 (p, J=7.0 Hz, 2H).

Example 6. [4-(3-carbamoylphenyl)phenyl] N-[3-[4-(2,3-dichlorophenyl)piperazin-1-yl]propyl]carbamate The title compound was synthesized according to the general procedure Ia Method A, starting from di-tert-butyl-dicarbonate (84.8 mg, 0.39 mmol), 4-dimethylaminopyridine (33.9 mg, 0.28 mmol), amine INTERMEDIATE 7 (80.0 mg, 0.28 mmol) and the phenol INTERMEDIATE 11 (82.9 mg, 0.39 mmol) in acetonitrile (4 mL). White solid 34 mg (23%). UPLC-MS (method A): Rt 2.34 min; m/z 527 [M–H]$^+$. $^1$H NMR (400 MHz, DMSO-d$_6$) δ 8.15 (t, J=1.7 Hz, 1H), 8.09 (s, 1H), 7.86 (dt, J=7.7, 1.4 Hz, 1H), 7.84-7.78 (m, 2H), 7.78-7.70 (m, 2H), 7.55 (t, J=7.7 Hz, 1H), 7.41 (s, 1H), 7.35-7.27 (m, 2H), 7.27-7.20 (m, 2H), 7.16 (dd, J=6.6, 3.0 Hz, 1H), 3.15 (q, J=6.6 Hz, 2H), 3.05-2.97 (m, 4H), 2.57 (s, 4H), 2.43 (t, J=7.0 Hz, 2H), 1.70 (q, J=7.0 Hz, 2H).

Example 7. [4-(3-carbamoylphenyl)phenyl] N-[4-[4-(2,3-dichlorophenyl)piperazin-1-yl]butyl]carbamate The title compound was synthesized according to the general procedure Ia Method A, starting from di-tert-butyl-dicarbonate (80.9 mg, 0.37 mmol), 4-dimethylaminopyridine (32.3 mg, 0.26 mmol), amine INTERMEDIATE 6 (80.0 mg, 0.26 mmol) and the phenol INTERMEDIATE 11 (79.0 mg, 0.37 mmol) in acetonitrile (4 mL). White solid 59 mg (41%). UPLC-MS (method A): Rt 2.32 min; m/z 541 [M–H]$^+$. $^1$H NMR (400 MHz, DMSO-d$_6$) δ 8.15 (t, J=1.8 Hz, 1H), 8.09 (s, 1H), 7.83 (dddd, J=17.5, 7.8, 2.3, 1.2 Hz, 3H), 7.78-7.70 (m, 2H), 7.55 (t, J=7.7 Hz, 1H), 7.41 (s, 1H), 7.34-7.27 (m, 2H), 7.26-7.19 (m, 2H), 7.15 (dd, J=6.5, 3.1 Hz, 1H), 3.12 (q, J=6.3 Hz, 2H), 3.00 (d, J=5.0 Hz, 4H), 2.56 (s, 4H), 2.39 (d, J=6.8 Hz, 2H), 1.60-1.47 (m, 4H).

Example 8. (3-morpholinophenyl) N-[4-[4-(2,3-dichlorophenyl)piperazin-1-yl]butyl] carbamate hydrochloride The title compound was synthesized according to the general procedure Ia Method A, starting from di-tert-butyl-dicarbonate (101.1 mg, 0.46 mmol), 4-dimethylaminopyridine (40.4 mg, 0.33 mmol), amine INTERMEDIATE 6 (100.0 mg, 0.33 mmol) and 3-morpholino phenol (83.0 mg, 0.46 mmol) in acetonitrile (4 mL). The resultant oil was dissolved in a small amount of diethyl ether, to which 2M HCl in diethyl ether was added and the title compound was isolated as hydrochloride salt. White solid 30 mg (17%). UPLC-MS (method A): Rt 2.44 min; m/z 507 [M−H]$^+$. $^1$H NMR (400 MHz, DMSO-d$_6$) δ 11.06-10.87 (m, 1H), 7.75 (t, J=5.6 Hz, 1H), 7.37 (d, J=7.0 Hz, 2H), 7.27-7.14 (m, 2H), 6.77 (dd, J=8.2, 2.6 Hz, 1H), 6.64 (s, 1H), 6.54 (d, J=8.1 Hz, 1H), 3.81-3.65 (m, 4H), 3.57 (d, J=10.5 Hz, 2H), 3.43 (d, J=11.2 Hz, 2H), 3.19 (dd, J=17.0, 10.1 Hz, 7H), 3.10 (t, J=5.0 Hz, 5H), 1.92-1.67 (m, 2H), 1.53 (p, J=7.4 Hz, 2H).

Example 9. [3-(4,4-difluoro-1-piperidinyl)phenyl] N-[4-[4-(2,3-dichlorophenyl)piperazin-1-yl] butyl] carbamate hydrochloride The title compound was synthesized according to the general procedure Ia Method A, starting from di-tert-butyl-dicarbonate (80.9 mg, 0.37 mmol), 4-dimethylaminopyridine (32.4 mg, 0.26 mmol), amine INTERMEDIATE 6 (100.0 mg, 0.33 mmol) and INTERMEDIATE 12 (62.1 mg, 0.29 mmol) in acetonitrile (4 mL). The resultant oil was dissolved in a small amount of diethyl ether, to which 2M HCl in diethyl ether was added and the title compound was isolated as hydrochloride salt. White solid 57 mg (37%). UPLC-MS (method A): Rt 2.87 min; m/z 541 [M−H]$^+$. $^1$H NMR (400 MHz, DMSO-d$_6$) δ 10.77 (s, 1H), 7.73 (t, J=5.5 Hz, 1H), 7.44-7.28 (m, 2H), 7.20 (t, J=8.2 Hz, 2H), 6.83 (dd, J=8.2, 2.4 Hz, 1H), 6.71 (t, J=2.1 Hz, 1H), 6.53 (dd, J=7.9, 2.0 Hz, 1H), 3.35 (s, 3H), 3.10 (q, J=6.4 Hz, 7H), 2.03 (tt, J=14.1, 5.7 Hz, 5H), 1.56 (tt, J=18.5, 11.3 Hz, 5H), 1.92-1.67 (m, 2H), 1.53 (p, J=7.4 Hz, 2H).

Example 10. [4-(3-carbamoylphenyl)phenyl] N-[4-[4-(2-methoxyphenyl)piperazin-1-yl]butyl] carbamate The title compound was synthesized according to the general procedure Ia Method B, starting from p-nitrophenylchloroformate (84.2 mg, 0.42 mmol), DIPEA (0.15 mL, 0.84 mmol), amine INTERMEDIATE 5 (100.0 mg, 0.38 mmol) and INTERMEDIATE 11 (101.2 mg, 0.47 mmol) in a 1:1 mixture of DMA:DCM (4 mL). White solid 50 mg (26%). UPLC-MS (method A): Rt 1.86 min; m/z 503 [M−H]$^+$. $^1$H NMR (400 MHz, DMSO-d$_6$) δ 8.15 (t, J=1.7 Hz, 1H), 8.09 (s, 1H), 7.88-7.78 (m, 3H), 7.77-7.69 (m, 2H), 7.54 (t, J=7.7 Hz, 1H), 7.41 (s, 1H), 7.25-7.18 (m, 2H), 6.97-6.82 (m, 4H), 3.77 (s, 3H), 3.11 (t, J=6.2 Hz, 2H), 2.96-3.02 (m, 4H), 2.56-2.51 (m, 4H), 2.36 (t, J=6.8 Hz, 2H), 1.60-1.44 (m, 4H).

Example 11. [4-(3-carbamoylphenyl)phenyl] N-[3-[4-(2-methoxyphenyl)piperazin-1-yl] propyl]carbamate The title compound was synthesized according to the general procedure Ia Method B, starting from p-nitrophenylchloroformate (103.8 mg, 0.52 mmol), DIPEA (0.15 mL, 0.84 mmol), amine INTERMEDIATE 14 (70.0 mg, 0.47 mmol) and INTERMEDIATE 11 (99.9 mg, 0.47 mmol) in a 1:1 mixture of DMA:DCM (4 mL). White solid 22 mg (10%). UPLC-MS (method A): Rt 1.83 min; m/z 489 [M−H]$^+$. $^1$H NMR (400 MHz, DMSO-d$_6$) δ 8.15 (t, J=1.7 Hz, 1H), 8.10 (s, 1H), 7.86 (dt, J=7.8, 1.4 Hz, 1H), 7.84-7.78 (m, 2H), 7.78-7.70 (m, 2H), 7.55 (t, J=7.7 Hz, 1H), 7.42 (s, 1H), 7.27-7.19 (m, 2H), 6.99-6.91 (m, 2H), 6.91-6.84 (m, 2H), 3.78 (s, 3H), 3.15 (t, J=6.6 Hz, 2H), 2.97 (s, 4H), 2.53 (s, 4H), 2.40 (t, J=7.1 Hz, 2H), 1.69 (p, J=7.2 Hz, 2H).

Example 12. [4-(4,4-difluoro-1-piperidinyl)phenyl] N-[4-[4-(2,3-dichlorophenyl)piperazin-1-yl]butyl] carbamate hydrochloride The title compound was synthesized according to the general procedure Ia Method A, starting from di-tert-butyl-dicarbonate (63.5 mg, 0.29 mmol), 4-dimethylaminopyridine (35.6 mg, 0.29 mmol) amine INTERMEDIATE 6 (80.0 mg, 0.26 mmol) and phenol INTERMEDIATE 15 (62.1 mg, 0.29 mmol) in acetonitrile (4 mL). The resultant oil was dissolved in a small amount of diethyl ether, to which 2M HCl in diethyl ether was added. Evaporation of the solvent produced the title compound as yellow solid 19 mg (12%). UPLC-MS (method A): Rt 2.83 min; m/z 541 [M−H]$^+$. $^1$H NMR (400 MHz, DMSO-d$_6$) δ 11.17 (d, J=11.2 Hz, 1H), 7.75 (t, J=5.4 Hz, 1H), 7.36 (d, J=6.0 Hz, 2H), 7.20 (d, J=7.1 Hz, 1H), 7.14 (d, J=8.1 Hz, 2H), 7.02 (d, J=7.4 Hz, 2H), 3.49-3.29 (m, 7H), 3.29-3.02 (m, 9H), 2.04-2.26 (m, 4H), 1.70-1.88 (m, 2H), 1.61-1.43 (m, 2H).

Example 13. (3-morpholino phenyl) N-[3-[4-(o-tolyl)piperazin-1-yl]propyl]carbamate hydrochloride The title compound was synthesized according to the general procedure Ia Method A, starting from di-tert-butyl-dicarbonate (51.4 mg, 0.24 mmol), 4-dimethylaminopyridine (26.2 mg, 0.21 mmol) amine INTERMEDIATE 21 (50.0 mg, 0.21 mmol) and commercially available 3-morpholino phenol (42.2 mg, 0.24 mmol) in acetonitrile (4 mL). The resultant oil was dissolved in a small amount of diethyl ether, to which 2M HCl in diethyl ether was added. Evaporation of the solvent produced the title compound as yellow solid 25 mg (25%). UPLC-MS (method A): Rt 2.15 min; m/z 439 [M−H]$^+$.

Example 14. [3-(3-carbamoylphenyl)phenyl] N-[4-(4-phenyl-1-piperidinyl)butyl]carbamate hydrochloride The title compound was prepared according to the general procedure Ia. Starting from di-tert butyl carbonate (135 mg, 0.62 mmol), 4-dimethylaminopyridine (63 mg, 0.52 mmol), amine INTERMEDIATE 19 (120 mg, 0.52 mmol), INTERMEDIATE 9 (154 mg, 0.72 mmol) in MeCN (5 mL). The title compound (white solid) was isolated as HCl salt base after chromatographic purification. 54 mg (22%), UPLC-MS (method A): Rt 1.97 min, m/z 472 [M+H]$^+$. $^1$H NMR (400 MHz, DMSO-d$_6$) δ 9.30 (s, 1H), 8.16 (s, 1H), 7.92-7.85 (m, 2H), 7.82 (d, J=8.0 Hz, 1H), 7.61-7.44 (m, 4H), 7.38-7.30 (m, 2H), 7.23 (dt, J=7.0, 2.9 Hz, 3H), 7.13 (dd, J=7.6, 1.8 Hz, 1H), 3.59 (d, J=11.6 Hz, 2H), 3.22-2.91 (m, 6H), 2.83 (t, J=12.0 Hz, 1H), 2.01 (d, J=13.3 Hz, 2H), 1.89 (q, J=12.8 Hz, 2H), 1.76 (s, 2H), 1.65-1.48 (m, 2H).

Example 15. (4-phenylphenyl) N-[3-[4-(o-tolyl)piperazin-1-yl]propyl]carbamate

The title compound was prepared according to the general procedure Ia. Starting from di-tert butyl carbonate (66 mg, 0.30 mmol). 4-dimethylaminopyridine (31 mg, 0.25 mmol), amine INTERMEDIATE 21 (59 mg, 0.25 mmol), 4-phenyl-phenol (52 mg, 0.30 mmol) in MeCN (3 mL). The title compound (white solid) was isolated as free base after chromatographic purification. 63 mg (58%). UPLC-MS (method A): Rt 2.77 min, m/z 430 [M+H]$^+$. $^1$H NMR (400 MHz, DMSO-d$_6$) δ 7.81 (t, J=5.6 Hz, 1H), 7.70-7.62 (m, 4H), 7.47 (t, J=7.6 Hz, 2H), 7.41-7.32 (m, 1H), 7.24-7.10 (m, 4H), 7.05-6.90 (m, 2H), 3.15 (q, J=6.7 Hz, 2H), 2.85 (t, J=4.3 Hz, 4H), 2.55 (s, 4H), 2.42 (t, J=6.9 Hz, 2H), 2.25 (s, 3H), 1.69 (p, J=7.0 Hz, 2H).

Example 16. (4-phenylphenyl) N-[3-[4-[2-(trifluoromethyl)phenyl]piperazin-1-yl]propyl] carbamate The title compound was prepared according to the general procedure Ia. Starting from di-tert butyl carbonate (66 mg, 0.30 mmol). 4-dimethylaminopyridine (31 mg, 0.25 mmol), amine INTERMEDIATE 20 (70 mg, 0.25 mmol), 4-phenylphenol (52 mg, 0.30 mmol) in MeCN (3 mL). The title compound (colourless oil) was isolated as free base after chromatographic purification. 78 mg (66%). UPLC-MS (method A): Rt 2.93 min, m/z 484 [M+H]$^+$. $^1$H NMR (400 MHz, DMSO-d$_6$) δ 7.81 (t, J=5.6 Hz, 1H), 7.70-7.61 (m, 6H), 7.56 (d, J=7.8 Hz, 1H), 7.50-7.43 (m, 2H), 7.41-7.28 (m, 2H), 7.25-7.17 (m, 2H), 3.15 (q, J=6.7 Hz, 2H), 2.89 (t, J=4.6 Hz, 4H), 2.55-2.48 (m, 4H), 2.41 (t, J=7.1 Hz, 2H), 1.69 (p, J=7.0 Hz, 2H).

Example 17. 9H-carbazol-2-yl N-[3-[4-(2,3-dichlorophenyl)piperazin-1-yl]propyl]carbamate The title compound was prepared according to the general procedure Ia. Starting from di-tert butyl carbonate (73 mg, 0.33 mmol). 4-dimethylaminopyridine (34 mg, 0.28 mmol), amine INTERMEDIATE 7 (80 mg, 0.28 mmol), 2-hydroxycarbazole (61 mg, 0.33 mmol) in MeCN (3 mL). The title compound (off-white solid) was isolated as free base after chromatographic purification. 14 mg (10%). UPLC-MS (method A): Rt 2.88 min, m/z 497 [M+H]$^+$. $^1$H NMR (400 MHz, DMSO-d$_6$) δ 11.24 (s, 1H), 8.07 (t, J=8.3 Hz, 2H), 7.76 (t, J=5.6 Hz, 1H), 7.48 (d, J=8.1 Hz, 1H), 7.40-7.27 (m, 3H), 7.20 (d, J=2.0 Hz, 1H), 7.19-7.13 (m, 2H), 6.89 (dd, J=8.4, 2.1 Hz, 1H), 3.16 (q, J=6.7, 6.0 Hz, 2H), 3.01 (s, 4H), 2.57 (s, 4H), 2.44 (t, J=7.0 Hz, 2H), 1.71 (p, J=6.9 Hz, 2H).

Example 18. [4-(4,4-difluoro-1-piperidinyl)phenyl] N-[3-[4-[2-(trifluoromethyl)phenyl] piperazin-1-yl] propyl]carbamate hydrochloride The title compound was prepared according to the general procedure Ia. Starting from di-tert butyl carbonate (64 mg, 0.29 mmol), 4-dimethylaminopyridine (36 mg, 0.29 mmol), amine INTERMEDIATE 20 (77 mg, 0.27 mmol), INTERMEDIATE 15 (63 mg, 0.29 mmol) in MeCN (3 mL). The oil was dissolved in a small amount of 1,4-dioxane, to which 4M HCl in 1,4-dioxane was added. Evaporation of the solvent produced the title compound as white solid. 21 mg (14%). UPLC-MS (method A): Rt 2.74 min, m/z 527 [M+H]$^+$. $^1$H NMR (400 MHz, DMSO-d6) δ 10.97 (s, 1H), 7.81 (t, J=5.7 Hz, 1H), 7.72 (d, J=7.7 Hz, 2H), 7.56 (d, J=8.1 Hz, 1H), 7.42 (t, J=7.6 Hz, 1H), 7.10 (d, J=8.6 Hz, 2H), 7.02 (d, J=9.0 Hz, 2H), 3.33 (q, J=7.2, 6.8 Hz, 6H), 3.27-3.02 (m, 10H), 2.13 (tt, J=13.9, 5.7 Hz, 4H), 1.96 (p, J=6.7 Hz, 2H).

Example 19. [4-(3-carbamoylphenyl)phenyl] N-[(E)-4-[4-(2,3-dichlorophenyl)piperazin-1-yl] but-2-enyl]carbamate The title compound was prepared according to the general procedure Ia starting from di-tert butyl carbonate (102 mg, 0.47 mmol), 4-dimethylaminopyridine (49 mg, 0.40 mmol), amine INTERMEDIATE 24 (100 mg, 0.33 mmol), biphenyl INTERMEDIATE 11 (78 mg, 0.37 mmol) in MeCN (3 mL). White solid 28 mg (16%). UPLC-MS (method A): Rt 2.36 min, m/z 539 [M+H]$^+$. $^1$H NMR (400 MHz, DMSO-d$_6$) δ 8.15 (t, J=1.8 Hz, 1H), 8.13-8.07 (m, 1H), 8.00 (t, J=5.7 Hz, 1H), 7.86 (dt, J=7.8, 1.4 Hz, 1H), 7.83-7.79 (m, 1H), 7.78-7.70 (m, 2H), 7.55 (t, J=7.7 Hz, 1H), 7.42 (s, 1H), 7.30 (q, J=5.2, 4.6 Hz, 2H), 7.26-7.20 (m, 2H), 7.15 (dd, J=6.7, 3.0 Hz, 1H), 5.68 (t, J=2.5 Hz, 2H), 3.77-3.69 (m, 2H), 3.01 (q, J=4.7 Hz, 6H), 2.56 (s, 4H).

Example 20. [4-(3-carbamoylphenyl)-3-fluoro-phenyl] N-[(E)-4-[4-(2,3-dichlorophenyl) piperazin-1-yl]but-2-enyl]carbamate The title compound was prepared according to the general procedure Ia starting from di-tert butyl carbonate (102 mg, 0.47 mmol), 4-dimethylaminopyridine (49 mg, 0.40 mmol), amine INTERMEDIATE 24 (100 mg, 0.33 mmol), biphenyl INTERMEDIATE 22 (85 mg, 0.37 mmol) in MeCN (3 mL). White solid 41 mg (22%). UPLC-MS (method A): Rt 2.43 min, m/z 557 [M+H]$^+$. $^1$H NMR (400 MHz, DMSO-d$_6$) δ 8.12-8.01 (m, 3H), 7.90 (dt, J=7.8, 1.4 Hz, 1H), 7.70 (d, J=7.9 Hz, 1H), 7.64-7.56 (m, 2H), 7.42 (d, J=2.3 Hz, 1H), 7.30 (q, J=3.9 Hz, 2H), 7.22 (dd, J=11.7, 2.3 Hz, 1H), 7.19-7.09 (m, 2H), 5.68 (t, J=3.3 Hz, 2H), 3.74 (s, 2H), 3.05-2.94 (m, 6H), 2.56 (s, 4H).

Example 21. [4-(3-carbamoylphenyl)-3-fluoro-phenyl] N-[4-[4-(2,3-dichlorophenyl)piperazin-1-yl] butyl]carbamate The title compound was synthesized according to the general procedure Ia Method A, starting from di-tert-butyl-dicarbonate (73 mg, 0.33 mmol), 4-dimethylaminopyridine (41 mg, 0.33 mmol) amine INTERMEDIATE 6 (92.0 mg, 0.30 mmol) and phenol INTERMEDIATE 22 (77 mg, 0.33 mmol) in acetonitrile (4 mL). White solid 12 mg (7%). $^1$H NMR (400 MHz, DMSO-d6) δ 8.06 (d, J=22.6 Hz, 1H), 8.01-7.87 (m, 2H), 7.70 (d, J=7.8 Hz, 1H), 7.56 (dp, J=24.1, 8.1, 7.7 Hz, 2H), 7.40 (dd, J=17.3, 8.1 Hz, 1H), 7.34-7.25 (m, 2H), 7.19 (dd, J=11.7, 2.3 Hz, 1H), 7.12 (ddd, J=14.7, 7.5, 2.5 Hz, 2H), 6.80-6.65 (m, 1H), 3.12 (q, J=6.2 Hz, 2H), 2.54 (m, 4H), 2.35 (dt, J=20.4, 6.8 Hz, 4H), 1.60-1.48 (m, 4H), 1.47-1.34 (m, 2H).

Example 22. [4-(3-carbamoylphenyl)phenyl] N-[4-[4-[2-(trifluoromethyl)phenyl]piperazin-1-yl] butyl] carbamate The title compound was synthesized according to the general procedure Ia Method A, starting from di-tert-butyl-dicarbonate (79 mg, 0.36 mmol), 4-dimethylaminopyridine (44 mg, 0.36 mmol) amine INTERMEDIATE 26 (100.0 mg, 0.33 mmol) and phenol INTERMEDIATE 11 (77 mg, 0.36 mmol) in acetonitrile (4 mL). White solid 63 mg (35%). $^1$H NMR (400 MHz, DMSO-d6) δ 8.22-8.04 (m, 2H), 7.94-7.83 (m, 1H), 7.80 (ddt, J=7.6, 5.9, 1.4 Hz, 1H), 7.77-7.69 (m, 1H), 7.64 (qdd, J=7.3, 5.8, 1.7 Hz, 2H), 7.59-7.36 (m, 4H), 7.36-7.28 (m, 2H), 7.27-7.20 (m, 1H), 6.93-6.86 (m, 1H), 2.84 (tt, J=16.8, 4.8 Hz, 6H), 2.48 (s, 4H), 2.33 (dt, J=21.6, 6.8 Hz, 2H), 1.54 (dp, J=8.4, 3.5, 2.9 Hz, 2H), 1.49-1.33 (m, 2H).

Example 23. [3-(3-carbamoylphenyl)phenyl] N-[3-[4-(2-methoxyphenyl)piperazin-1-yl]propyl]carbamate The title compound was synthesized according to the general procedure Ia Method A, starting from di-tert-butyldicarbonate (115 mg, 0.53 mmol), 4-dimethylaminopyridine (64 mg, 0.53 mmol) amine INTERMEDIATE 14 (120.0 mg, 0.48 mmol) and phenol INTERMEDIATE 9 (112 mg, 0.53 mmol) in acetonitrile (4 mL). White solid 70 mg (30%). $^1$H NMR (400 MHz, DMSO-d6) δ 8.17 (t, J=1.8 Hz, 1H), 8.15-8.09 (m, 1H), 7.91-7.80 (m, 3H), 7.62-7.47 (m, 4H), 7.41 (d, J=12.9 Hz, 1H), 7.14 (ddd, J=7.9, 2.4, 1.0 Hz, 1H), 6.98-6.83 (m, 4H), 3.77 (d, J=2.8 Hz, 4H), 3.15 (q, J=6.8 Hz, 2H), 2.97 (m, 4H), 2.52 (m, 4H), 2.40 (t, J=7.1 Hz, 2H), 1.69 (p, J=7.1 Hz, 2H).

Example 24. [4-(2-pyridyl)phenyl] N-[4-[4-(2,3-dichlorophenyl)piperazin-1-yl]butyl]carbamate The title compound was synthesized according to the general procedure Ia Method A, starting from di-tert-butyl-dicarbonate (555 mg, 0.25 mmol), 4-dimethylaminopyridine (31 mg, 0.25 mmol) amine INTERMEDIATE 6 (70.0 mg, 0.23 mmol) and phenol INTERMEDIATE 27 (43 mg, 0.25 mmol) in acetonitrile (4 mL). White solid 34 mg (29%). $^1$H NMR (400 MHz, DMSO-d6) δ 8.66 (dt, J=4.8, 1.3 Hz, 1H), 8.13-8.06 (m, 2H), 7.98-7.82 (m, 3H), 7.37-7.32 (m, 1H), 7.30 (q, J=3.1 Hz, 2H), 7.26-7.19 (m, 2H), 7.14 (td, J=6.8, 3.2 Hz, 1H), 3.12 (q, J=6.2 Hz, 2H), 2.99 (q, J=9.0, 6.6 Hz, 4H), 2.55 (m, 4H), 2.37 (q, J=6.5 Hz, 2H), 1.53 (p, J=3.5 Hz, 4H).

Example 25. [4-(3-carbamoylphenyl)phenyl] N-[4-(4-phenylpiperazin-1-yl)butyl]carbamate The title compound was synthesized according to the general procedure Ia Method B, starting from p-nitrophenylchloroformate (42 mg, 0.21 mmol), DIPEA (0.07 mL, 0.42 mmol), amine INTERMEDIATE 19 (45 mg, 0.19 mmol) and INTERMEDIATE 11 (45 mg, 0.21 mmol) in a 1:1 mixture of DMA:DCM (4 mL). White solid 14 mg (15%). $^1$H NMR (400 MHz, DMSO-d6) δ 8.15 (d, J=2.0 Hz, 1H), 8.13-8.06 (m, 1H), 7.90-7.70 (m, 4H), 7.55 (t, J=7.8 Hz, 1H), 7.51-7.35 (m, 1H), 7.21 (ddd, J=9.1, 5.6, 3.4 Hz, 4H), 6.96-6.85 (m, 3H), 6.77 (t, J=7.2 Hz, 1H), 3.35 (s, 4H), 3.17-3.07 (m, 6H), 2.48 (d, J=5.9 Hz, 2H), 2.34 (q, J=6.7 Hz, 2H), 1.53 (p, J=3.3 Hz, 2H).

Example 26. (3-phenylphenyl) N-[4-[4-(2,3-dichlorophenyl)piperazin-1-yl]butyl]carbamate hydrochloride The title compound was synthesized according to the general procedure Ia Method A, starting from di-tert-butyl-dicarbonate (111 mg, 0.51 mmol), 4-dimethylaminopyridine (53 mg, 0.44 mmol) amine INTERMEDIATE 6 (110.0 mg, 0.36 mmol) and 3-phenylphenol (68 mg, 0.40 mmol) in acetonitrile (4 mL). The resultant oil was dissolved in a small amount of diethyl ether, to which 2M HCl in diethyl ether was added. Evaporation of the solvent produced the title compound as yellow solid 52 mg (27%). $^1$H NMR (400 MHz, DMSO-d6) δ 11.15 (s, 1H), 7.90 (t, J=5.7 Hz, 1H), 7.71-7.63 (m, 2H), 7.49 (dt, J=15.2, 7.7 Hz, 4H), 7.41-7.32 (m, 4H), 7.20 (dd, J=7.0, 2.6 Hz, 1H), 7.12 (dt, J=7.7, 1.7 Hz, 1H), 3.43 (s, 2H), 3.25 (t, J=12.0 Hz, 2H), 3.20-3.08 (m, 8H), 1.90-1.74 (m, 2H), 1.56 (p, J=7.5 Hz, 2H).

Example 27. (4-phenylphenyl) N-[4-[4-(2,3-dichlorophenyl)piperazin-1-yl]butyl]carbamate The title compound was synthesized according to the general procedure Ia Method A, starting from di-tert-butyl-dicarbonate (111 mg, 0.51 mmol), 4-dimethylaminopyridine (53 mg, 0.44 mmol) amine INTERMEDIATE 6 (110.0 mg, 0.36 mmol) and 4-phenylphenol (68 mg, 0.40 mmol) in acetonitrile (4 mL). White solid 42 mg (23%). $^1$H NMR (400 MHz, DMSO-d6) δ 7.83 (t, J=5.7 Hz, 1H), 7.69-7.62 (m, 4H), 7.50-7.43 (m, 2H), 7.39-7.34 (m, 1H), 7.31-7.27 (m, 2H), 7.23-7.16 (m, 2H), 7.14 (dd, J=6.5, 3.2 Hz, 1H), 3.11 (q, J=6.3 Hz, 2H), 2.99 (t, J=4.9 Hz, 4H), 2.54 (s, 4H), 2.38 (d, J=6.7 Hz, 2H), 1.53 (q, J=3.7 Hz, 4H).

Example 28. 9H-carbazol-2-yl N-[4-[4-(2,3-dichlorophenyl)piperazin-1-yl]butyl]carbamate The title compound was synthesized according to the general procedure Ia Method A, starting from di-tert-butyl-dicarbonate (121 mg, 0.56 mmol), 4-dimethylaminopyridine (58 mg, 0.48 mmol) amine INTERMEDIATE 6 (120.0 mg, 0.40 mmol) and 9H-carbazol-2-ol (80 mg, 0.44 mmol) in acetonitrile (4 mL). White solid 43 mg (21%). $^1$H NMR (400 MHz, DMSO-d6) δ 11.26 (s, 1H), 8.07 (t, J=8.2 Hz, 2H), 7.79 (t, J=5.7 Hz, 1H), 7.48 (d, J=8.0 Hz, 1H), 7.36 (t, J=7.6 Hz, 1H), 7.32-7.27 (m, 2H), 7.20 (d, J=2.1 Hz, 1H), 7.19-7.12 (m, 2H), 6.88 (dd, J=8.4, 2.1 Hz, 1H), 3.14 (t, J=6.0 Hz, 2H), 3.02 (d, J=4.9 Hz, 4H), 2.62 (s, 4H), 2.46 (d, J=6.2 Hz, 2H), 1.55 (h, J=3.2 Hz, 4H).

Example 29. (4-phenylphenyl) N-[4-[4-(o-tolyl)piperazin-1-yl]butyl]carbamate

The title compound was synthesized according to the general procedure Ia Method A, starting from di-tert-butyl-dicarbonate (136 mg, 0.62 mmol), 4-dimethylaminopyridine (65 mg, 0.53 mmol) amine INTERMEDIATE 29 (110.0 mg, 0.44 mmol) and 4-phenylphenol (83 mg, 0.49 mmol) in acetonitrile (4 mL). White solid 27 mg (14%). $^1$H NMR (600 MHz, DMSO-d6) δ 7.89 (t, J=5.7 Hz, 1H), 7.69-7.63 (m, 4H), 7.47 (t, J=7.7 Hz, 2H), 7.39-7.35 (m, 1H), 7.23-7.18 (m, 2H), 7.18-7.11 (m, 2H), 7.02 (dd, J=8.0, 1.2 Hz, 1H), 6.95 (td, J=7.3, 1.2 Hz, 1H), 3.12 (q, J=6.3 Hz, 2H), 2.85 (t, J=4.7 Hz, 4H), 2.62-2.52 (m, 4H), 2.37 (d, J=6.5 Hz, 2H), 2.24 (d, J=4.8 Hz, 3H), 1.57-1.48 (m, 4H).

Example 30. (4-phenylphenyl) N-[4-[4-[2-(trifluoromethyl)phenyl]piperazin-1-yl]butyl] carbamate The title compound was synthesized according to the general procedure Ia Method A, starting from di-tert-butyl-dicarbonate (91 mg, 0.42 mmol), 4-dimethylaminopyridine (44 mg, 0.36 mmol) amine INTERMEDIATE 26 (90.0 mg, 0.30 mmol) and 4-phenylphenol (56 mg, 0.33 mmol) in acetonitrile (4 mL). White solid 47 mg (32%). $^1$H NMR (600 MHz, DMSO-d6) δ 7.88 (d, J=6.1 Hz, 1H), 7.66 (d, J=8.4 Hz, 6H), 7.55 (d, J=7.8 Hz, 1H), 7.47 (q, J=7.0, 6.5 Hz, 2H), 7.35 (dt, J=24.8, 7.3 Hz, 2H), 7.20 (d, J=8.3 Hz, 2H), 3.12 (d, J=6.6 Hz, 2H), 2.88 (d, J=5.9 Hz, 4H), 2.51 (s, 4H), 2.36 (d, J=6.4 Hz, 2H), 1.52 (s, 4H).

Example 31. (4-phenylphenyl) N-[3-[4-(2-methoxyphenyl)piperazin-1-yl]propyl]carbamate hydrochloride The title compound was synthesized according to the general procedure Ia Method A, starting from di-tert-butyl-dicarbonate (122 mg, 0.56 mmol), 4-dimethylaminopyridine (59 mg, 0.48 mmol) amine INTERMEDIATE 14 (100.0 mg, 0.40 mmol) and 4-phenylphenol (75 mg, 0.44 mmol) in acetonitrile (4 mL). The resultant oil was dissolved in a small amount of diethyl ether, to which 2M HCl in diethyl ether was added. Evaporation of the solvent produced the title compound as yellow solid 64 mg (33%). $^1$H NMR (400 MHz, DMSO-d6) δ 11.23 (s, 1H), 8.00 (t, J=5.8 Hz, 1H), 7.70-7.63 (m, 4H), 7.47 (dd, J=8.4, 7.0 Hz, 2H), 7.39-7.33 (m, 1H), 7.26-7.20 (m, 2H), 7.07-6.89 (m, 4H), 3.80 (s, 3H), 3.53 (dd, J=22.4, 9.4 Hz, 4H), 3.27-3.09 (m, 8H), 2.07-1.91 (m, 2H).

Example 32. (4-phenylphenyl) N-[4-[4-(2-methoxyphenyl)piperazin-1-yl]butyl]carbamate hydrochloride The title compound was synthesized according to the general procedure Ia Method A, starting from di-tert-butyl-dicarbonate (116 mg, 0.53 mmol), 4-dimethylaminopyridine (56 mg, 0.46 mmol) amine INTERMEDIATE 5 (100.0 mg, 0.38 mmol) and 4-phenylphenol (71 mg, 0.42 mmol) in acetonitrile (4 mL). The resultant oil was dissolved in a small amount of diethyl ether, to which 2M HCl in diethyl ether was added. Evaporation of the solvent produced the title compound as yellow solid 54 mg (29%). $^1$H NMR (400 MHz, DMSO-d6) δ 11.16 (s, 1H), 7.93 (t, J=5.7 Hz, 1H), 7.72-7.62 (m, 4H), 7.47 (dd, J=8.4, 6.9 Hz, 2H), 7.41-7.33 (m, 1H), 7.25-7.19 (m, 2H), 7.09-6.88 (m, 4H), 3.80 (s, 3H), 3.52 (dd, J=18.8, 8.5 Hz, 4H), 3.15 (dq, J=12.9, 6.9, 6.4 Hz, 8H), 1.82 (td, J=11.0, 9.5, 6.2 Hz, 2H), 1.55 (p, J=7.2 Hz, 2H).

Example 33. 9H-carbazol-2-yl N-[4-[4-(2-methoxyphenyl)piperazin-1-yl]butyl]carbamate The title compound was synthesized according to the general procedure Ia Method A, starting from di-tert-butyl-dicarbonate (116 mg, 0.53 mmol), 4-dimethylaminopyridine (56 mg, 0.46 mmol) amine INTERMEDIATE 5 (100.0 mg, 0.38 mmol) and 9H-carbazol-2-ol (77 mg, 0.42 mmol) in acetonitrile (4 mL). White solid 89 mg (50%). $^1$H NMR (400 MHz, DMSO-d6) δ 11.27 (s, 1H), 8.08 (t, J=8.4 Hz, 2H), 7.82 (t, J=5.6 Hz, 1H), 7.49 (d, J=8.1 Hz, 1H), 7.44-7.31 (m, 1H), 7.20 (d, J=2.1 Hz, 1H), 7.16 (t, J=7.4 Hz, 1H), 6.91 (dtd, J=19.6, 5.4, 2.6 Hz, 5H), 3.77 (s, 3H), 3.13 (q, J=6.3 Hz, 2H), 2.97 (s, 4H), 2.53 (d, J=5.0 Hz, 4H), 2.37 (d, J=6.8 Hz, 2H), 1.66-1.47 (m, 4H).

Example 34. [4-(3-carbamoylphenyl)-3-methoxyphenyl] N-[4-[4-(2-methoxyphenyl)piperazin-1-yl]butyl]carbamate The title compound was synthesized according to the general procedure Ia Method A, starting from di-tert-butyl-dicarbonate (93 mg, 0.43 mmol), 4-dimethylaminopyridine (44 mg, 0.36 mmol) amine INTERMEDIATE 5 (80.0 mg, 0.30 mmol) and INTERMEDIATE 39 (81 mg, 0.33 mmol) in acetonitrile (4 mL). White solid 35 mg (22%). $^1$H NMR (400 MHz, DMSO-d6) δ 8.02 (s, 1H), 7.95 (t, J=1.8 Hz, 1H), 7.87 (t, J=5.6 Hz, 1H), 7.82 (dt, J=7.7, 1.5 Hz, 1H), 7.62 (dt, J=7.7, 1.4 Hz, 1H), 7.48 (t, J=7.7 Hz, 1H), 7.38 (s, 1H), 7.32 (d, J=8.3 Hz, 1H), 6.97-6.84 (m, 5H), 6.80 (dd, J=8.2, 2.2 Hz, 1H), 3.77 (s, 3H), 3.76 (s, 3H), 3.12 (q, J=6.3 Hz, 2H), 2.97 (s, 4H), 2.57-2.51 (m, 4H), 2.36 (d, J=6.7 Hz, 2H), 1.53 (p, J=3.6 Hz, 4H).

Example 35. (4-phenylphenyl) N-[3-fluoro-4-[4-(2-methoxyphenyl)piperazin-1-yl]butyl] carbamate hydrochloride The title compound was synthesized according to the general procedure Ia Method A, starting from di-tert-butyl-dicarbonate (130 mg, 0.60 mmol), 4-dimethylaminopyridine (62 mg, 0.51 mmol) amine INTERMEDIATE 38 (120.0 mg, 0.43 mmol) and 4-phenylphenol (80 mg, 0.47 mmol) in acetonitrile (4 mL). The resultant oil was dissolved in a small amount of diethyl ether, to which 2M HCl in diethyl ether was added. Evaporation of the solvent produced the title compound as yellow solid 46 mg (21%). $^1$H NMR (400 MHz, DMSO-d6) δ 11.35 (s, 1H), 8.01 (t, J=5.7 Hz, 1H), 7.74-7.58 (m, 4H), 7.48 (dd, J=8.4, 6.9 Hz, 2H), 7.40-7.33 (m, 1H), 7.28-7.19 (m, 2H), 7.09-6.87 (m, 4H), 5.55-5.25 (m, 1H), 3.81 (s, 3H), 3.65-3.44 (m, 8H), 3.39-3.04 (m, 4H), 1.89 (dq, J=24.7, 6.6, 6.2 Hz, 2H).

Example 36. (4-phenylphenyl) N-[4-[4-(2,3-dichlorophenyl)piperazin-1-yl]-3-fluoro-butyl] carbamate The title compound was synthesized according to the general procedure Ia Method A, starting from di-tert-butyl-dicarbonate (76 mg, 0.35 mmol), 4-dimethylaminopyridine (37 mg, 0.30 mmol) amine INTERMEDIATE 37 (80.0 mg, 0.25 mmol) and 4-phenylphenol (47 mg, 0.27 mmol) in acetonitrile (4 mL). Yellow solid 20 mg (16%). $^1$H NMR (400 MHz, DMSO-d6) δ 7.93 (t, J=5.7 Hz, 1H), 7.69-7.63 (m, 4H), 7.47 (dd, J=8.4, 6.9 Hz, 2H), 7.39-7.33 (m, 1H), 7.32-7.28 (m, 2H), 7.24-7.18 (m, 2H), 7.16 (dd, J=6.0, 3.6 Hz, 1H), 4.97-4.72 (m, 1H), 3.22 (dq, J=16.2, 6.7 Hz, 2H), 3.00 (t, J=4.8 Hz, 4H), 2.67 (qd, J=13.3, 12.8, 6.4 Hz, 6H), 1.97-1.77 (m, 2H).

Example 37. (3-methoxy-4-phenyl-phenyl) N-[3-[4-(2-methoxyphenyl)piperazin-1-yl]propyl] carbamate hydrochloride The title compound was synthesized according to the general procedure Ia Method A, starting from di-tert-butyl-dicarbonate (122 mg, 0.56 mmol), 4-dimethylaminopyridine (59 mg, 0.48 mmol) amine INTERMEDIATE 14 (100.0 mg, 0.40 mmol) and INTERMEDIATE 30 (88 mg, 0.44 mmol) in acetonitrile (4 mL). The resultant oil was dissolved in a small amount of diethyl ether, to which 2M HCl in diethyl ether was added. Evaporation of the solvent produced the title compound as yellow solid 12 mg (6%). $^1$H NMR (400 MHz, DMSO-d6) δ 11.11 (s, 1H), 7.98 (t, J=5.9 Hz, 1H), 7.48-7.44 (m, 2H), 7.41 (dd, J=8.5, 6.8 Hz, 2H), 7.34-7.30 (m, 1H), 7.27 (d, J=8.2 Hz, 1H), 7.07-6.88 (m, 5H), 6.81 (dd, J=8.3, 2.2 Hz, 1H), 3.80 (s, 3H), 3.76 (s, 3H), 3.56-3.44 (m, 4H), 3.29-3.05 (m, 8H), 2.00 (dq, J=11.6, 6.6 Hz, 2H).

Example 38. (3-methoxy-4-phenyl-phenyl) N-[4-[4-(2-methoxyphenyl)piperazin-1-yl]butyl] carbamate The title compound was synthesized according to the general procedure Ia Method A, starting from di-tert-butyl-dicarbonate (139 mg, 0.64 mmol), 4-dimethylaminopyridine (68 mg, 0.55 mmol) amine INTERMEDIATE 5 (120.0 mg, 0.46 mmol) and phenol INTERMEDIATE 30 (100 mg, 0.50 mmol) in acetonitrile (4 mL). Yellow solid 94 mg (42%). $^1$H NMR (400 MHz, DMSO-d6) δ 7.94 (t, J=5.8 Hz, 1H), 7.48-7.43 (m, 2H), 7.40 (dd, J=8.4, 6.6 Hz, 2H), 7.35-7.29 (m, 1H), 7.26 (d, J=8.3 Hz, 1H), 6.99 (dt, J=11.7, 4.6 Hz, 2H), 6.95-6.87 (m, 3H), 6.78 (dd, J=8.3, 2.2 Hz, 1H), 3.79 (s, 3H), 3.75 (s, 3H), 3.39-3.33 (m, 10H), 3.12 (q, J=6.6 Hz, 2H), 1.81 (s, 2H), 1.53 (t, J=7.5 Hz, 2H).

Example 39. [4-(3-carbamoylphenyl)phenyl] N-[4-[4-(o-tolyl)piperazin-1-yl]butyl]carbamate The title compound was synthesized according to the general procedure Ia Method A, starting from di-tert-butyldicarbonate (136 mg, 0.62 mmol), 4-dimethylaminopyridine (65 mg, 0.53 mmol) amine INTERMEDIATE 29 (110.0 mg, 0.44 mmol) and phenol INTERMEDIATE 11 (83 mg, 0.38 mmol) in acetonitrile (4 mL). White solid 30 mg (14%). $^1$H NMR (400 MHz, DMSO-d6) δ 8.26 (t, J=2.0 Hz, 1H), 7.96 (dt, J=7.5, 2.1 Hz, 1H), 7.68 (dt, J=7.5, 2.0 Hz, 1H), 7.65-7.56 (m, 3H), 7.14-7.08 (m, 2H), 7.03 (ddt, J=5.4, 3.1, 1.0 Hz, 1H), 6.92-6.87 (m, 2H), 6.73-6.66 (m, 1H), 6.20 (s, 2H), 5.34 (s, 1H), 3.24 (t, J=7.5 Hz, 2H), 2.98 (t, J=5.1 Hz, 4H), 2.78 (t, J=5.1 Hz, 4H), 2.44 (t, J=5.4 Hz, 2H), 2.22 (d, J=1.1 Hz, 3H), 1.69 (tt, J=7.8, 5.4 Hz, 2H), 1.49 (p, J=7.7 Hz, 2H).

Example 40. [4-(3-carbamoylphenyl)-3-methoxyphenyl] N-[4-[4-(2,3-dichlorophenyl)piperazin-1-yl]butyl]carbamate The title compound was synthesized according to the general procedure Ia Method A, starting from di-tert-butyl-dicarbonate (93 mg, 0.43 mmol), 4-dimethylaminopyridine (44 mg, 0.36 mmol) amine INTERMEDIATE 6 (80.0 mg, 0.26 mmol) and INTERMEDIATE 39 (81 mg, 0.33 mmol) in acetonitrile (4 mL). White solid 35 mg (23%). $^1$H NMR (400 MHz, DMSO-d6) δ 8.03 (t, J=2.0 Hz, 1H), 7.81 (dt, J=7.5, 2.0 Hz, 1H), 7.75 (d, J=7.5 Hz, 1H), 7.66 (dt, J=7.5, 1.9 Hz, 1H), 7.43 (t, J=7.5 Hz, 1H), 7.21-7.15 (m, 2H), 7.03 (d, J=2.1 Hz, 1H), 6.99 (dd, J=7.5, 2.0 Hz, 1H), 6.90 (dd, J=7.0, 2.6 Hz, 1H), 6.20 (s, 2H), 5.34 (s, 1H), 3.90 (s, 3H), 3.24 (t, J=5.1 Hz, 2H), 2.98 (t, J=5.1 Hz, 4H), 2.53 (t, J=5.1 Hz, 4H), 2.44 (t, J=7.5 Hz, 2H), 1.69 (tt, J=7.4, 5.1 Hz, 2H), 1.49 (p, J=5.1 Hz, 2H).

Example 41. (4-phenylphenyl) N-[2-[4-(2,3-dichlorophenyl)piperazin-1-yl]-3-fluoro-propyl] carbamate hydrochloride The title compound was synthesized according to the general procedure Ia Method A, starting from di-tert-butyl-dicarbonate (55 mg, 0.25 mmol), 4-dimethylaminopyridine (31 mg, 0.25 mmol) amine INTERMEDIATE 42 (70.0 mg, 0.23 mmol) and 4-phenylphenol (43 mg, 0.25 mmol) in acetonitrile (4 mL). The resultant oil was dissolved in a small amount of diethyl ether, to which 2M HCl in diethyl ether was added. Evaporation of the solvent produced the title compound as yellow solid 19 mg (15%). $^1$H NMR (400 MHz, DMSO-d6) δ 11.50 (s, 1H), 8.29 (s, 1H), 7.67 (t, J=8.2 Hz, 4H), 7.47 (t, J=7.6 Hz, 2H), 7.43-7.34 (m, 3H), 7.27 (d, J=8.5 Hz, 2H), 7.22 (dd, J=6.9, 2.7 Hz, 1H), 5.28-4.85 (m, 2H), 3.88-3.45 (m, 1H), 3.41-3.24 (m, 10H).

Example 42. (4-benzylphenyl) N-[4-[4-(2-methoxyphenyl)piperazin-1-yl]butyl]carbamate hydrochloride The title compound was synthesized according to the general procedure Ia Method A, starting from di-tert-butyl-dicarbonate (116 mg, 0.53 mmol), 4-dimethylaminopyridine (56 mg, 0.46 mmol) amine INTERMEDIATE 5 (100.0 mg, 0.38 mmol) and 4-benzylphenol (77 mg, 0.42 mmol) in acetonitrile (4 mL). The resultant oil was dissolved in a small amount of diethyl ether, to which 2M HCl in diethyl ether was added. Evaporation of the solvent produced the title compound as yellow solid 97 mg (50%). $^1$H NMR (400 MHz, DMSO-d6) δ 11.29 (s, 1H), 7.84 (t, J=5.7 Hz, 1H), 7.32-7.15 (m, 8H), 7.09-6.97 (m, 5H), 6.92 (td, J=7.5, 1.6 Hz, 1H), 3.93 (s, 2H), 3.80 (s, 3H), 3.51 (dd, J=16.4, 8.5 Hz, 4H), 3.23-3.03 (m, 8H), 1.90-1.73 (m, 2H), 1.51 (p, J=7.2 Hz, 2H).

Example 43. (4-benzylphenyl) N-[3-[4-(2-methoxyphenyl)piperazin-1-yl]propyl]carbamate hydrochloride The title compound was synthesized according to the general procedure Ia Method A, starting from di-tert-butyl-dicarbonate (98 mg, 0.45 mmol), 4-dimethylaminopyridine (47 mg, 0.38 mmol) amine INTERMEDIATE 14 (80.0 mg, 0.32 mmol) and 4-benzylphenol (65 mg, 0.35 mmol) in acetonitrile (4 mL). The resultant oil was dissolved in a small amount of diethyl ether, to which 2M HCl in diethyl ether was added. Evaporation of the solvent produced the title compound as yellow solid 66 mg (41%). $^1$H NMR (400 MHz, DMSO-d6) δ 11.20 (s, 1H), 7.92 (t, J=5.8 Hz, 1H), 7.32-7.16 (m, 8H), 7.07-6.95 (m, 5H), 6.92 (ddd, J=8.0, 6.9, 1.6 Hz, 1H), 3.93 (s, 2H), 3.80 (s, 3H), 3.52 (dd, J=20.1, 9.6 Hz, 4H), 3.20-3.11 (m, 8H), 2.02-1.91 (m, 2H).

Example 44. (4-benzoylphenyl) N-[3-[4-(2-methoxyphenyl)piperazin-1-yl]propyl]carbamate hydrochloride The title compound was synthesized according to the general procedure Ia Method A, starting from di-tert-butyl-dicarbonate (98 mg, 0.45 mmol), 4-dimethylaminopyridine (47 mg, 0.38 mmol) amine INTERMEDIATE 14 (80.0 mg, 0.32 mmol) and (4-hydroxyphenyl)-phenyl-methanone (70 mg, 0.35 mmol) in acetonitrile (4 mL). The resultant oil was dissolved in a small amount of diethyl ether, to which 2M HCl in diethyl ether was added. Evaporation of the solvent produced the title compound as yellow solid 37 mg (23%). $^1$H NMR (400 MHz, DMSO-d6) δ 11.02 (s, 1H), 8.14 (t, J=5.8 Hz, 1H), 7.83-7.77 (m, 2H), 7.77-7.72 (m, 2H), 7.72-7.63 (m, 1H), 7.60-7.53 (m, 2H), 7.37-7.31 (m, 2H), 7.07-6.87 (m, 5H), 3.80 (d, J=2.1 Hz, 3H), 3.53 (dd, J=22.2, 11.7 Hz, 4H), 3.24-3.05 (m, 8H), 2.00 (dd, J=9.9, 6.4 Hz, 2H).

Example 45. (4-benzoylphenyl) N-[4-[4-(2-methoxyphenyl)piperazin-1-yl]butyl]carbamate hydrochloride The title compound was synthesized according to the general procedure Ia Method A, starting from di-tert-butyl-dicarbonate (128 mg, 0.58 mmol), 4-dimethylaminopyridine (61 mg, 0.50 mmol) amine INTERMEDIATE 5 (110.0 mg, 0.42 mmol) and (4-hydroxyphenyl)-phenyl-methanone (91 mg, 0.46 mmol) in acetonitrile (4 mL). The resultant oil was dissolved in a small amount of diethyl ether, to which 2M HCl in diethyl ether was added. Evaporation of the solvent produced the title compound as yellow solid 83 mg (38%). —H NMR (400 MHz, DMSO-d6) δ 11.20 (s, 1H), 8.08 (t, J=5.7 Hz, 1H), 7.81-7.76 (m, 2H), 7.76-7.72 (m, 2H), 7.71-7.66 (m, 1H), 7.60-7.55 (m, 2H), 7.35-7.31 (m, 2H), 7.06-6.88 (m, 5H), 3.80 (s, 3H), 3.51 (dd, J=18.5, 8.1 Hz, 4H), 3.19-3.09 (m, 8H), 1.92-1.75 (m, 2H), 1.55 (p, J=7.1 Hz, 2H).

TABLE OF THE EXAMPLES

| Ex. | Chemical Structure | Molecular Formula | MW |
|---|---|---|---|
| 1 | 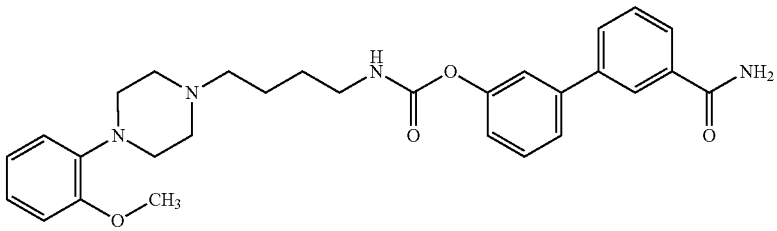 [SMILES: COc1ccccc1N1CCN(CCCCNC(=O)Oc2cccc(-c3cccc(C(N)=O)c3)c2)CC1] | $C_{29}H_{34}N_4O_4$ | 502.6 |
| 2 | 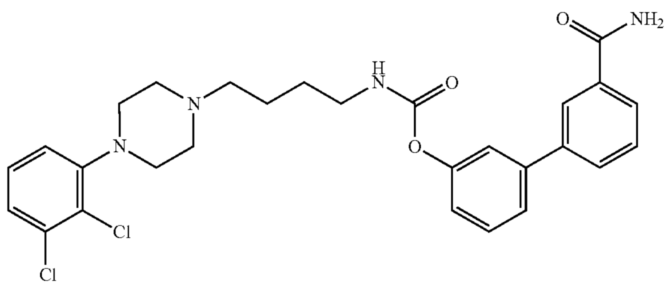 [SMILES: NC(=O)c1cccc(-c2cccc(OC(=O)NCCCCN3CCN(c4cccc(Cl)c4Cl)CC3)c2)c1] | $C_{28}H_{30}Cl_2N_4O_3$ | 541.5 |
| 3 | 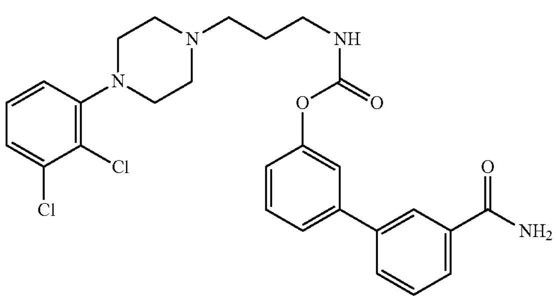 [SMILES: NC(=O)c1cccc(-c2cccc(OC(=O)NCCCN3CCN(c4cccc(Cl)c4Cl)CC3)c2)c1] | $C_{27}H_{28}Cl_2N_4O_3$ | 527.4 |
| 4 | 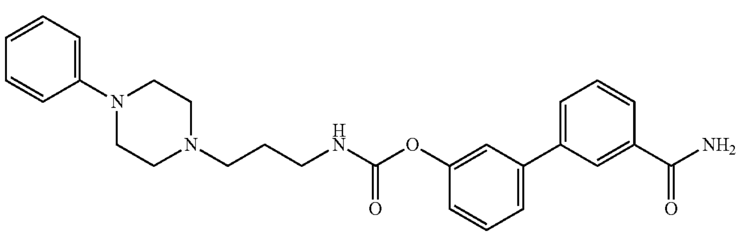 [SMILES: NC(=O)c1cccc(-c2cccc(OC(=O)NCCCN3CCN(c4ccccc4)CC3)c2)c1] | $C_{27}H_{30}N_4O_3$ | 458.6 |
| 5 | 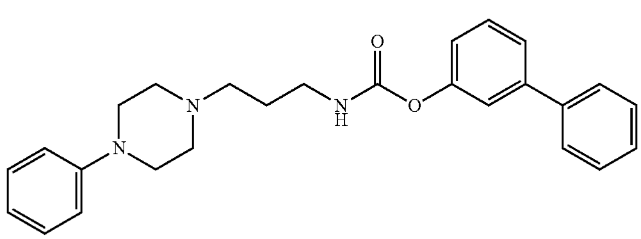 [SMILES: O=C(NCCCN1CCN(c2ccccc2)CC1)Oc1cccc(-c2ccccc2)c1] | $C_{26}H_{29}N_3O_2$ | 415.5 |

TABLE OF THE EXAMPLES-continued
| Ex. | Chemical Structure | Molecular Formula | MW |
|---|---|---|---|
| 6 | 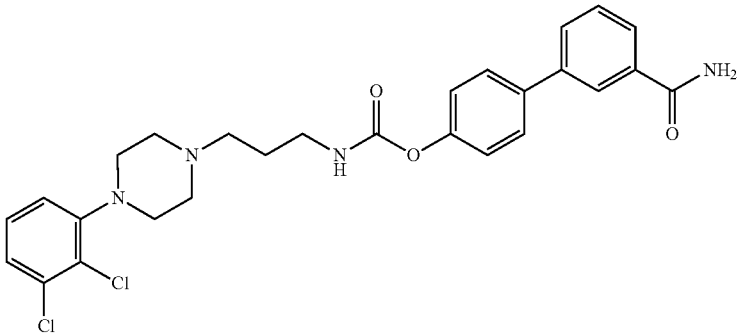 [SMILES: NC(=O)c1cccc(-c2ccc(OC(=O)NCCCN3CCN(c4cccc(Cl)c4Cl)CC3)cc2)c1] | $C_{27}H_{28}Cl_2N_4O_3$ | 527.4 |
| 7 | 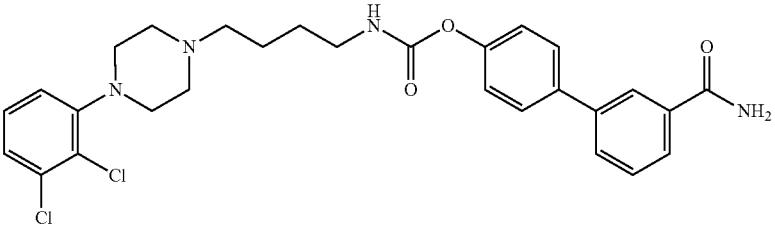 [SMILES: NC(=O)c1cccc(-c2ccc(OC(=O)NCCCCN3CCN(c4cccc(Cl)c4Cl)CC3)cc2)c1] | $C_{28}H_{30}Cl_2N_4O_3$ | 541.5 |
| 8 | 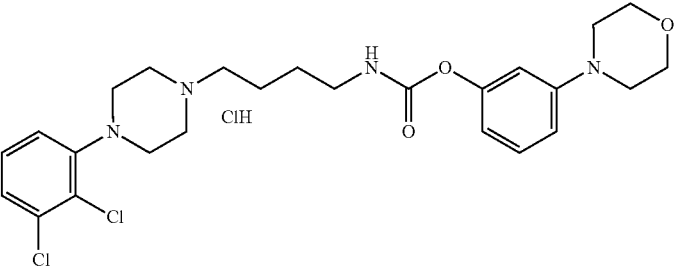 [SMILES: O=C(NCCCCN1CCN(c2cccc(Cl)c2Cl)CC1)Oc1cccc(N2CCOCC2)c1 ; Cl] | $C_{25}H_{32}Cl_2N_4O_3 \cdot HCl$ | 543.8 |
| 9 | 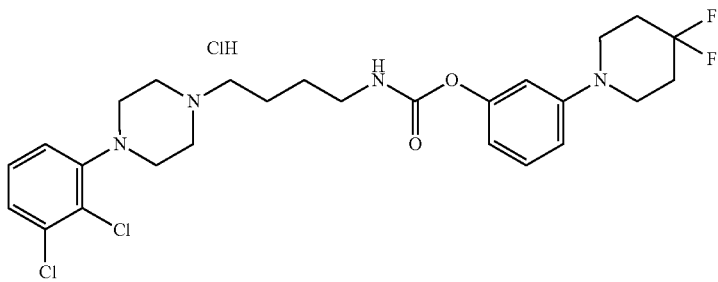 [SMILES: O=C(NCCCCN1CCN(c2cccc(Cl)c2Cl)CC1)Oc1cccc(N2CCC(F)(F)CC2)c1 ; Cl] | $C_{26}H_{32}Cl_3F_2N_4O_2 \cdot HCl$ | 577.9 |
| 10 | 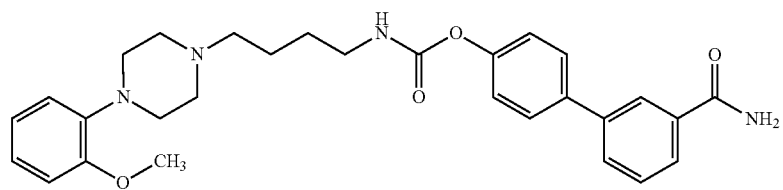 [SMILES: COc1ccccc1N1CCN(CCCCNC(=O)Oc2ccc(-c3cccc(C(N)=O)c3)cc2)CC1] | $C_{29}H_{34}N_4O_4$ | 502.6 |

TABLE OF THE EXAMPLES-continued

| Ex. | Chemical Structure | Molecular Formula | MW |
|---|---|---|---|
| 11 | 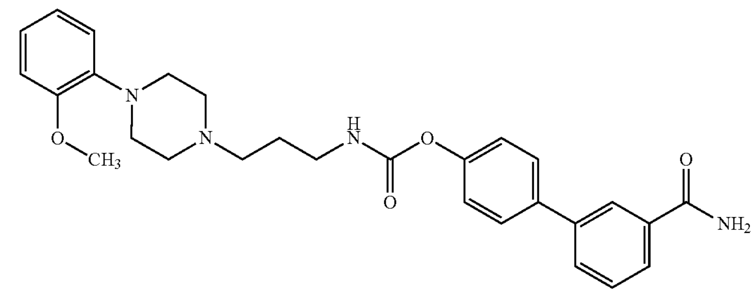 [SMILES: COc1ccccc1N1CCN(CCCNC(=O)Oc2ccc(-c3cccc(C(N)=O)c3)cc2)CC1] | $C_{28}H_{32}N_4O_4$ | 488.6 |
| 12 | 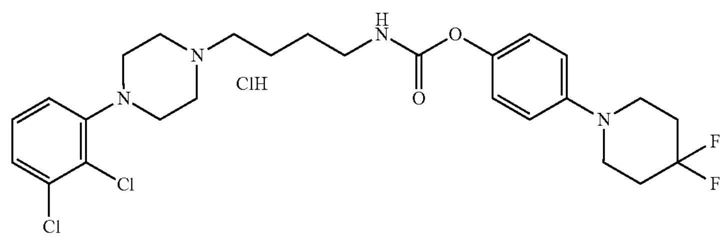 [SMILES: O=C(NCCCCN1CCN(c2cccc(Cl)c2Cl)CC1)Oc1ccc(N2CCC(F)(F)CC2)cc1 ; Cl] | $C_{26}H_{32}Cl_2F_2N_4O_2 \cdot HCl$ | 577.9 |
| 13 | 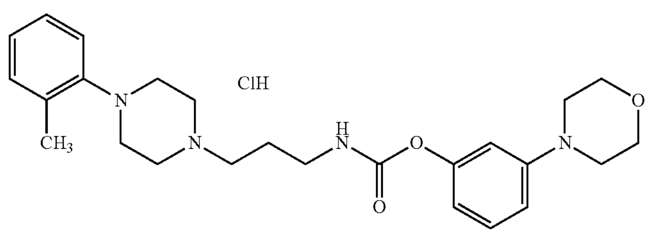 [SMILES: Cc1ccccc1N1CCN(CCCNC(=O)Oc2cccc(N3CCOCC3)c2)CC1 ; Cl] | $C_{25}H_{34}N_4O_3 \cdot HCl$ | 475.0 |
| 14 | 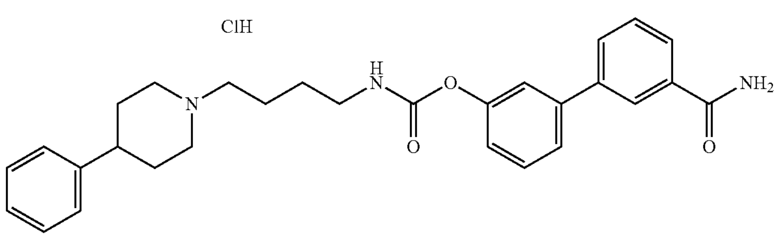 [SMILES: NC(=O)c1cccc(-c2cccc(OC(=O)NCCCCN3CCC(c4ccccc4)CC3)c2)c1 ; Cl] | $C_{29}H_{33}N_3O_3 \cdot HCl$ | 508.0 |
| 15 | 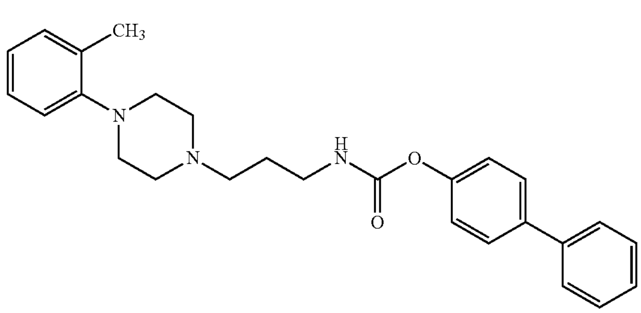 [SMILES: O=C(NCCCN1CCN(c2ccccc2C(F)(F)F)CC1)Oc1ccc(-c2ccccc2)cc1] | $C_{27}H_{31}N_3O_2$ | 429.6 |

TABLE OF THE EXAMPLES-continued

| Ex. | Chemical Structure | Molecular Formula | MW |
|---|---|---|---|
| 16 | 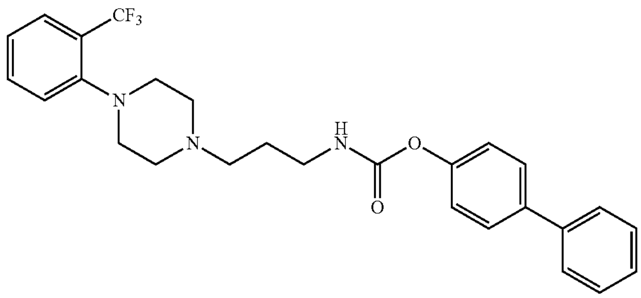 | $C_{27}H_{28}F_3N_3O_2$ | 483.5 |
| 17 | 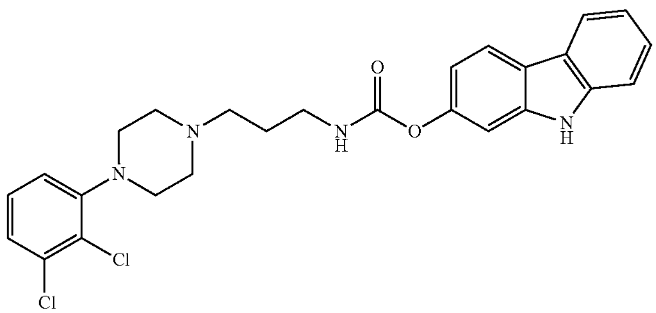 [SMILES: O=C(NCCCN1CCN(c2cccc(Cl)c2Cl)CC1)Oc1ccc2c(c1)[nH]c1ccccc12] | $C_{26}H_{26}Cl_2N_4O_2$ | 496.4 |
| 18 | 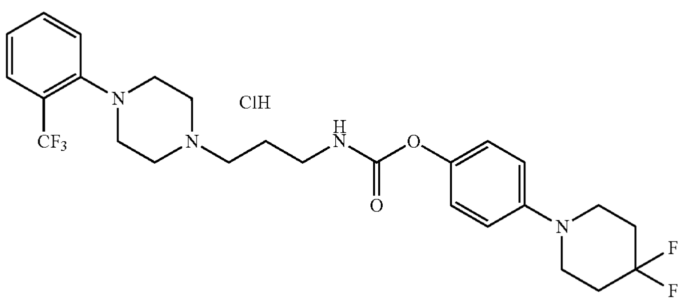 [SMILES: O=C(NCCCN1CCN(c2ccccc2C(F)(F)F)CC1)Oc1ccc(N2CCC(F)(F)CC2)cc1 ; Cl] | $C_{26}H_{31}F_5N_4O_2 \cdot HCl$ | 563.0 |
| 19 | 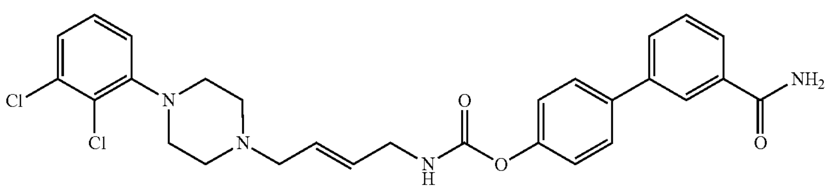 [SMILES: NC(=O)c1cccc(-c2ccc(OC(=O)NC/C=C/CN3CCN(c4cccc(Cl)c4Cl)CC3)cc2)c1] | $C_{28}H_{28}Cl_2N_4O_3$ | 539.4 |
| 20 | 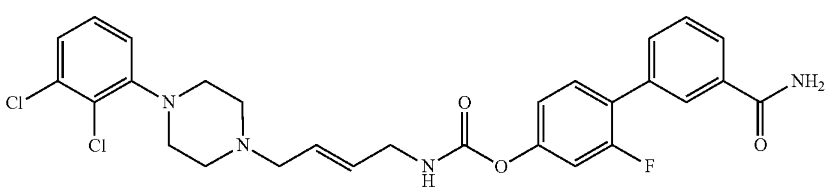 [SMILES: NC(=O)c1cccc(-c2ccc(OC(=O)NC/C=C/CN3CCN(c4cccc(Cl)c4Cl)CC3)cc2F)c1] | $C_{28}H_{27}Cl_2FN_4O_3$ | 557.4 |
| 21 | 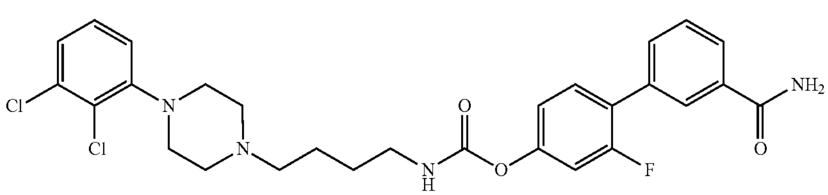 [SMILES: NC(=O)c1cccc(-c2ccc(OC(=O)NCCCCN3CCN(c4cccc(Cl)c4Cl)CC3)cc2F)c1] | $C_{28}H_{29}Cl_2FN_4O_3$ | 559.5 |

TABLE OF THE EXAMPLES-continued

| Ex. | Chemical Structure | Molecular Formula | MW |
|---|---|---|---|
| 22 | 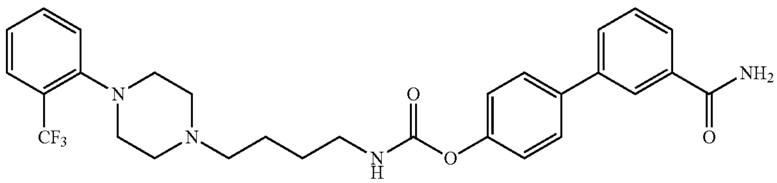 [SMILES: NC(=O)c1cccc(-c2ccc(OC(=O)NCCCCN3CCN(c4ccccc4C(F)(F)F)CC3)cc2)c1] | $C_{29}H_{31}F_3N_4O_3$ | 540.6 |
| 23 | 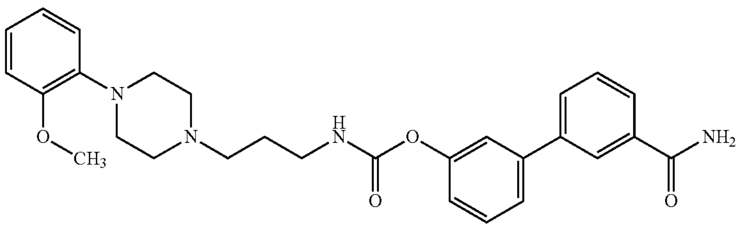 [SMILES: COc1ccccc1N1CCN(CCCNC(=O)Oc2cccc(-c3cccc(C(N)=O)c3)c2)CC1] | $C_{28}H_{32}N_4O_4$ | 488.6 |
| 24 | 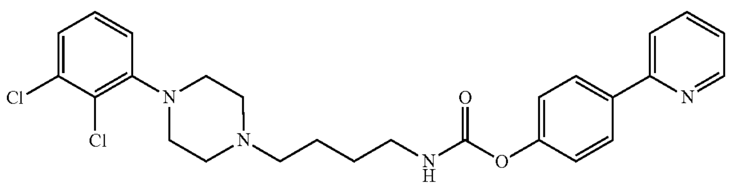 [SMILES: O=C(NCCCCN1CCN(c2cccc(Cl)c2Cl)CC1)Oc1ccc(-c2ccccn2)cc1] | $C_{26}H_{28}Cl_2N_4O_2$ | 499.4 |
| 25 | 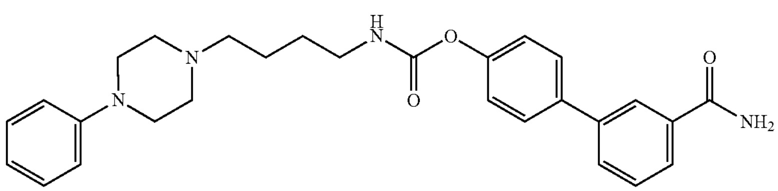 [SMILES: NC(=O)c1cccc(-c2ccc(OC(=O)NCCCCN3CCN(c4ccccc4)CC3)cc2)c1] | $C_{28}H_{32}N_4O_3$ | 472.6 |
| 26 | 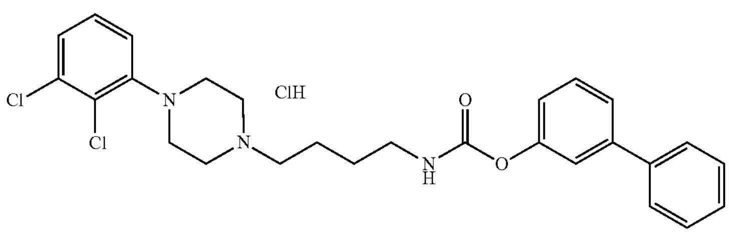 [SMILES: O=C(NCCCCN1CCN(c2cccc(Cl)c2Cl)CC1)Oc1cccc(-c2ccccc2)c1 ; Cl] | $C_{27}H_{29}Cl_2N_3O_2 \cdot HCl$ | 534.9 |
| 27 | 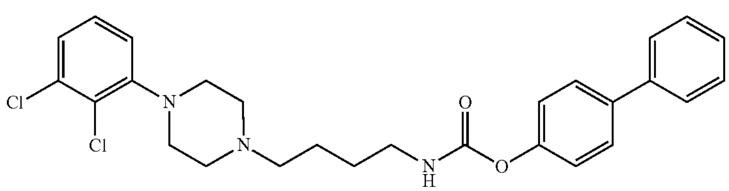 [SMILES: O=C(NCCCCN1CCN(c2cccc(Cl)c2Cl)CC1)Oc1ccc(-c2ccccc2)cc1] | $C_{27}H_{29}Cl_2N_3O_2$ | 498.4 |
| 28 | 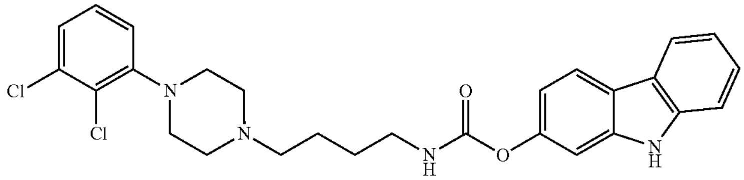 [SMILES: O=C(NCCCCN1CCN(c2cccc(Cl)c2Cl)CC1)Oc1ccc2c(c1)[nH]c1ccccc12] | $C_{27}H_{28}Cl_2N_4O_2$ | 511.4 |

TABLE OF THE EXAMPLES-continued

| Ex. | Chemical Structure | Molecular Formula | MW |
|---|---|---|---|
| 29 | 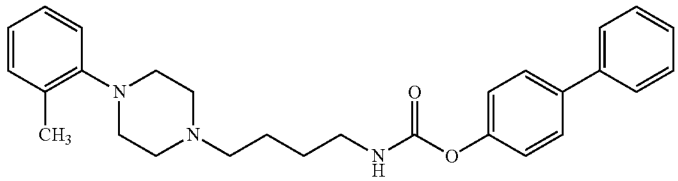 [SMILES: O=C(NCCCCN1CCN(c2ccccc2C(F)(F)F)CC1)Oc1ccc(-c2ccccc2)cc1] | $C_{28}H_{33}N_3O_2$ | 443.6 |
| 30 | 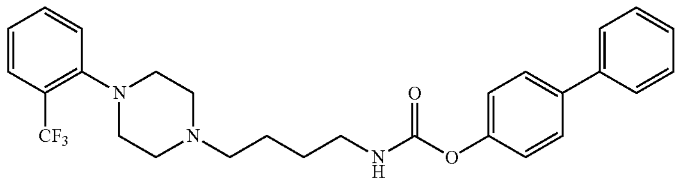 | $C_{28}H_{30}F_3N_3O_2$ | 497.6 |
| 31 | 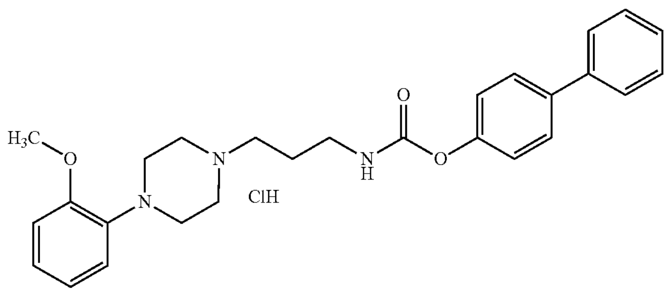 [SMILES: COc1ccccc1N1CCN(CCCNC(=O)Oc2ccc(-c3ccccc3)cc2)CC1 ; Cl] | $C_{27}H_{31}N_3O_3 \cdot HCl$ | 482.0 |
| 32 | 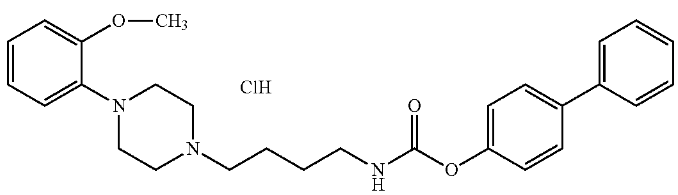 [SMILES: COc1ccccc1N1CCN(CCCCNC(=O)Oc2ccc(-c3ccccc3)cc2)CC1 ; Cl] | $C_{28}H_{33}N_3O_3 \cdot HCl$ | 496.0 |
| 33 | 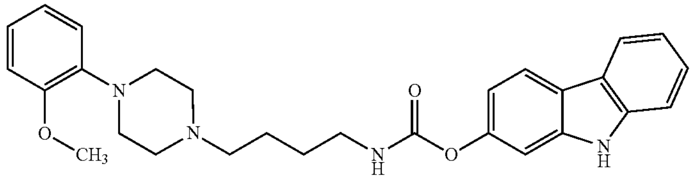 [SMILES: COc1ccccc1N1CCN(CCCCNC(=O)Oc2ccc3c(c2)[nH]c2ccccc23)CC1] | $C_{28}H_{32}N_4O_3$ | 472.6 |
| 34 | 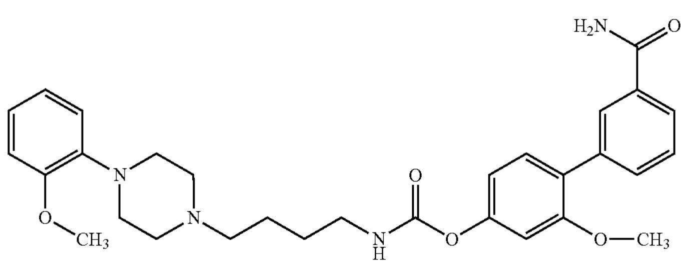 [SMILES: COc1cc(OC(=O)NCCCCN2CCN(c3ccccc3OC)CC2)ccc1-c1cccc(C(N)=O)c1] | $C_{30}H_{36}N_4O_5$ | 532.6 |
| 35 | 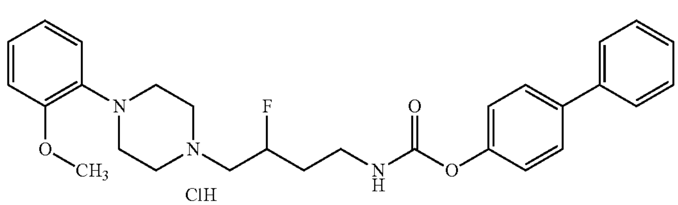 [SMILES: COc1ccccc1N1CCN(CC(F)CCNC(=O)Oc2ccc(-c3ccccc3)cc2)CC1 ; Cl] | $C_{28}H_{32}FN_3O_3 \cdot HCl$ | 514.0 |

TABLE OF THE EXAMPLES-continued

| Ex. | Chemical Structure | Molecular Formula | MW |
|---|---|---|---|
| 36 | 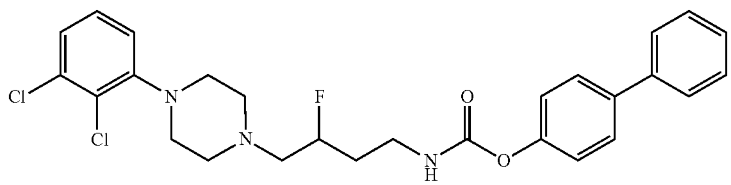 [SMILES: O=C(NCCC(F)CN1CCN(c2cccc(Cl)c2Cl)CC1)Oc1ccc(-c2ccccc2)cc1] | $C_{27}H_{28}Cl_2FN_3O_2$ | 516.4 |
| 37 | 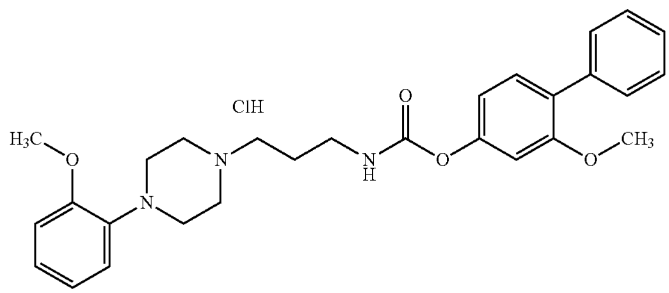 [SMILES: COc1cc(OC(=O)NCCCN2CCN(c3ccccc3OC)CC2)ccc1-c1ccccc1 ; Cl] | $C_{28}H_{33}N_3O_4 \cdot HCl$ | 512.0 |
| 38 | 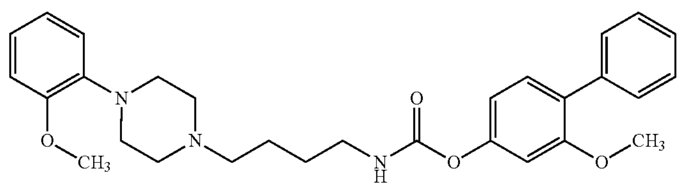 [SMILES: COc1cc(OC(=O)NCCCCN2CCN(c3ccccc3OC)CC2)ccc1-c1ccccc1] | $C_{29}H_{35}N_3O_4$ | 489.6 |
| 39 | 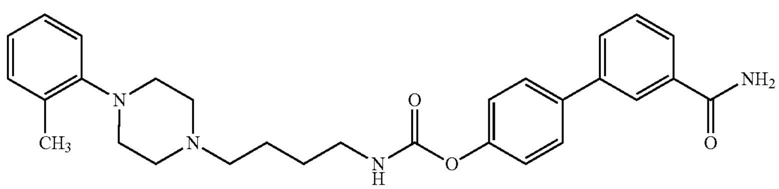 | $C_{29}H_{34}N_4O_3$ | 486.6 |
| 40 | 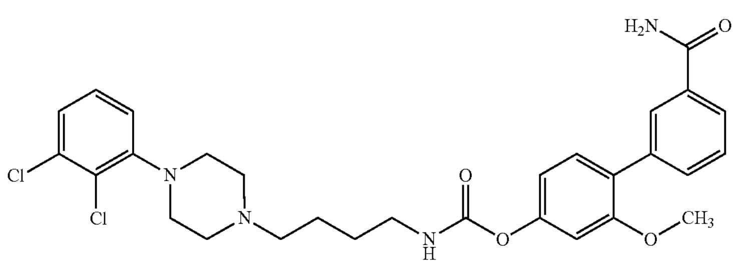 [SMILES: COc1cc(OC(=O)NCCCCN2CCN(c3cccc(Cl)c3Cl)CC2)ccc1-c1cccc(C(N)=O)c1] | $C_{29}H_{32}Cl_2N_4O_4$ | 571.5 |
| 41 | 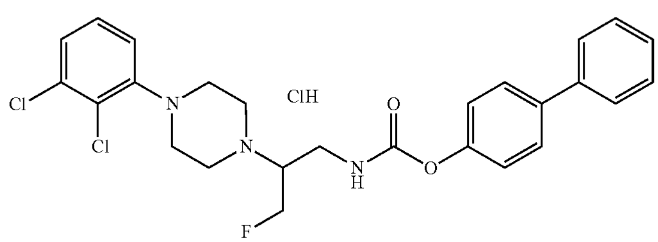 [SMILES: O=C(NCC(CF)N1CCN(c2cccc(Cl)c2Cl)CC1)Oc1ccc(-c2ccccc2)cc1 ; Cl] | $C_{26}H_{26}Cl_2FN_3O_2 \cdot HCl$ | 538.9 |
| 42 | 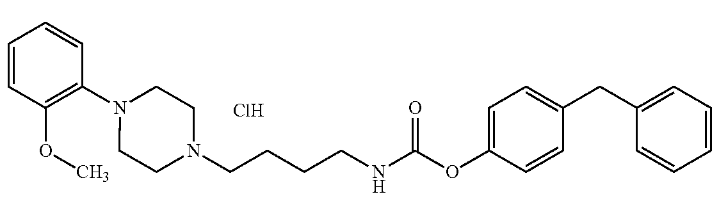 [SMILES: COc1ccccc1N1CCN(CCCCNC(=O)Oc2ccc(Cc3ccccc3)cc2)CC1 ; Cl] | $C_{29}H_{35}N_3O_3 \cdot HCl$ | 510.1 |

TABLE OF THE EXAMPLES-continued

| Ex. | Chemical Structure | Molecular Formula | MW |
|---|---|---|---|
| 43 | 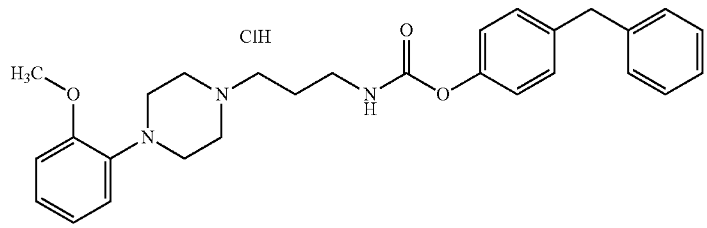 [SMILES: COc1ccccc1N1CCN(CCCNC(=O)Oc2ccc(Cc3ccccc3)cc2)CC1 ; Cl] | $C_{28}H_{33}N_3O_3 \cdot HCl$ | 496.0 |
| 44 | 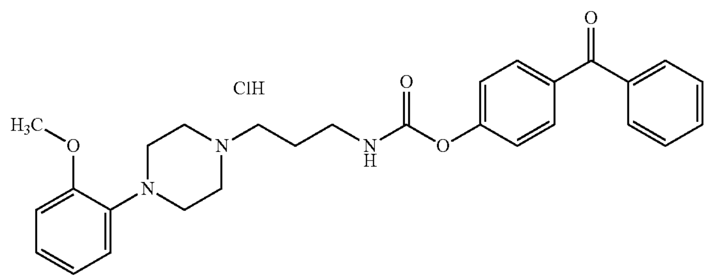 [SMILES: COc1ccccc1N1CCN(CCCNC(=O)Oc2ccc(C(=O)c3ccccc3)cc2)CC1 ; Cl] | $C_{28}H_{31}N_3O_4 \cdot HCl$ | 510.0 |
| 45 | 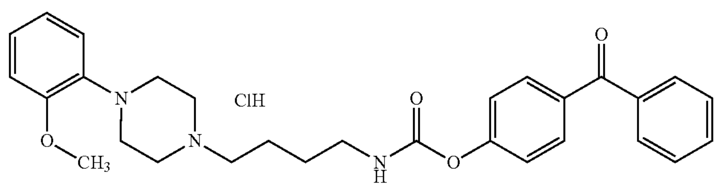 [SMILES: COc1ccccc1N1CCN(CCCCNC(=O)Oc2ccc(C(=O)c3ccccc3)cc2)CC1 ; Cl] | $C_{29}H_{33}N_3O_4 \cdot HCl$ | 524.0 |

Biological Methods to Evaluate the Activity of the Compounds of the Invention

Rat Fatty Acid Amide Hydrolase (FAAH) Assay

Male Sprague Dawley rat brains were homogenized in a potter in 20 mM Tris-HCl pH7.4, 0.32M sucrose, protein concentration was measured and samples aliquot stored at −80° C. until use.

FAAH activity was measured using 50 μg of total rat brain homogenate pre-incubated for 10 minutes at 37° C. in 445.5 μL of assay buffer (50 mM Tris-HCl pH7.4, 0.05% Fatty acid-free BSA) with 4.5 μL of inhibitor at appropriate concentration in DMSO, or DMSO alone to measure FAAH total activity. The blank (no activity sample) was prepared with 445.5 μL of assay buffer and 4.5 μL of DMSO without the 50 μg of total rat brain homogenate.

After 10 minutes of pre-incubation, the reaction was started by the addition of 50 μL of substrate for 30 min at 37° C. The substrate is prepared in assay buffer in order to achieve the final concentration of 1 μM Arachidonoyl-ethanolamide (N.90050, Cayman Chemical) and 0.6 nM Anandamide [ethanolamine-1-$^3$H] (American Radiolabeled Chemicals Inc., ART.0626, 1 mCi/ml, specific activity 60 Ci/mmol).

The reaction was stopped by with the addition of cold 1:1 CHCl$_3$/Methanol. After 10 minutes of centrifugation (845×g at 4° C.) 600 μL of the aqueous phase was transferred into scintillation vials previously filled with 3 mL of scintillation fluid (ULTIMA GOLD, Cat. 6013329, Perkin Elmer Inc.).

Radioactivity was measured by liquid scintillation counting (Microbeta2 Lumijet, Perkin Elmer Inc.).

Human Recombinant Fatty Acid Amide Hydrolase-1 (FAAH-1) Fluorescent Assay

Hek293 cells stably transfected with human FAAH-1 were maintained in DMEM containing 10% FBS, 1% pen/strep and 500 μg/mL G418 to maintain selective pressure. Cells were scraped off with cold PBS1× pH7.4 from plates and collected by centrifugation (500 g, 10 minutes, 4° C.); cells pellets were re-suspended in homogenizing buffer (20 mM Tris-HCl pH7.4, 0.32M sucrose), disrupted by sonication (10 pulses, 5 times) and centrifuged at 800×g for 15 minutes at 4° C.; the resultant supernatants collected were then centrifuged at 105,000×g for 1 hr at 4° C. and membranes pellets were re-suspended in PBS1× pH7.4.

Protein concentration was measured and samples aliquot stored at −80° C. until use.

The fluorescent assay used to measure FAAH activity was performed in 96 wells plates (OptiPlate-96 Black, cat. 6005279, Perkin Elmer Inc.) in a volume of 180 μL/well of assay buffer (50 mM Tris-HCl pH7.4, 0.05% Fatty acid-free BSA) containing 2.5 μg/well of Hek293-hFAAH-1 membrane preparation with 10 μL of inhibitor at appropriate concentration in DMSO, or 10 μL of DMSO alone to measure FAAH total activity. The blank (no activity) was prepared using 180 μL of assay buffer without Hek293-hFAAH-1 membrane preparation and 10 μL of DMSO.

After 50 minutes of pre-incubation of compounds with the enzyme at 37° C., the reaction was started by the addition of 10 μL of substrate (AMC Arachidonyl Amide, N.10005098, Cayman Chemical) for 30 min at 37° C. The substrate is prepared in Ethanol in order to achieve the final concentration of 2 μM.

Fluorescence was detected with Tecan Infinite M200 nanoquant (Tecan Group Ltd.) at an excitation wavelength 350 nm and an emission wavelength 460 nm.

D3 Dopamine Receptor (D3dR) Cellular Assay

Activity on D3R was tested with a cAMP functional assay on a stably transfected human-D3R expressing CHO cell

| Example No. | rat FAAH IC$_{50}$ (nM)[1] | human FAAH IC$_{50}$ (nM)[2] | Dopamine D3 EC$_{50}$ (nM)[3] | Dopamine D3 % of Agonist Activity[4] |
|---|---|---|---|---|
| 1 | 0.94 | 4.4 | 14.0 | 30.7% |
| 2 | 0.3 | 1.6 | 6.5 | 51.7% |
| 3 | 0.11 | 1.4 | 3.9 | 64.8% |
| 4 | 0.32 | 1.6 | 6.5 | 94.3% |
| 5 | 3 | 3.4 | 13.0 | 89.7% |
| 6 | 1.5 | 0.46 | 0.9 | 67.9% |
| 7 | 0.72 | 0.63 | 1.0 | 55.6% |
| 8 | NA | 3.4 | 35 | 83.0% |
| 9 | NA | 17 | 9.2 | 54.7% |
| 10 | NA | 10.7 | 0.88 | 61.6% |
| 11 | NA | 2.8 | 7.38 | 68.9% |
| 12 | NA | 9.9 | 49 | 90.7% |
| 13 | NA | 4.4 | 150 | 59.4% |
| 14 | NA | 9.6 | 36 | 74.3% |
| 15 | NA | 4.1 | 290 | 82.0% |
| 16 | NA | 12 | 300 | 95.4% |
| 17 | NA | 4.8 | 150 | 91.0% |
| 18 | NA | 28 | 190 | 86.0% |
| 19 | NA | 1.2 | 37.8 | A |
| 20 | NA | 0.59 | 6.93 | A |
| 21 | NA | 0.96 | 18.6 | 69.4% |
| 22 | NA | 2.7 | 11 | 77.0% |
| 23 | NA | 1.8 | 19 | 61.9% |
| 24 | NA | 0.21 | 5.92 | 70.4% |
| 25 | NA | 3.5 | 3.6 | 87.5% |
| 26 | NA | 4.1 | 240 | 85.4% |
| 27 | NA | 0.91 | 18 | 63.1% |
| 28 | NA | 8 | 120 | 89.7% |
| 29 | NA | 7.6 | 130 | 52.6% |
| 30 | NA | 2.6 | 14 | 81.5% |
| 31 | NA | 2.6 | 14 | 81.5% |
| 32 | NA | 39 | 300 | 84.6% |
| 33 | NA | 37 | 12 | 65.9% |
| 34 | NA | 63 | 3.9 | 51.1% |
| 36 | NA | 1.3 | 150 | 87.6% |
| 37 | NA | 7.8 | 38 | 73.5% |
| 38 | NA | 43 | 37 | 74.0% |
| 39 | NA | 3 | 4.03 | 72.2% |
| 40 | NA | 2.7 | 4.41 | 81.1% |
| 41 | NA | 9.9 | NA | NA |
| 43 | NA | 18 | NA | NA |
| 44 | NA | 11 | NA | NA |
| 45 | NA | 5.3 | 29 | 51.4% |

[1] Each IC$_{50}$ is the result of 3 separate experiments, each conducted in duplicate
[2] Each IC$_{50}$ is the result of 3 separate experiments, each conducted in triplicate
[3] Each EC$_{50}$ is the result of an experiment conducted in duplicate
[4] Results are expressed as a % of 300 nM Dopamine response;
A = Antagonist
NA = not available

The invention claimed is:
1. A compound of Formula (I) or a pharmaceutically acceptable salt thereof

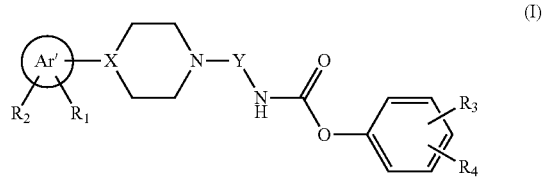

(I)

wherein:
Ar' is a benzene, indole, naphthyl or pyridine ring;
$R_1$ and $R_2$ are independently selected from the group consisting of hydrogen, halogen, linear or branched $C_{1-6}$alkyl, $C_{1-6}$alkoxy, OH, $CF_3$; $R_1$ and $R_2$ can be attached in any position of the Ar' group;
X is N;
Y is an alkylene or alkenylene group selected from the group consisting of

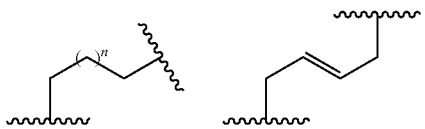

where n is 0 or an integer from 1 to 3 and wherein Y is optionally substituted by up to two same or different substituents B attached to any position of the Y group;
B is selected in the group consisting of F, OH, and $CH_2OH$;
$R_3$ is a phenyl, benzyl, benzoyl or a pyridine ring attached to phenyl ring in the meta or para position and optionally substituted by up to two same or different substituents $R_5$, wherein $R_5$ is halogen, $C_{1-6}$alkyl or a group $CONH_2$ or $CONHCH_3$ attached to $R_3$ in the meta or para position;
or $R_3$ is a 5- to 7-membered heterocyclic ring comprising up to 2 heteroatoms selected from N, O and S attached to the phenyl ring in the meta or para position and optionally substituted by up to two same or different substituents $R_6$, wherein $R_6$ is gem-difluoro, gem-dimethyl, COMe, attached to $R_3$ in any position of the ring; and wherein the group $R_3$ can be attached to any position of the phenyl ring;
$R_4$ is hydrogen, halogen, linear or branched $C_{1-6}$alkyl, $C_{1-6}$ alkoxy, hydroxy$C_{1-6}$alkyl, $CF_3$; the group $R_4$ can be attached to any position of the phenyl ring;

or $R_3$ and $R_4$ together with the phenyl ring to which they are connected may form a 9H-carbazole ring.

2. A compound of Formula (I) according to claim 1 wherein:

$R_1$ and $R_2$ are, independently, hydrogen, halogen, $C_{1-6}$ alkoxy, $CF_3$;

X is N;

Y is $CH_2$—$(CH_2)_n$—$CH_2$, where n is 0 or an integer from 1 to 2, or a group $CH_2$—CH═CH—$CH_2$, $CH_2CH(OH)$ $CH_2CH_2$, $CH_2CH(F)CH_2$, $CH_2CH(F)CH_2CH_2$, $CH_2CH(OH)CH_2$, $CH(CH_2F)CH_2$, $CH(CH_2F)$ $CH_2CH_2$, $CH(CH_2OH)CH_2$;

$R_4$ is hydrogen, halogen, $C_{1-6}$alkyl, $C_{1-6}$alkoxy, $CF_3$; the group $R_4$ can be attached to the phenyl ring in any position of the ring;

or $R_3$ and $R_4$ together with the phenyl ring to which they are connected may form a 9H-carbazole ring.

3. A compound of Formula (I) according to claim 2, wherein:

Ar' is a benzene ring;

$R_1$ and $R_2$ are, independently, H, Cl, or OMe, Me, $CF_3$; X is N;

Y is $CH_2$—$(CH_2)_n$—$CH_2$, where n is 0 or an integer from 1 to 2, or a group $CH_2$—CH═CH—$CH_2$, a group $CH(CH_2F)CH_2$, or a group $CH_2CH(F)CH_2CH_2$;

$R_3$ is a phenyl, benzyl, benzoyl or pyridine ring attached to the phenyl ring in the meta or para position and optionally substituted with a group $CONH_2$ or $CONHCH_3$ attached to $R_3$ in the meta or para position;

or $R_3$ is a 1-pyrrolidinyl or 1-piperidinyl or 1-piperazinyl or 4-morpholinyl ring attached to the phenyl ring in the meta or para position and optionally substituted with gem-difluoro;

$R_4$ is hydrogen, F, Me or OMe; the group $R_4$ can be attached to the phenyl ring in any position of the ring;

or $R_3$ and $R_4$ together with the phenyl ring to which they are connected may form a 9H-carbazole ring.

4. Compounds according to claim 1, selected from the group consisting of:

[3-(3-carbamoylphenyl)phenyl] N-[4-[4-(2-methoxyphenyl)piperazin-1-yl]butyl] carbamate;

[3-(3-carbamoylphenyl)phenyl] N-[4-[4-(2,3-dichlorophenyl)piperazin-1-yl]butyl] carbamate;

[3-(3-carbamoylphenyl)phenyl] N-[3-[4-(2,3-dichlorophenyl)piperazin-1-yl]propyl] carbamate;

[3-(3-carbamoylphenyl)phenyl] N-[3-(4-phenylpiperazin-1-yl)propyl] carbamate;

(3-phenylphenyl) N-[3-(4-phenylpiperazin-1-yl)propyl] carbamate;

[4-(3-carbamoylphenyl)phenyl] N-[3-[4-(2,3-dichlorophenyl)piperazin-1-yl]propyl] carbamate;

[4-(3-carbamoylphenyl)phenyl] N-[4-[4-(2,3-dichlorophenyl)piperazin-1-yl]butyl] carbamate;

(3-morpholinophenyl) N-[4-[4-(2,3-dichlorophenyl)piperazin-1-yl]butyl] carbamate hydrochloride;

[3-(4,4-difluoro-1-piperidinyl)phenyl] N-[4-[4-(2,3-dichlorophenyl)piperazin-1-yl]butyl] carbamate hydrochloride;

[4-(3-carbamoylphenyl)phenyl] N-[3-[4-(2-methoxyphenyl)piperazin-1-yl]propyl] carbamate;

[4-(4,4-difluoro-1-piperidinyl)phenyl] N-[4-[4-(2,3-dichlorophenyl)piperazin-1-yl]butyl] carbamate hydrochloride;

(3-morpholinophenyl) N-[3-[4-(o-tolyl)piperazin-1-yl] propyl] carbamate hydrochloride;

(4-phenylphenyl) N-[3-[4-(o-tolyl)piperazin-1-yl]propyl] carbamate;

(4-phenylphenyl) N-[3-[4-[2-(trifluoromethyl)phenyl] piperazin-1-yl]propyl] carbamate;

9H-carbazol-2-yl N-[3-[4-(2,3-dichlorophenyl)piperazin-1-yl]propyl]carbamate;

[4-(4,4-difluoro-1-piperidinyl)phenyl] N-[3-[4-[2-(trifluoromethyl)phenyl] piperazin-1-yl]propyl] carbamate hydrochloride;

[4-(3-carbamoylphenyl)phenyl] N-[(E)-4-[4-(2,3-dichlorophenyl)piperazin-1-yl] but-2-enyl] carbamate;

[4-(3-carbamoylphenyl)-3-fluoro-phenyl] N-[(E)-4-[4-(2,3-dichlorophenyl) piperazin-1-yl]but-2-enyl] carbamate.

5. A pharmaceutical composition containing an effective amount of a compound of Formula (I) according to claim 1 or a pharmaceutically salt thereof and at least one pharmaceutically acceptable excipient.

* * * * *